US010390774B2

(12) United States Patent
Besson

(10) Patent No.: US 10,390,774 B2
(45) Date of Patent: Aug. 27, 2019

(54) ANNULAR RING TARGET MULTI-SOURCE CT SYSTEM

(71) Applicant: Guy M. Besson, Broomfield, CO (US)

(72) Inventor: Guy M. Besson, Broomfield, CO (US)

( * ) Notice: Subject to any disclaimer, the term of this patent is extended or adjusted under 35 U.S.C. 154(b) by 445 days.

(21) Appl. No.: 15/200,435

(22) Filed: Jul. 1, 2016

(65) Prior Publication Data

US 2016/0310086 A1    Oct. 27, 2016

Related U.S. Application Data

(63) Continuation-in-part of application No. 15/047,412, filed on Feb. 18, 2016, now Pat. No. 9,775,579, and a continuation-in-part of application No. 14/946,626, filed on Nov. 19, 2015, now Pat. No. 9,895,125.

(60) Provisional application No. 62/188,309, filed on Jul. 2, 2015, provisional application No. 62/286,303, filed on Jan. 22, 2016, provisional application No.
(Continued)

(51) Int. Cl.
*A61B 6/00* (2006.01)
*A61B 6/03* (2006.01)

(52) U.S. Cl.
CPC ............ *A61B 6/035* (2013.01); *A61B 6/032* (2013.01); *A61B 6/4007* (2013.01); *A61B 6/4452* (2013.01); *A61B 6/5205* (2013.01); *A61B 6/54* (2013.01)

(58) Field of Classification Search
None
See application file for complete search history.

(56) References Cited

U.S. PATENT DOCUMENTS 4,150,293 A    4/1979 Franke
5,481,585 A *  1/1996 Kimura ............... F16C 32/0444
                                                  378/10
(Continued)

FOREIGN PATENT DOCUMENTS

WO    2014028930 A1    2/2014

OTHER PUBLICATIONS

U.S. Appl. No. 14/946,626, Office Action dated Jul. 13, 2017, 8 pages.
(Continued)

*Primary Examiner* — Hoon K Song
(74) *Attorney, Agent, or Firm* — Lathrop Gage LLP

(57) ABSTRACT

A multiple-source CT system has an annular vacuum chamber surrounding a passage wherein lies an object. A target is in the chamber, the passage passing through an opening of the target. Multiple electron beam emitters are on an emitter gantry within the chamber, each emitting an electron beam towards the target to cause x-rays. An x-ray detector array is mounted on a detector gantry and feeds an image processing system configured to generate tomographic images of the object from detector data. In embodiments, multiple electron beam emitters energize simultaneously. In embodiments, target and emitter gantry counter-rotate. The method includes rotating electron-beam emitters with respect to the target to generate x-rays from the target while rotating a detector about a passage and acquiring data from the detector while multiple detector elements receive x-rays stimulated by multiple emitters, forming a sinogram, and processing the sinogram into a tomographic image of the object.

24 Claims, 37 Drawing Sheets

Related U.S. Application Data

62/186,991, filed on Jun. 30, 2015, provisional application No. 62/118,591, filed on Feb. 20, 2015, provisional application No. 62/117,868, filed on Feb. 18, 2015, provisional application No. 62/081,858, filed on Nov. 19, 2014, provisional application No. 62/299,392, filed on Feb. 24, 2016.

(56) References Cited

U.S. PATENT DOCUMENTS

| | | | |
|---|---|---|---|
| 5,841,141 | A | 11/1998 | Gullberg et al. |
| 6,973,158 | B2 | 12/2005 | Besson |
| 8,755,493 | B2 | 6/2014 | Travish et al. |
| 2006/0008047 | A1* | 1/2006 | Zhou ............ A61B 6/032 378/10 |
| 2006/0233295 | A1 | 10/2006 | Edic et al. |
| 2008/0049891 | A1 | 2/2008 | Yin et al. |
| 2008/0137805 | A1* | 6/2008 | Forster ............ A61B 6/032 378/10 |
| 2008/0317197 | A1 | 12/2008 | Matsuzaki et al. |
| 2009/0101838 | A1 | 4/2009 | Boyden et al. |
| 2010/0135454 | A1 | 6/2010 | Noo |
| 2010/0322498 | A1 | 12/2010 | Wieczorek et al. |
| 2011/0188724 | A1 | 8/2011 | Bruder |
| 2013/0121553 | A1 | 5/2013 | Thibault et al. |
| 2013/0251097 | A1 | 8/2013 | Zou |
| 2014/0241489 | A1 | 8/2014 | Zhang et al. |
| 2015/0366522 | A1 | 12/2015 | Besson |

OTHER PUBLICATIONS

U.S. Appl. No. 15/047,412 Notice of Allowance dated Aug. 2, 2017, 9 pages.

International Search Report and Written Opinion corresponding to International Patent Application No. PCT/US2015/061679; dated Mar. 29, 2016; 14 pages.

Besson, G. M.; New CT system architectures for high temporal resolution with applications to improved geometric dose efficiency and cardiac imaging; Medical Physics 42, 2668-2678 (May 2015).

Besson, G.M.; Old Ideas New Again: A System Concept for Fast CT Using Semi-Conventional Approaches; The third international conference on image formation in X-ray computed tomography; pp. 303-306.

Besson, G.M.; A new CT system architecture for high temporal resolution with applications to improved geometric dose efficiency and sparse sampling; Medical Imaging 2015: Physics of Medical Imaging, edited by Christoph Hoeschen, Despina Kontos, Proc. of Spie vol. 9412; pp. 94120Y-1-94120Y-11.

\* cited by examiner

FIG. 4 – PRIOR ART

ANNULAR RING TARGET MULTI-SOURCE CT SYSTEM

CROSS-REFERENCE TO RELATED APPLICATIONS

This present document claims priority to U.S. Provisional Patent Application No. 62/188,309 filed 2 Jul. 2015. The present application also is a continuation-in-part of U.S. Nonprovisional patent application Ser. No. 15/047,412 filed 18 Feb. 2016, which in turn is a continuation-in-part of U.S. Nonprovisional patent application Ser. No. 14/946,626 filed 19 Nov. 2015, and claims priority to U.S. Provisional Patent Application No. 62/117,868 filed 18 Feb. 2015, U.S. Provisional Patent Application No. 62/118,591 filed 20 Feb. 2015, U.S. Provisional Patent Application No. 62/186,991 filed 30 Jun. 2015 and to U.S. Provisional Patent Application No. 62/286,303 filed 22 Jan. 2016.

This present application also is a continuation-in-part of U.S. Nonprovisional patent application Ser. No. 14/946,626, filed 19 Nov. 2015, which in turn claims priority to U.S. Provisional Patent Application 62/186,991 filed 30 Jun. 2015, U.S. Provisional Patent Application 62/118,591 filed 20 Feb. 2015, and U.S. Provisional Patent Application No. 62/081,858 filed 19 Nov. 2014. This present application also claims priority to U.S. Provisional Patent Applications 62/286,303 filed 22 Jan. 2016 and to U.S. Provisional Patent Application 62/299,392 filed 24 Feb. 2016.

The contents of the aforementioned patent applications are incorporated herein by reference in their entireties.

FIELD OF THE INVENTION

This disclosure relates to the field of computed tomography (CT) imaging, and more particularly to the design of multi-source CT systems for high-temporal resolution and high throughput imaging. In particular, the disclosure addresses multi-source X-ray computed tomography, although it is not limited to computed tomography modalities using X-rays.

BACKGROUND

Since the beginning of CT, cardiac imaging has been a key technology driver. Multiple innovations have attempted to address the associated need for high temporal resolution. Although current CT systems can image a cross-section of the heart in about 100 milliseconds or less, this may not be sufficiently fast for obtaining full diagnostic information. This is particularly the case when imaging uncooperative patients or patients with arrhythmia.

Organ, body, or object speed of coverage in CT is achieved through a combination of effective source rotation speed and longitudinal (or "z") —extent of the detector. Source rotation angular velocity is limited by the flux requirement and the capability of source sub-systems to withstand the large rotation-related accelerations.

In the mid-1980s, electron beam tomography (EBT) was developed as a means to acquire projection data for one or up to four tomographic slices in about 50 milliseconds. The technology circumvented the mechanical difficulties associated with the accelerations above mentioned, but did not provide a high enough X-ray beam flux to enable high contrast-to-noise imaging and also suffered from a number of additional technological limitations, such as the requirement for an intrinsic cone-angle in the acquisition data—that is, the central detector plane and the X-ray source rotation plane are necessarily offset along the main system axis ("z").

CT systems with a rotating gantry typically have only one radiation source; although at least one medical imaging system is commercially available with two radiation sources, leading to a factor two temporal resolution increase in specific applications, such as cardiac imaging. In that system, the X-ray projections from the two sources do not overlap on the detector side, and, due to space constraints on the rotating gantry, the imaging field-of-view exposed by both sources is limited as compared to single-source CT.

Rotating anode tube designs have adapted to the requirement for higher flux by providing larger diameter anodes and higher anode rotation speeds. These anode diameter increases however only compound the mechanical challenges associated with high angular velocities around the imaging field-of-view (FOV).

Certain CT aviation security systems use multiple sources arranged on a fixed gantry. With today's X-ray tube technology, this necessarily results in a relatively sparse sampling in the view-angle (projection-angle) direction.

SUMMARY

The methods and systems disclosed herein allow for high temporal imaging and throughput in medical imaging, security, and inspection applications. In particular, system designs are introduced that significantly increase imaging speed and temporal resolution in comparison to the state-of-the-art.

In an embodiment, a multiple-source computed tomography system has an annular vacuum chamber surrounding a passage wherein lies the object to be imaged. A target ring is in the chamber, the passage passing through an opening of the target ring. Multiple electron beam emitters are on an emitter gantry within the vacuum chamber, each adapted to emit an electron beam towards the target ring to cause x-ray emissions therefrom. An x-ray radiation detector array mounted upon a rotatable detector gantry lies within the passage and feeds an image processing system configured to generate tomographic images from the projection data received from the radiation detector array. In particular embodiments, multiple electron beam emitters are energized simultaneously. In particular embodiments, the target ring and emitter gantry counter-rotate.

In another embodiment, a multiple-source computed tomography system has an annular vacuum chamber surrounding a passage within which is an item to be imaged. An annular rotatable emitter structure lies within the chamber, the emitter structure having an opening through which the passage passes. Multiple electron beam emitters are attached to the emitter structure, each configured to emit an electron beam towards at least one target to cause emissions of x-rays. An x-ray radiation detector array lies within the passage on a rotatable gantry. An image processing system receives data from the radiation detector array and generates tomographic images using data from the radiation detector array.

A method embodiment includes rotating electron-beam emitters with respect to a target ring about a passage to stimulate x-rays from the target ring while rotating a radiation detector array about the passage and acquiring data from the detector while multiple detector elements receive x-rays stimulated by multiple emitters, processing the data to form a sinogram, and processing the sinogram into a three dimensional (tomographic) image of radiation attenuation within an object.

A multiple-source computed tomography system has an annular vacuum chamber disposed around a passage, and a supporting system configured to support within the passage an item to be imaged. Within the annular vacuum chamber are a first and second target ring, the passage passing through an opening of each of the first and second target ring, and a plurality of electron beam emitters mounted to an emitter gantry, each electron beam emitter configured to emit an electron beam towards the first target ring or the second target ring and to cause emissions of x-rays at focal points of the electron beam on the target ring. The system has a first and a second x-ray radiation detector array disposed within the passage, the first radiation detector array disposed to receive radiation from the first target ring and the second radiation detector disposed to receive radiation from the second target ring, and an image processing system configured to receive projection data from the first and second radiation detector array, and to generate tomographic images from the projection data received from the radiation detector array.

The foregoing embodiments may also serve in dual energy or multi-spectral imaging. In specific embodiments, pair of emitter sources replaces each emitter source, such that when power is toggled between the two sources of the pair, two sets of complete projection data are acquired, one set at each of two well-separated energy levels.

Still further, the disclosed instrumentalities are described with various geometric dimensions that define one of a typical medical imaging geometry, a typical aviation security imaging geometry, and a typical inspection imaging geometry.

Other objects and advantages of the present disclosure will become apparent from the following descriptions, taken in connection with the accompanying drawings, wherein, by way of illustration and example, embodiments of the present invention are disclosed.

DEFINITIONS

Figure 1:
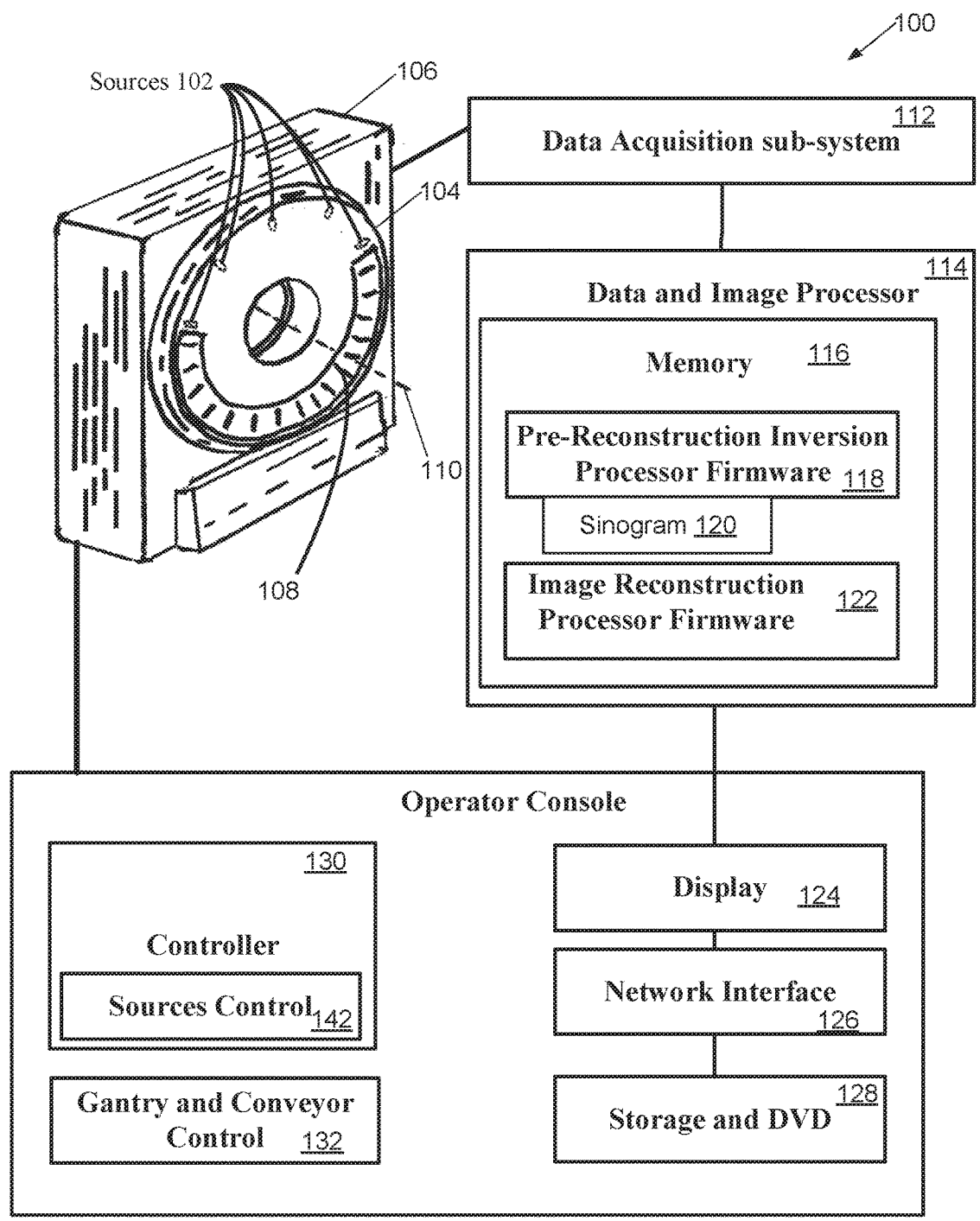
FIG. 1 is a diagram illustrating a CT system frame and gantry per an embodiment of the present invention.

The following terms are used in this invention disclosure with the specific meaning now described.

A CT system isocenter is a location, generally coinciding with the system center of rotation in the gantry central plane (defined below). It is understood that due to mechanical tolerances, vibrations, the system isocenter in practice lies within a small, mathematically defined, volume of space. It is generally located on the system rotation axis, see below.

"System rotation axis" or "rotation axis:" Generally defined as the z axis; it is the axis of rotation for gantries carrying the radiation sources, the radiation detector, or both. This is an imaginary line associated with the main rotational movement of the gantry, and generally perpendicular to the main imaging plane; the main imaging plane or gantry plane itself containing two mathematical coordinate axes for x and y, and being defined for a single-source CT system as the plane within which the source substantially rotates (if a system has several sources, it may thus have several gantry planes; the architecture will specify one of those, or yet another plane, as the main gantry plane). The intersection of the rotation axis and the main imaging plane defines the system isocenter O, c.f. above description, a mathematical point from which various system distances are measured. In case of elements being offset in z from the system central planes, their respective distances "from iso-center" are in fact measured from the system axis of rotation. Thus, their "distances" refer to distances to/from the rotation axis; or alternatively, their distances are measured in orthogonal projection on the central imaging plane x-y.

"Radiation source:" A nominally punctual, individual source of radiation useful for imaging in CT. In particular, an X-ray source; this includes X-ray sources in all their variations, from individual X-ray tube, including fixed-anode tubes, rotating-anode tubes, to individual radiation source elements in a controllable array of radiation sources, to large radiation sources that sweep a focused electron beam in a vacuum envelope to define in time a spatial excursion of a radiation focal-spot (the area from which most of the useful radiation in the beam is emitted).

"Electron beam emitter:" In this document, the term "emitter" is used to denote an electron beam emitter. The emitter may be of various types, as known in the art, including a thermionic emitter in either coiled filament (Tungsten filament, typically) or heated radiation plate; or a "cold-cathode" emitter using carbon nano-tube technology; or, a piezo or magnetostrictive electron emitter. When necessary, the emitter is understood to also have accelerating electrode(s) and focusing electrodes to specifically direct and shape the electron beam toward the anode or target.

"Emitter Ring:" In this document, the term "emitter ring" denotes the mechanical assembly that supports a plurality of emitters or emitter arrays so that the emitters are located in relative proximity to an anode or target; the emitter ring may be generally in the shape of a ring, or may substantially deviate from a ring geometry. A key feature of the designs described herein is that the emitters and the target(s) are in relative motion relative one-another, so that the electron beams generated by the emitters sweep the target(s) in time during system use. In particular, in the designs described below, the emitters and the target are always in relative motion when imaging, whether the target be fixed in the laboratory reference frame or the emitters be fixed in the laboratory reference frame.

"Fan-angle:" the angle of a projection line from the source (modeled as a point source) to the center of one cell on an array of detector cells, as measured in the central imaging plane x-y. Generally, the fan-angle is measured from the central line joining the source to the system isocenter O. Thus, an X-ray path or projection line fan-angle is relative to the source. However, in fourth-generation CT, the fan-angle is defined for a detector cell, since in that CT configuration fan-beams are acquired with vertices located at detector cell centers as a radiation source rotates around the patient.

"Imaging or measurement field-of-view (MFOV) of radius $R_M$:" the radius of a disk centered on system isocenter O such that in normal operation the full disk is exposed by one or a plurality of radiation source(s) for the acquisition of fan-beam projection(s). The radius $R_M$ in turn is related to the measurement cell that is furthest away from isocenter, in third-generation CT geometry; in fourth-generation geometry, it is determined by either the X-ray source collimator(s) lateral extents or by the timing of individual detector cells data acquisition.

"Maximum fan-angle:" For a given distance $R_S$ from the isocenter O or longitudinal system axis z to a given source, the maximum fan-angle associated with the measurement field-of-view of radius $R_M$ is given by:

$$\Gamma = \operatorname{asin} \frac{R_M}{R_S} \text{ (radians)}.$$

In a fourth-generation geometry, the source radius distance $R_S$ is replaced by the detector radius distance $R_d$ in the equation above, since projection fan-beams are formed with a given detector cell as the fan vertex.

An "axial" scan occurs when one or a plurality of radiation source(s) rotate(s) around the patient with the patient table not advancing through the gantry. Such a scan may include data acquisition over more or less than one 360-degree source rotation, as further explained below.

A "helical scan" occurs when the patient table or object conveyor belt is advanced through the gantry concurrent with X-ray source activation and rotation around the patient table or object conveyor belt.

"Full-scan:" Refers to a data acquisition mode wherein an X-ray source rotates at least 360-degrees around the patient or object to be imaged, and projection data for one particular slice in the patient are acquired over 360-degrees of view angles. In helical acquisition mode, the X-ray source rotates continuously within the gantry for an extended period (often termed "a scan"), and data for several "full-scans" are acquired in "a scan." Thus, the term "scan" by itself can be ambiguous.

"Half-scan:" In the literature, refers to a data acquisition mode where for a given slice through the object, the X-ray source rotates and data are acquired over a source angle excursion substantially equal to $\pi+2\Gamma$.

"Partial-scan:" Refers to a data acquisition mode where for a given slice through the object, the X-ray source rotates and data are acquired over a source angle excursion in the range $[\pi+2\Gamma, 2\pi]$. This is an extension of the concept of half-scan data acquisition described above.

All the above data acquisition modes may occur during a scan comprising source exposure and data acquisition from a multiplicity of rotations. In that case, the respective terms apply to the reconstruction of a specific image surface from a subset of the total "scan" projection data.

"Central angle:" The angle between two lines passing through isocenter O, and measured at O. It is convenient to specify source angles, sources separation angles, and detector angular extents, in terms of their respective central angles. If there is potential ambiguity regarding angles between lines in three-dimensional space, such as is the case when sources are offset along the rotation axis z from one-another, then the term central angle in this document refers to the angle between the lines as projected onto the main gantry plane x-y orthogonal to the rotation axis z.

"System matrix:" By linearization of the CT data acquisition problem it is possible to represent the relationship between the unknowns (object/image pixel linear X-ray attenuation coefficient values) and the measurements (projection measurements acquired by the detector) by a matrix, termed the "system matrix." By extension, applies also to systems of equations where the unknowns appear in a given non-linear form, such that by a change of variable the system could be considered linear. This will be the case in this document, where the unknown line-integrals will appear in exponential form, as given by the Beer's-Lambert law (Beer's law for short) of X-ray attenuation.

"Inverse Problem:" A problem involving the estimation of unknowns from a set of measurements, most measurements relating two or more unknowns in a single equation. The inverse problem may be linear or not.

"Matrix Inversion:" The algebraic process of determining unknowns from a set of measurements in a linear formulation of a problem.

"Under-determined inverse problem:" An inverse problem with more unknowns than measurements.

"Ill-posed inverse problem:" An inverse problem such that noise or uncertainties in the measurements are amplified through any attempt at inversion. The system matrix for such an imaging system, either as posed or as a result of linearization, then exhibits a large "condition number," as is known in the art. Computed tomography is a proto-typical example of a data acquisition modality leading to an ill-posed inversion problem, that of reconstructing tomographic images from the acquired projection data.

"Regularization:" An under-determined or ill-posed inverse problem can be regularized by the use of a-priori information about the object being imaged. That is, specific constraints are applied to the problem. For example, in CT imaging, we know the unknowns (which are the linear attenuation coefficients of the object being imaged) to be positive. Thus, we can require our inversion estimates to be positive.

A "constrained inversion problem" is an inversion problem where specific a-priori information is leveraged in the form of specific solution space constraints, in an attempt at regularizing the problem. In CT, the archetype of a constraint is that of the positivity of the linear attenuation coefficients, given that it is assumed that no significant of radiation-emitting material is present in the body being imaged.

"Tikhonov Regularization:" An exemplary regularization method used, in particular, in CT. Consider a second typical constraint as used in CT, that of minimizing (for instance, in the Euclidian norm):

$$\|Ax-y\|^2 + \delta\|x\|^2,$$

where the vectors x and y represent the unknowns and the measurement, respectively, and $\delta$ is a regularization parameter. A solution to this problem is known as a "minimum norm" solution. As is known in the art, this Tikhonov regularization problem as for analytical solution:

$$x = (A^T A + \delta I)^{-1} A^T y.$$

Because the characteristic polynomial $\det(A^T A + [\delta-\lambda]I)$ has only a finite number of roots, the regularized problem can be inverted for an infinite number of $\delta$ values. Tikhonov regularization applies more generally to a wide variety of constrained inversion problems, as is known in the art. Regularization methods other than Tikhonov are known and apply to the designs proposed in this document.

"Primary beam:" The fraction of an X-ray beam transmitted through an object without deflection, scattering, or absorption.

"Scattered radiation:" any X-ray radiation that has undergone a deflection/scattering event with respect to its original straight-line travel path.

"Simultaneous exposure:" In the context of this disclosure, simultaneous exposure occurs when two or more X-ray/radiation sources are simultaneously active and irradiating the patient/object to be imaged.

"Simultaneous exposure of an individual detector cell:" In this document, simultaneous exposure of an individual detector cell occurs when two or more X-ray sources are simultaneously active and their projections overlap on at least part of the detector; that is, at least one detector cell is being impinged by primary beams from two or more X-ray sources. In the following, the term "simultaneous exposure" is also used with this meaning when there is no risk of confusion.

"Radiation source array:" A plurality of individual X-ray sources provided as a single sub-system. In specific cases, the individual X-ray source elements within the array can be addressed or controlled individually.

"Activated (pertains to a radiation source):" The radiation source is energized and is ready to produce a radiation beam. For example, in a conventional X-ray tube, the filament may be heated by a current and electrons "boiled off." However, the electron beam to the anode may be cut-off or pinched off by an applied voltage, so that the amount of emitted radiation is either non-existent or very small. So an activated radiation source may emit a radiation beam or not, and may be turned "on" or "off" with respect to X-ray beam emission quickly (that is, in a few microseconds).

"Detector," also "radiation detector:" Refers to the subsystem comprising the entirety of radiation measurement cells; each of these cells gives rise to a measurement at specific time intervals ("time sampling intervals") and is referred to as an "individual detector cell." Detector cells may be arranged on a variety of surface configurations; all the cells in a detector do not need to form a contiguous surface. A detector may include several components, such as separate detector arrays. For illustration, in some configurations, a component of the detector is rotating on a gantry, and another component of the detector is fixed in the laboratory coordinate system. In photon counting detectors, a cell generates a signal each time an X-ray interacts within the cell. In this document, it is understood that the detector array may have several rows, generally the rows being offset from one-another in the direction of the system rotation axis z (or more generally a two-dimensional array in any spatial configuration—not necessarily with rows orthogonal to z, etc.). In the document, it is referred to a "detector arc," meaning the curve that represents the trace of the detector surface as it intersects the main gantry plane x-y. The detector arc, as any curve in three-dimensional space, may have a curvature center. The curvature center may vary locally along the arc, as is the case when the arc is not an arc of a circle.

"Central ray:" A mathematical line from the mathematical, nominal center of a radiation source to the detector passing through the system isocenter O, as projected onto the central imaging plane x-y.

"Gantry:" Mechanical apparatus supporting a rotating source, array of sources, or plurality of sources, and optionally one or a plurality of detector(s), as well as other system components as known in the art.

"Drum:" Part of a gantry, a drum is a mechanical device that rotates around the patient or object to be imaged in CT. Thus, a CT system may present one or more rotating gantry/drums. Synonym for "rotating gantry component."

"Image reconstruction:" The CT inverse problem of recovering the object linear attenuation coefficient spatial distribution from a set of projection measurements. It is understood that, although the process of image reconstruction typically yields one two-dimensional cross-sectional image of the object, it in fact performs a three-dimensional attenuation map reconstruction, since the process of two-dimensional reconstruction starts by selecting a plane or surface of interest within the three-dimensional object, then continues by selecting projection data associated with this surface ("sinogram") and then performs the tomographic reconstruction itself. Further, successive tomographic slices are typically processed in sequence. In the sense that the data for a given slice is associated to a particular time interval, the CT reconstruction in effect reconstruct a slice of a four-dimensional volume (where one reconstructed three-dimensional volume corresponds to a "snapshot" of the living body in a given time interval). The three-dimensional reconstructed image, or attenuation map, is represented on a set of volume elements, or voxels.

"Projection:" A set of measurements normally associated with a source at a given nominal position with respect to the object. In CT, a given projection is considered complete if substantially all mathematical lines from the source through the measurement field-of-view MFOV are substantially traversed by an X-ray beam and give rise to a detector measurement. Also called a "view." The term projection is also used to denote the mathematical set of lines originating at a source, passing through the MFOV, and impinging on the detector; whether or not actual radiation beams are emitted by the source. In practice, a projection is acquired over time, and if the source moves then the nominal position is defined as the center of the motion trajectory or other reasonable point with respect to the data acquisition scheme.

"Fan-beam projection:" In third-generation CT, projections are acquired at a given nominal time in the form of a fan of rays emitted by a source, irradiating the measurement-field-of-view, and then impinging on a detector. In any practical implementation, a fan-projection is acquired during a finite time interval, called the "detector integration time," whether the detector be of photon-counting type or not.

"Projection ray:" Geometrically, a line from one punctual radiation source to the punctual center of an individual detector cell at a given time.

By extension, a projection ray: the geometric envelope of the lines originating from one point on the X-ray source focal spot and ending on the radiation-sensitive surface of an individual detector cell at a given instant in time. Thus, a projection ray in this sense is a beam around a center line with a limited three-dimensional spatial extent and a cross-section area in a plane orthogonal to the projection ray above defined. By extension, a projection ray corresponds to the envelope of the X-ray paths extending from the entire active focal spot area on the X-ray source to the entire active detector cell area, at a given instant in time. To each such projection ray through the object is associated a line-integral of the object linear attenuation coefficients.

By extension, a projection ray: corresponds to the total three-dimensional volume obtained when the three-dimensional beam envelope described above corresponding to one instant in time is swept during an integration time corresponding to the acquisition of one detector cell sample. To such a projection ray is associated a "line-integral" of the object linear attenuation coefficients, a measurement at the detector, and by slight abuse of language, a geometric line through the object under imaging investigation.

"Line-integral:" The measurement associated to a single projection ray (single straight-line path through the MFOV) in a CT system. A projection typically comprises several hundred line integrals; and a complete data set (see "sinogram") for one image to be reconstructed typically comprises several hundreds of projections worth of line-integral data. The line-integrals form the input to the image reconstruction methods/process—independently of the specific of the image reconstruction algorithm; that is, all CT reconstruction algorithms take as input the line-integral data, also referred in this document as the "individual line-integral" data, as opposed to the summed projection data that are directly acquired by the radiation detector in embodiments described herein. A line-integral L refers to an integral of attenuation coefficients over a projection ray volume; and the description below by abuse of language also uses the term line-integral to refer to a geometric path through the object, or a single line associated with the projection ray, understood to correspond to the individual line-integral measurement.

"Detector quarter-offset:" A system configuration whereby by offsetting the detector such that a central ray from a source intersect a detector cell nominally at ¼ or ¾ of its width, the conjugate ray of a given line-integral L—acquired after substantially "180-degrees gantry rotation" (the actual gantry rotation being dependent on the ray fan-angle as known in the art)—will be sampled that is parallel and laterally offset from L by about ½ of the detector width. This enables the acquisition of sinogram data sets with higher spatial resolution in the plane or surface of reconstruction. Conversely, the quarter offset can be ignored and the conjugate ray considered to provide a second estimate of a line-integral L. Similar sampling effects are achieved by deflecting the electron beam focal spot on the X-ray target, either magnetically or electrostatically; or by offsetting a plurality of sources from nominal positions that would ensure substantial sampling of the same lines. This offsetting can be leveraged in multisource CT designs described herein to achieve a substantial increase in spatial resolution.

"Summed projection data," or "summed line-integrals:" In the CT systems described herein, some line-integrals may be measured individually; but most line-integrals are measured in sums; that is, a given detector cell measurement is associated to radiation having travelled along a plurality of paths/projection rays originating from several radiation sources and ending on one detector cell at a given time/time-interval. It is thus necessary to examine conditions under which the individual line-integral data may be estimated from the summed line-integral data, as is required for image reconstruction by most or all known CT reconstruction algorithms. This document describes CT systems that lead to summed data from which the individual line-integral estimates may be recovered, and methods of doing so. This necessarily implies solving an inverse problem.

Thus, the systems and methods of the present document are concerned, at least in part, with the setting and solving of a "pre-reconstruction inverse problem." As is described in the document, specific CT system designs lead to conditions that are favorable to the solving of this problem. The pre-reconstruction inversion problem works with the summed measurements as inputs and provides as output estimates for the individual line-integral measurements that are themselves the inputs to the CT image reconstruction process. In particular, in this document two types of situations are outlined: "local pre-reconstruction inverse problem" and "global pre-reconstruction inverse problem." By local, it is meant that individual-line integral estimates can be obtained by solving, for each line-integral L, a system with $N_m$ or fewer rows, where as described below $N_m = N_m(N_S, \Delta\theta_S, R_M, R_S, R_d, \theta_a)$ is the number of measurements pertaining to the L-bundle of L; typically, a much smaller number (e.g. 3 to 3,000) than the number of measurements in a sinogram (e.g. 1,000,000), as described in this document. By contrast, a global pre-reconstruction inversion is one that operates on substantially all of the sinogram data set associated with one image to be reconstructed to obtain any individual line-integral estimate. CT image reconstruction is an example of a "global inverse problem."

"Line-integral bundle," or "L-bundle:" In the CT systems of the present invention, often measurements of one specific line-integral over a specific projection ray/geometric line involve other line integrals (and associated geometric lines/projection rays), through the summed projection data process described above. In specific embodiments, for a system having $N_s$ radiation sources, over a partial system rotation, $N_m$ or fewer summed measurements will involve a particular line-integral L and associated geometric lines/projection rays through the object. To each such measurement is associated a set of up to $N_s-1$ other individual line-integrals and geometric lines/projection rays through the object. Thus, the set of all individual line-integrals and geometric lines/projection rays through the object associated through summed measurement with line L is described as the "L-line-integral bundle," or line-integral bundle for short. Since each individual line integral is associated to an unknown, the L-bundle corresponds to a set of unknowns that can be recovered/estimated through a pre-reconstruction inversion process. To each L-bundle is associated a corresponding set of equations, the solution of which provides estimates for each of the individual line-integrals associated with the summed measurements for the L-bundle.

A source-based fan-beam projection is "truncated" if some rays in the projection that intersect the imaging field-of-view do not lead to a measurement; this does not include the effect of X-rays falling on an anti-scatter grid element or septa separating two radiation-sensitive cell areas on the detector.

Conversely, a source-based fan-beam projection is "untruncated" if all projection rays intersecting the imaging field-of-view lead to a measurement. Similar definitions apply for detector-based fan-beam projections.

Sinogram (single row and multi-row detectors):" A sinogram is a set of projection data associated with a given slice or tomographic surface through the object, or by extension to a volume through the object for which tomographic information is sought. The sinogram is thus the data set used by a given CT image reconstruction algorithm to generate a tomographic image in a pre-selected slice of interest. In CT, it is often arranged as a set of views/projections, each projection including a set of detector cell measurements. A typical medical CT sinogram contains several hundreds (about 1,000) views or projections, each projection containing several hundred measurements (about 1,000 as well). During a typical scan, projections data sets are acquired that can be re-arranged/re-organized into sinograms in a number of ways, including through the processes of rebinning and interpolation (from detector row-to-detector row; projection-to-projection; detector column-to-detector column) as known in the art. In this document, the term sinogram is associated to the set of data that will be used for the reconstruction of a specific tomographic image. By extension, the term sinogram in this document is also used to denote the set of geometric lines for which projection measurements are acquired. The expression "(a line) L in the sinogram" then means that the geometric line L is associated to a measurement for which an estimate is sought (to be recovered from summed measurements) for the sinogram under consideration. Similarly, the term L-bundle, defined as a set of geometric lines, can also be understood to be a set of summed measurements involving specific geometric straight-lines in the L-bundle.

"Detector distance:" In this document, the term "detector distance" means the smallest (minimum) of the distances from the system isocenter O to the detector surface along the central rays from the various sources to the detector surface.

"Flying detector:" In this document, a "flying detector" is a detector mounted on the inside surface of a rotating gantry; the rotating gantry being generally cylindrical in shape and centered on the system isocenter O and/or the system longitudinal axis z. In operation, the flying detector rotates inside a second gantry that supports a plurality of radiation sources. The flying detector comprises an extended aperture of dimensions such that X-ray sources arranged on the gantry external to the flying detector can illuminate therethrough over a central angle substantially equal to $(\pi-2\Gamma)$ radians; therefore, depending on the geometry of the system, and the dimensions of the outer gantry supporting the sources, the actual aperture dimension may differ to some extent from the nominal $(\pi-2\Gamma)$ radians; this aperture is referred to as the "extended flying detector aperture" or "extended aperture" for short. The outer gantry, supporting the X-ray sources, may be either rotating or fixed in the laboratory reference frame (if it rotates, it can rotate in either direction with respect to the flying detector rotation direction). The flying detector has active detector cells distributed over a central angle substantially equal to the extended-aperture complementary central arc in $2\pi$ radians, that is $(\pi+2\Gamma)$ radians. The flying detector may have one or a plurality of detector cell rows, generally arranged along the z direction (although this need not be the case: for example, a two dimensional Cartesian array of detector cells could be arranged at an angle with respect to the central imaging plane x-y). It may have other elements as known in the art, including anti-scatter-grids (ASGs); the ASGs lamellas may be arranged in a direction generally parallel to the central imaging plane defined by axes x and y. The flying detector may include indirect or direct radiation detection elements as known in the art. Also called "flying detector gantry/drum."

A radiation source is said to be "in view of the detector" or "visible from the detector" if it is activated, and such that when the source is not muted (as by electron-beam pinching as described above) some of the fan-beam of radiation originating from the source, exiting the source collimator, and intersecting the imaging field-of-view, impinges or would impinge on the surface of radiation detector (whether on a radiation detection element, an ASG lamella, or another component of the radiation detector). That is, the corresponding projection is un-truncated. In the context of a system with a flying detector, this implies that rays from such a source passing through the MFOV is not blocked by flying detector components other than the entrance surface of the radiation detector. It is understood that there is a short transition time during which a subset of the mathematical lines from the source through the MFOV are blocked by the flying detector.

"Source distance:" In general, the radiation sources will be positioned on a gantry, either rotating or fixed, at substantially the same distance from isocenter. However, in specific designs, this distance may vary from source to source; in particular, should radiation source arrays be generally arranged on flat surfaces, then the distances from the various individual source elements to O (or to the rotation axis) will vary slightly. More generally, it may be desirable to position the sources at position offsets with respect to their distance to O (or to the longitudinal system axis z). In the claims, the term "source distance" and the variable $R_s$ means the smallest (minimum) of the distances from the system isocenter O to the radiation sources focal spot centers along the central rays from O to the respective radiation source focal spot centers.

"System fan-angle ($\Gamma$):" Similarly, since the maximum useful fan-angle is generally associated to the radius of the measurement/imaging field-of-view $R_M$ and to the source distance, to each source corresponds a maximum fan-angle value $\Gamma$ as previously described. In this document, by system fan-angle or Greek letter $\Gamma$ it is meant the largest of these fan-angles, associated with the one source the closest from isocenter; in other word, is defined by $R_M$ and the source distance $R_S$ defined above; Thus the system fan-angle is given by:

$$\Gamma = \operatorname{asin}\left(\frac{R_M}{R_S}\right).$$

Naturally in a fourth-generation-like architecture, the definition is:

$$\Gamma = \operatorname{asin}\left(\frac{R_M}{R_d}\right).$$

In this document the symbol F refers to the source system angle, unless otherwise specified.

In a system with a single rotating gantry/drum, the "Extreme sources angle" $\theta_s$ is the central angle between the two extreme sources in a set of $N_s$ sources arranged over a central angle generally less than $(\pi-2\Gamma)$ radians on a rotating gantry, whether the sources be equispaced or not. In a preferred embodiment, the sources are equidistributed in central angle over a central angle less or equal to $(\pi-2\Gamma)$ radians. In a system with one or two rotating motions (one for the sources and one for the detector), and in particular in a system with a flying detector, and either a rotating source gantry of a fixed source gantry supporting a large number of sources, the extreme source angle $\theta_S$ represents the central angle between the two extreme sources in view of the detector (defined above) at a given time t through the flying detector extended aperture. Thus in principle, the extreme source angle can vary with time, $\theta_S=\theta_S(t)$ . . . In general, a dual-drum CT system will have $N_s$ sources, a subset of $N_a \geq K$ sources at a given time being in view of the detector and defining an extreme source central angle $\theta_S=\theta_S(t)$. Thus, in general it is desirable to distinguish between the system number of sources $N_s$ and the number of sources in view of the detector at a given instant, $N_a$. Accordingly, $N_a$ is the number of sources in view of the detector through the extended detector aperture (when applicable) of central angle $\theta_a$. These $N_a$ sources present a central angle $\Delta\theta_a \leq \theta_a$.

When the sources are equispaced, the angle $\Delta\theta_s$ represents the central angle between two adjacent sources. If the sources are populating a set of physical points on the source ring/gantry equidistributed in central angle, then the angle $\Delta\theta_s$ represents the minimal central angle between two adjacent sources. This is a situation that occurs when the sources are arranged in groups, the sources within a group being separated by a central angle substantially equal to $\Delta\theta_s$, the sources in different groups being separated by a central angle that is substantially an integer multiple of $\Delta\theta_s$. In this document, the description is given assuming the radiation sources are populating a set of points arranged on a single grid equidistributed in central angle $\Delta\theta_s$. It is understood that the designs described therein apply as well if the radiation sources are populating a plurality of point sets distributed according to several central angle intervals $\Delta\theta_{s,i\ i=1,\ldots M_g}$. In such a situation, the cardinality of the L-bundle for any line L through the measured field-of-view may increase in proportion to the number of central angle grids $M_g$. This is of particular interest to achieve increased spatial resolution with the system designs of the present document.

A set of $N_S$ radiation sources is said to be "partially overlapping" if the projections associated with adjacent sources, virtual or actual radiation projections, overlap at least partially on at least part of the detector. Thus, when radiation sources are partially overlapping, at least a subset of the detector cells would give rise to summed line-integral measurement(s), when X-ray beams are emitted by the partially overlapping ("overlapping" for short) sources.

"Source modulation:" By source modulation in this document it is meant spectral modulation, as well as modulation of other source parameters, such as focal spot size, polarization, and other relevant parameters. Specifically, with respect to spectral source modulation, it is meant any change in the function defining the radiation amplitude distribution at each frequency; including the definition of the spectral function support—that is that range of frequencies where the radiation source output cannot be considered so small as to be negligible. Spectral distribution changes can be effected in practice by changes in tube current measured for example in milliamps ("mA"), applied peak-kilo-voltage (kVp), choice of target material, choice of beam filtration.

"Bearings:" In this document designs are described that involve the rotation of one or a plurality of gantries, drums, or mechanical assemblies. These rotation motions are enabled by bearings, as is known in the art. In the document, the term bearings is understood to refer to any of a mechanical bearing (such as a ball bearing, for example); a magnetic bearing (such as magnetic levitation bearings, with either attractive or repulsive poles); an air bearing (enabled by air pressure without direct solid surface contact during operation: for the detector gantry/drum); and generally, any bearing method suitable to enable rotations per the designs described.

In this document, the description emphasis is placed on solving a pre-reconstruction inverse problem, followed by image reconstruction. It will be understood by those skilled in the art that the two inversion problems can be formulated together as a "combined inversion problem." This is in particular the case when both inversion problems, pre-reconstruction and reconstruction, are to be solved using algebraic and/or iterative methods.

In this document, the terms "asin" or "asine" refer to an Arcsine function, an inverse of sine function. More specifically it refers to the inverse of the sine function with range −90 degrees to 90 degrees.

"Conjugate gradients:" The document refers to various methods of solving a system of equations. One such method is that of conjugate gradient (CG), as known in the art. CG efficiently solves a sparse system $Ax=y$ for A symmetric definite positive, and can be extended to more general matrices A. It involves computing gradients and seeking search directions, and is known to be effective for CT and related inverse problem computations.

"Multispectral imaging:" Multispectral imaging refers to the imaging of the same object/patient by various beam spectra. Multispectral imaging can be implemented, as is known in the art, temporally by exposing a given volume by two beams either obtained from two or more sources or from one source at different times, or by using a detector filter and a single exposure. Generally, parameters that enable beam spectral shaping include source peak-kilo-voltage, source electron beam current, source target material, and source/pre-patient beam filtration. All of these methods and techniques apply to the designs presented in this document, as will be apparent to those skilled in the art.

"Dual rotation:" The designs described in this document rely on relative motion of the electron-beam emitters with respect to the target(s). They can be implemented using a single gantry rotation, dual-gantry or dual-drum designs, and/or a combination of gantry rotation and target rotation within a vacuum envelope. In specific designs, one or two assemblies are rotating within a vacuum envelope. In specific designs, a detector gantry/drum is rotating within a volume defined by the vacuum envelope surfaces at shortest distances from the system rotation axis, either at the same or at a different angular velocity than the emitter support structure.

"Dual annular ring:" In this document, refers to a radiation generation subsystem presenting a shared annular ring target and an emitter structure supporting a plurality of emitters facing the shared target, the emitter structure having generally an annular structure.

The description below assumes clockwise system rotation, for both the detector and the source ring when applicable; actual system rotation can be in either direction. In particular, when relevant, the source drum/ring and detector drum can rotate in opposite directions; as well as in the same direction (in different scans performed by a system).

The System

Before proceeding with the detailed description, it should be noted that the matter contained in the following description and/or shown in the accompanying drawings may be embodied in various forms, and should therefore be interpreted as illustrative, and not in a limiting sense. Elements shown in the drawings are not necessarily to scale and may be exaggerated, enlarged or simplified, to facilitate understanding of the invention.

The invention applies to various CT and digital tomosynthesis imaging configurations. In an imaging situation, it is desirable for the radiation source(s) to have the attributes described below. The ideal form of these attributes is considered unachievable; however, it is an aim of scientific and technological advances to approximate those conditions as closely as possible. Since X-ray imaging works in projection, the spatial resolution of the observed image is uniquely defined by the paths from the source focal spot or surface area to the various detector elements. It is thus desirable that the X-ray source be a point source, or at least of as small as possible a spatial extent as practical; source blurring (made worse in specific geometries by magnification) typically contributes a limiting factor to the overall system resolution performance.

Further, ideally the X-ray source should have as high power as possible. At least three factors lead to this requirement. First, and as mentioned above, it is desirable for the source area to be as small as possible, therefore leading to high power per given area. Second, temporal resolution requirements lead to the use of a short exposure time—typically to avoid or reduce effects due to contrast, patient or organ motion during an exposure. Third, X-ray radiation is broad-band in nature, but optimally a specific X-ray energy (or narrow energy band) could be specified as a function of object attenuation in the beam path; while tuning the source to that specific frequency, or at least to a narrow frequency band containing the desired frequency, is currently not achievable commercially with practical sources, it is possible to filter the beam to at least remove a significant part of the radiation below that specific frequency or frequency band. However, filtering also reduces the beam output within the desired frequency band.

In X-ray imaging, useful radiation—radiation such that the object to be imaged is semi-transparent to it—is typically obtained by bombarding with high energy electrons a target material in an anode. High Z materials are preferred as they provide more intense radiation. The resulting broadband frequency radiation, "bremsstrahlung" or "braking radiation," typically contributes the largest radiation energy out of the target, although specific materials such as Rhenium (Rh) and Molybdenum (Mo) have marked K-edge radiation peaks corresponding to K-shell atomic transitions. By far, the material the most commonly used for anode targets in X-ray medical imaging and security or inspection imaging is Tungsten (W).

The spectra obtained as a result of target electronic bombardment has a maximum emission energy defined by the maximum energy of the impinging electrons, which in turn is set by the peak-kilo-voltage (kVp) applied to the tube or source. The lowest energies are a function of a tube self-filtration resulting from, in part, the material used to define a functional tube vacuum envelope; typically glass or metal. In medical imaging, it is common practice to provide an additional layer of filtration immediately in front of the source (on the X-ray paths toward the patient and then the detector) to eliminate or at least significantly reduce the intensity of low-energy X-rays. This is done because those low energy X-rays have low penetration power and in most applications contribute primarily to the patient dose (such as in skin dose), but very little to observed signal. X-ray attenuation of a thin monochromatic (energy E=hv where h is Planck's constant and v the frequency of the emitted monochromatic radiation) pencil beam through a (thin) slab of thickness l and attenuation $\mu(E)$ follows Beer's law of attenuation:

$$I(E,l,\mu)=I_0(E)\exp(-\mu(E)\times l),$$

where $I_0=n_0 \times E$ ($n_0$ number of photons emitted at energy E) is the intensity that would be measured without any object or patient in the beam, or intensity of the object impinging beam along the specific pencil-path, and I is the exiting beam intensity (at single energy E). So $I_0$ in this equation refers to the intensity that a detector would measure in the absence of any object in the beam path.

Throughout this document, it is understood that various sources among a system's multiplicity of radiation sources may emit radiations of various spectral properties and with various focal spot intensity distributions. The various spectral properties come from, as is known in the art in the case of X-ray sources, choices of target material, tube current (mA), peak kilo-voltage (kVp), and beam filtration. The focal spot spectral and intensity distributions vary depending on the beam properties of each source. Thus, for example, a subset of the system sources may be operated at a given kVp, beam current, and beam filtration, and a second subset at another kVp, beam current, and beam filtration. Many combinations are possible.

Up-to-now, simultaneous exposure of the same detector cell, or set of detector cells, by multiple radiation sources, has been generally avoided in scientific, commercial and medical electro-magnetic applications that rely on transmission imaging through a semi-opaque medium and direct image formation (without an optics forming element such as a pin-hole, lens, or combination thereof). In such a setting it is a-priori difficult or impossible to separate the signals due to the respective sources since in the absence of a lens, the imaging geometry is uniquely specified by the lines joining the sources and a given detector cell; the radiation from one source typically reaches the entirety of the useful detector array; indeed under "ideal imaging conditions" the exposure intensity from one source (without intervening object) would be uniform across the useful detector array. Accordingly, simultaneous exposure of an object onto a common set of detector cells leads to commingling of the detector signals where the X-ray projections from the two or more sources overlap; with no a-priori means to separate the summed projection signal into the various constituents that are to be associated with each of the simultaneously active sources. Thus, simultaneous exposure with projection overlap is not applied in current state-of-the-art X-ray or CT imaging.

As a result, in a setting where multiple radiation sources are "in view" of the detector, and where it may be desirable to leverage the multiple sources—for instance for flux or power reasons, a multiplexing approach that relies on temporal, spectral multiplexing, or an approach combining several of these elements is first considered.

Multiplexing the sources, however, typically restricts the maximum flux available from the respective sources: Temporal multiplexing pulses the sources and limits emission of a given source to the time when that source is turned on. Spectral multiplexing limits a given source output to a given energy band, either intrinsically within the source or by external radiation filtration. In either case, the total source output is considerably reduced, and thus the main impetus for having two or more sources simultaneously in view of the detector is not met.

In CT, temporal resolution gains are achieved by increasing the source rotation speed around the object. However, this imposes source output power requirements that are difficult to achieve, since the X-ray source output must increase in direct proportion to the source rotation speed increase to maintain a given level of X-ray flux, and thus signal-to-noise ratio, per view/projection and per tomographic slice to be reconstructed. In this document novel CT system architectures are proposed that rely on the simultaneous exposure of at least part of a detector array by several radiation sources to break through the flux limitation and achieve higher temporal resolution (GM Besson, Medical Physics 42, 2668 (2015); doi: 10.1118/1.4918328). Alternatively, those architectures, and the architectures of the present document, can be leveraged to image at higher spatial resolution by distributing the required power between the multiple sources contributing to the imaging.

Indeed, in all X-ray applications, including projection imaging and CT, it would be desirable as described above to have access to sources of arbitrary power. Since any individual source is necessarily limited, it is desirable to leverage several sources and their combined power under simultaneous exposure conditions. This could range in principle from the use of two sources to implementations with arrays comprising a large number of individually addressable sources.

Arrays of individual X-ray source emitters are now becoming possible, and some such technologies are in the prototype stage. XinRay Systems (7020 Kit Creek Rd #210, Durham, N.C. 27560) has developed linear arrays of individually addressable sources (http://xinraysystems.com/), utilizing proprietary carbon nanotube based X-ray sources. U.S. Pat. No. 8,755,493 discloses piezoelectric or pyroelectric crystals capable of generating high-energy electron beams and thus X-rays; the technology is potentially available to form an array of point sources. Tribogenics (5440 McConnell Ave, Los Angeles, Calif. 90066; http://tribogenics.com/) has developed an alternative way to emit high-energy electrons that may also be amenable to the design of arrays of X-ray sources.

Moving or rotating the source around the patient as required in CT imaging with a single source, also limits achievable temporal resolution for mechanical design reasons. High-power conventional X-ray sources currently in CT systems implement a rotating anode approach; the rotating anode being placed in vacuum envelope, or tube, which itself rotates in the gantry around the patient or object to be imaged. Large power requirements lead to large anodes and tube sub-systems, and high angular velocity gantry rotations places significant mechanical strain on all rotating components.

In alternative embodiments, two or more X-ray sources, or arrays of sources, are mounted on a gantry; the gantry moving with respect to the patient. Use of multiple sources reduces the range of mechanical excursion required for a complete data acquisition for any tomographic slice or set of tomographic slices to be reconstructed; in the case of array(s) of sources, it may even alleviate the motion requirement in part or completely. These approaches thus potentially help improve temporal resolution. Also, they provide practical ways to perform multispectral imaging of an object; for example, by allocating sub-sets of sources to each spectrum to be used in the multispectral data acquisition.

Thus, simultaneously irradiating the patient or object to be imaged by two or more X-ray sources is desirable. Further, it is desirable to obtain this capability while active source projections overlap on the detector; otherwise, simple geometric considerations limit to about three the maximum number of sources that are simultaneously active without projection overlap in a typical medical CT geometry.

To achieve these aims, the present document describes a novel multi-source CT system architecture wherein several electron-beam emitters (cathodes) face a common, shared (anode) target and are moved with respect to the shared target surface The document also presents a general method or algorithm to recover the individual line integral projection data from combined (summed) data obtained with simultaneous radiation exposure, in the general case of a CT system comprising K simultaneously active radiation sources and performing a complete or partial ("half-scan" or "partial-scan") revolution around the patient or object to be imaged.

In the general situation where a CT system comprises K simultaneously active sources, specific methods are presented to regularize the pre-reconstruction inversion and recovery problem in specific imaging conditions. These specific imaging methods rely on the use of radiation source modulation in time to encode information associated with each one of K simultaneously active radiation sources; the projection data associated with each individual source is recovered through correlation analysis of the summed projection data; or using correlation as an a-priori constraint on the recovery problem; or by the inversion of regular matrix presenting favorable numerical conditioning.

A multiple-source CT scanner system 100 (FIG. 1) as described herein has multiple radiation sources 102, which in a particular embodiment comprise a multiplicity of cathodes or electron beam emitters facing a common, shared anode target. In another embodiment, the multiplicity of electron beam sources are arranged in arrays facing a common, shared target. The electron beam sources 102 are mounted on a rotatable gantry 104 located within a generally toroidal vacuum envelope itself mounted in a frame 106. In operation, a subset of the electron beam emitters is active, emitting electron beam(s), and the electron beams impinge on the shared target, which may also be mounted on a separate, rotatable gantry within the vacuum envelope; at each electron beam impingement area on the shared target, a beam of X-ray radiation is generated. Rotatable gantry 104 has a cylindrical passage in which a patient or object to be scanned is positioned on a movable table or conveyor (not shown) that passes through the passage. The cylindrical passage has an axis 110 the intersection of which with the main plane of the gantry is known herein as the isocenter O of the system. Axis 110 coincides with the gantry(ies) rotation axis. A radiation detector array 108 is mounted to receive radiation emitted by sources 102 that may have traversed through the patient or object in the passage. In some embodiments, the detector array is mounted to the frame, as described herein; in some embodiments described herein, the sources and the detector are mounted on separately rotatable gantries, rotating at either the same or different angular velocities. Detector array 108 is coupled to provide radiation detection measurements through a data acquisition subsystem 112 into a processor 114. Processor 114 has a memory system 116 that contains an inversion firmware 118 that processes detector data into a sinogram 120 through the pre-reconstruction inversion process described therein. Memory 116 also contains an image reconstruction firmware 122 that constructs tomographic images of the patient or object to be scanned; the tomographic images may be viewed on display 124, uploaded via network interface 126 into an electronic medical records system (not shown) or radiological database, or written onto DVD's for physical record storage, radiologist review, or transfer to other facilities. Gantry(ies) 104, radiation sources 102, and data acquisition 112 all operate under control of a controller 130 and gantry & conveyor control 132. Controller 130 also contains specific firmware 142 for the control of the various radiation sources parameters during a scan.

Figure 2:
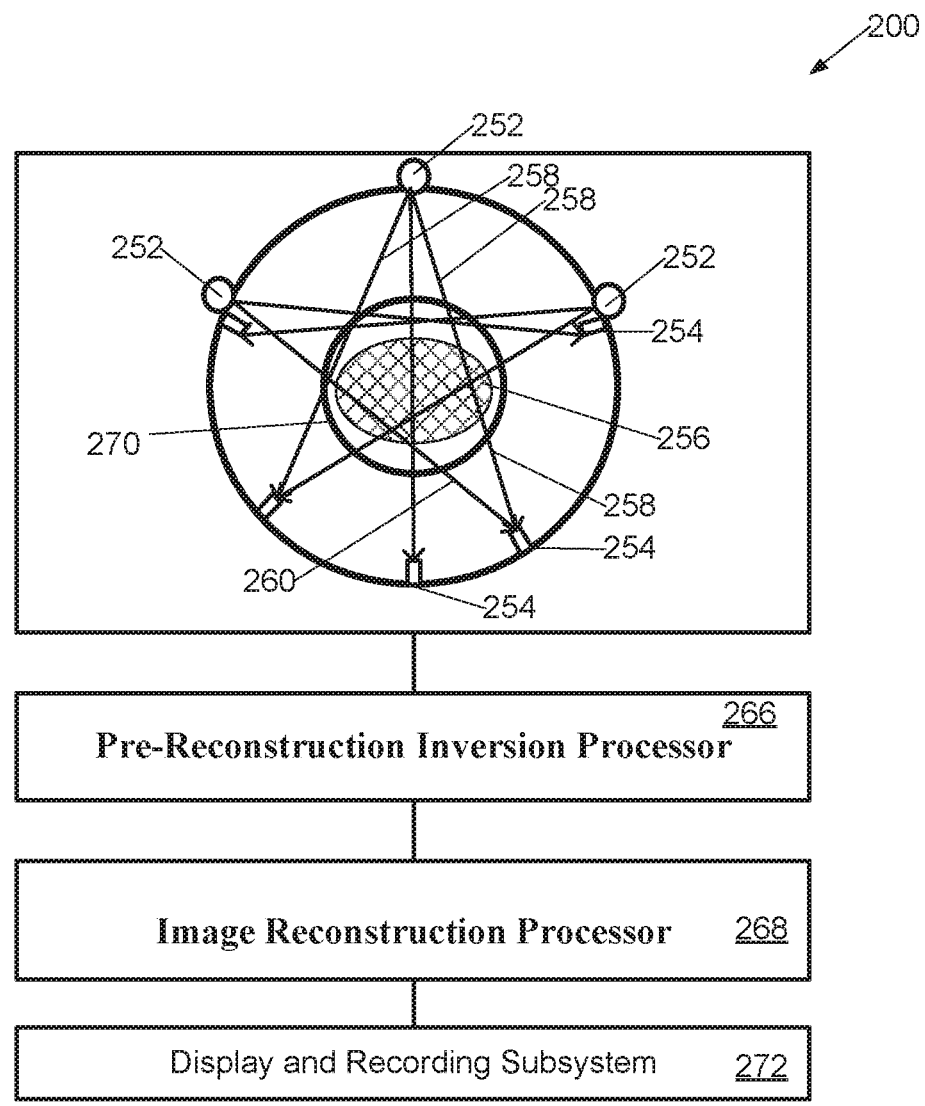
FIG. 2 is a schematic representation of the CT system of FIG. 1.

System 100 is representable schematically as illustrated in FIG. 2, 200, where a subset of the set of radiation sources 252 are represented as circles and specific individual detector elements 254 of the radiation detector array(s) are represented as rectangles. In a typical embodiment the radiation detector presents a substantially continuous surface to impinging radiation in such a manner that direct lines from the source(s) through the patient intersect it. The patient or object to be scanned 256 is located such that at least some lines 258, 260 drawn from radiation sources 252 to radiation detector elements 254 pass through the patient or object 256. When radiation sources 252 are active, X-ray radiation passes along each line 258 to the detector elements, and some of the radiation is absorbed by patient or object 256; attenuation along each line is a line integral of attenuation coefficients at multiple points in the patient or object 256 along the line as further described therein. Each detector element receives a signal that represents a sum of radiation along each line (and thus a function of each line integral of attenuation coefficients) 258, 260 from active radiation sources that illuminates that element 254. Signals from detector elements 254 are passed to the pre-reconstruction inversion processor 266, which is implemented as inversion firmware 118 in memory 116 executing on processor 266 to provide sinogram data to a reconstruction processor 268 implemented as reconstruction firmware 122 in memory 116 executing on processor 268 to provide images. In alternative embodiments, the pre-reconstruction inversion and reconstruction are implemented by separate firmware routines in a common image processor.

Figure 3:
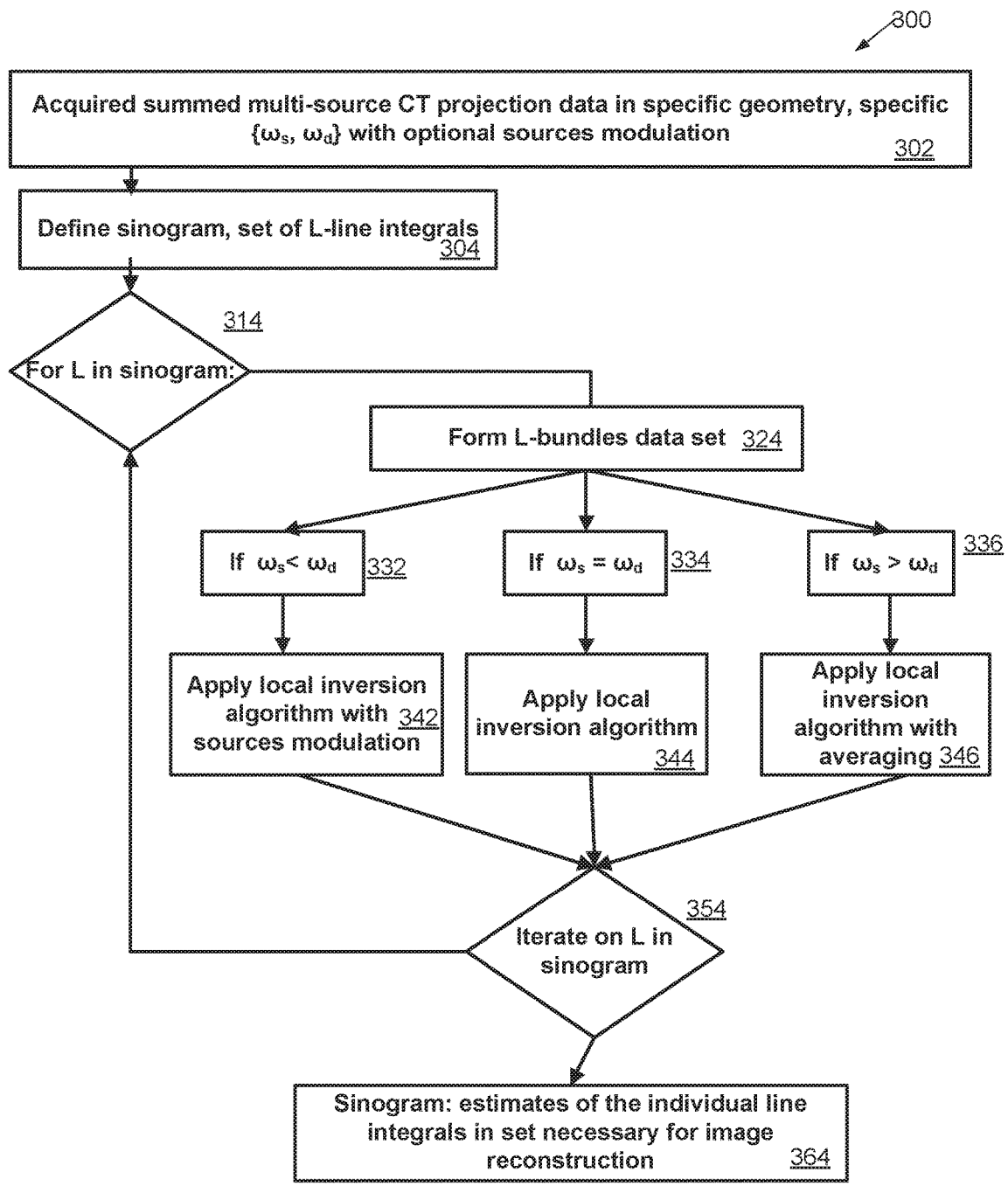
FIG. 3 illustrates in flow-chart form tasks performed by the pre-reconstruction inversion processor.

Specific tasks performed by pre-reconstruction inversion firmware 118 are illustrated in FIG. 3, 300. Since, in CT scanning systems of the present invention, projections from two or more radiation sources 252 may overlap on detector array 108, meaning that one or more radiation detector elements 254 receives direct un-scattered radiation from two or more of sources 252, the line integral signal contributions from each source as received at the radiation detector elements 254, 264 must be separated to produce a sinogram, or estimate of the line-attenuation integral over each geometric line individually, that can be processed with conventional image reconstruction firmware 122. In order to do so, and given a CT scan acquisition performed under specific parameter values, the inversion firmware 118 determines a set of geometric lines L (and associated projection attenuation measurements, i.e. sinogram 304: set of line-integral measurements or estimates necessary for tomographic reconstruction of one image) for which individual measurement estimates need to generated for conventional image reconstruction to proceed. Generally, these lines correspond to lines 258, 260 associated with paths from each radiation source 252 and each radiation detector element 254 although in specific embodiments the two sets may not correspond exactly, but only approximately. For instance, in one embodiment, the set of lines acquired in summed measurement is, as described below, a super-set of the set of lines needed for image reconstruction. Those lines L associated with each detector element 254 are grouped into a "L-Bundle data sets 324" or groups of related lines, such that a given measurement at a detector cell under consideration may involve one or a plurality of lines in the L-bundle(L) of line L, but no line outside the L-bundle of L. The ensuing L-bundle is then inverted or solved, either locally or globally over the entire set of lines required for each tomographic image reconstruction, separating the radiation detector total readings into separate contributions associated with each individual line of the L-bundle. The specific pre-reconstruction inversion algorithm depends, among other parameters, on the relative values of the source ring angular rotation $\omega_s$ and the detector ring angular rotation $\omega_d$. When $\omega_s < \omega_d$, 332, a local pre-reconstruction algorithm 342 is applied; this algorithm performs better when sources modulation is applied as will be further described below; algorithm 342 leverages oversampling on the detector side. If $\omega_s = \omega_d$, 334, local pre-reconstruction inversion algorithm 344 applies, with or without source modulation. When $\omega_s > \omega_d$, 336, local pre-reconstruction inversion algorithm 346 leverages source oversampling, as further described below. In all situations, and after iteration at step 354 on the set of lines L 314 related to the sinogram 304, an estimate of the individual line-integral measurements 364 is obtained. These separate contributions are then associated with the corresponding lines in the sinogram 364 to provide input data for image reconstruction. The inversion or solving operations 342, 344, 346 also can be formulated as using as constraints the correlation information obtained by correlating the summed projection data with the source parameter modulation vectors. It is understood that, in certain embodiments, the line-bundle for any line L consists substantially of the entire summed projection data set associated with one tomographic slice to be reconstructed; and the constrained inversion problem applies directly to that entire slice-related data set (sinogram) in a "global" pre-reconstruction inversion. In other embodiments, L-bundles can be formed that relate to a significantly smaller subset of the acquired data, and pre-reconstruction inversion is performed "locally" on the limited sub-sets; in such a manner that obtaining an estimate for line-integral L involves solving a system of equations with at most as many rows (measurements) as there are radiation sources in view of the detector for the measurements; or a number of rows related to the number of sources and the geometry of the system, as further described below. In either case, pre-reconstruction inversion in achievable locally, a preferred embodiment of the present invention.

Figure 4:
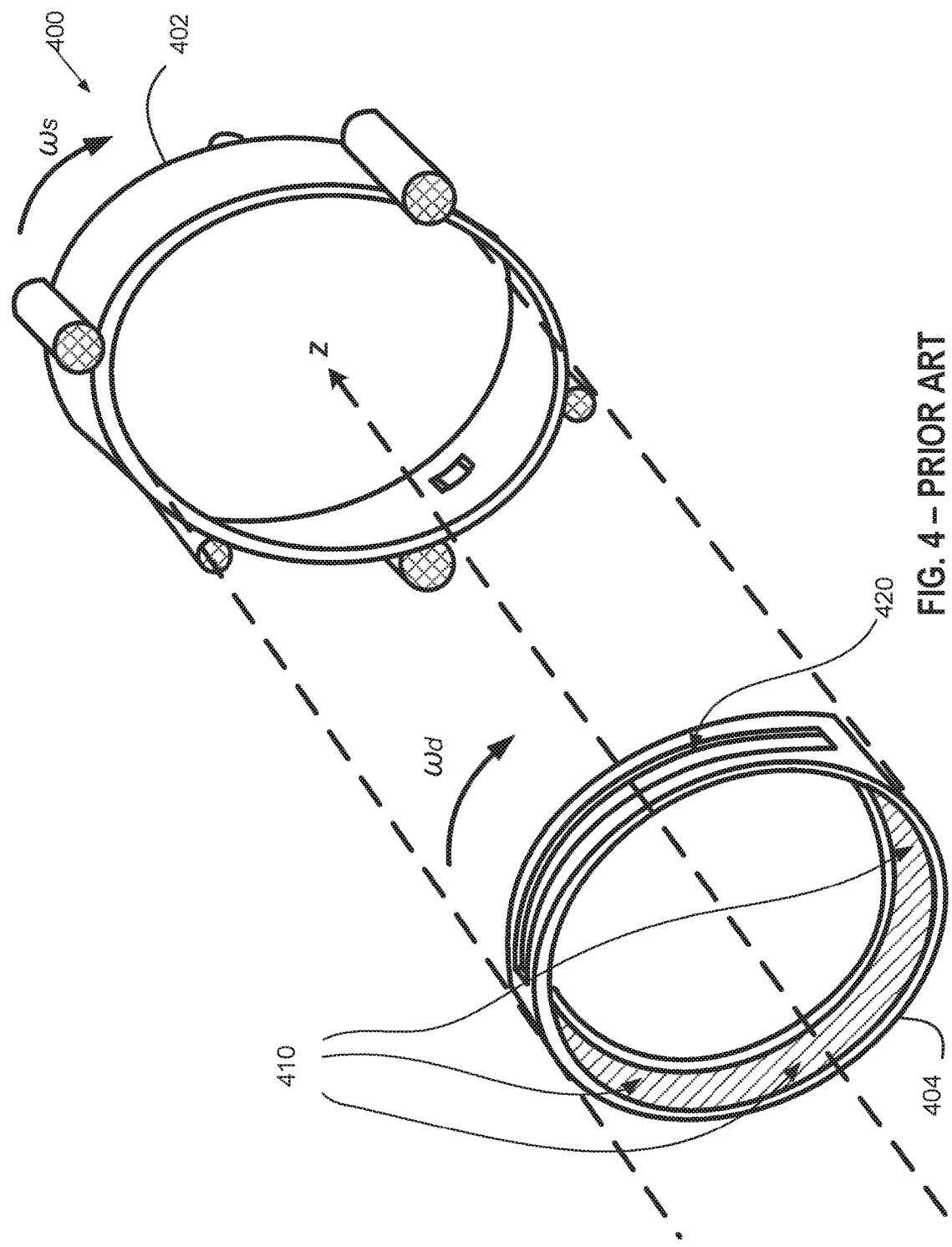
FIG. 4 shows a system diagram for a dual-drum multi-source CT system architecture comprising five conventional rotating anode-stem (or alternatively fixed-anode) X-ray sources.

FIG. 4 schematically presents a CT system architecture recently introduced by the inventor that leverages several conventional X-ray tubes. A new scalable CT system architecture is introduced with the potential to achieve much higher temporal resolution than is possible with current CT designs while maintaining the flux per imaged slice near today's levels. In particular, effective rotation speeds several times higher than what is possible today can be achieved leveraging today's X-ray tube designs and capabilities. The new CT architecture includes the following elements:

(1) decoupling of the source rotation from the detector rotation through the provision of two independent, coaxial and coplanar rotating gantries (drums);

(2) observation of a source at a range of azimuthal angles with respect to a given detector cell;

(3) utilization of a multiplicity of X-ray sources;

(4) use of a wide-angle 410 isocentered detector mounted on the independent detector drum;

(5) the detector drum presents a wide angular aperture allowing X-rays from the various sources to pass through, with the active detector cells occupying a central angle $\pi+2\Gamma$ or about 240-degrees in one configuration, and the wide aperture the complementary $\pi-2\Gamma$ radians or about 120-degrees;

(6) optional anti-scatter grids with absorbing lamellas oriented substantially parallel to the main gantry plane; and (7) optional sparse view acquisition in "bunches," a sparse sampling pattern potentially enabling further data acquisition speed-up for specific applications.

Temporal resolution gains are achieved when K multiple sources are simultaneously in view of the extended detector. Accordingly, projection data relate to the sum of up to K line-integral terms; Recovery of the individual line-integral estimates that form the input to the usual image reconstruction methods, necessitate the inversion of a sparse system. When data for a tomographic slice are acquired during a full effective gantry rotation, the system is amenable to inversion. A specific method described below shows that the problem is also amenable to local pre-reconstruction inversion, using sources modulation control in specific imaging conditions.

With respect to X-ray generation using electron-beam bombardment of a high-Z target material, several methods are available to generate higher power in a rotating-stem anode (conventional) X-ray tube design. Increasing system rotation speed leads (via a linear relation) to a corresponding increase in tube power needed to keep the flux/dose/illumination per rotation a constant. The instantaneous amount of X-ray power that can be generated without damage by an X-ray target, such as a tungsten target, by bombarding it with an electron beam, increases as the relative velocity between the target and the electron beam increases. As is known in the art, the rise in temperature $v_{Focus}$ for short load times (<0.05 s for standard focal spot dimensions) can be approximated by:

$$\vartheta_{Focus} = \frac{2P}{A_F}\sqrt{\frac{\delta}{\pi^2 R\lambda \rho c f}} \qquad (1)$$

where here P is the power input, $A_F$ is the focal spot area, $\delta$ is half the focal spot width, $\lambda$ the thermal conductivity, $\rho$ the mass density, c the specific heat, f the anode rotation frequency, and R the focal track radius. Similarly, the focal track temperature $v_{Track}$ increases as the number of revolution n=t f (n, number of revolutions during the time t) per the relationship:

$$\vartheta_{Track} = k\vartheta_{Focus}\sqrt{\frac{\delta}{\pi R}(n+1)}, \qquad (2)$$

where k is a factor accounting for the anode thickness, thermal radiation, and radial heat diffusion.

Thus, to meet increasing power demands, the standard approach in CT has been to design X-ray tube with larger and larger rotating anode inserts, and thus larger R.

For illustration, one of the largest X-ray CT tube currently on the market has an anode disk with a diameter d of 20-cm, and rotates at about 10,000 RPMs, or about 167 rotations per second: $\omega = 2\pi \times 167 \sim 1047$ radians per second. Such a target diameter also corresponds to a maximum target length $T_{LDisk}$ of about $T_{LDisk} = \pi d \sim 0.63$ m, and a maximum target velocity $V_{TDisk}$ given by:

$$V_{TDisk} = \omega \times r = 1047 \times 0.1 \sim 105 \frac{m}{s}$$

(or about 378 km/hr). Various combinations of anode diameter and rotation speed for various X-ray tube designs lead to a current maximum track velocity of about 100 m/s (or about 360 km/hr); In the following we retain this number as a desirable performance characteristic for our new design. In this document, the dimensions of a typical medical CT system are considered for illustration: the X-ray focal spot is at a distance $R_S$ from isocenter, $R_S$=0.57 m, and the imaging field-of-view has a radius $R_M$=0.25 m. Thus an annular ring target of radius $R_s$ has a length $T_{LRing}$ given by: $T_{LRing} = 2\pi R_S \sim 3.58$ m. To achieve a velocity of the target material under the electron beam equal to that of the largest disk anode described above, we require the emitter support structure to rotate with respect to the annular target at an angular velocity of about 100/3.58~28.0 rotations per second, or about 1,680 RPMs.

Figure 5:
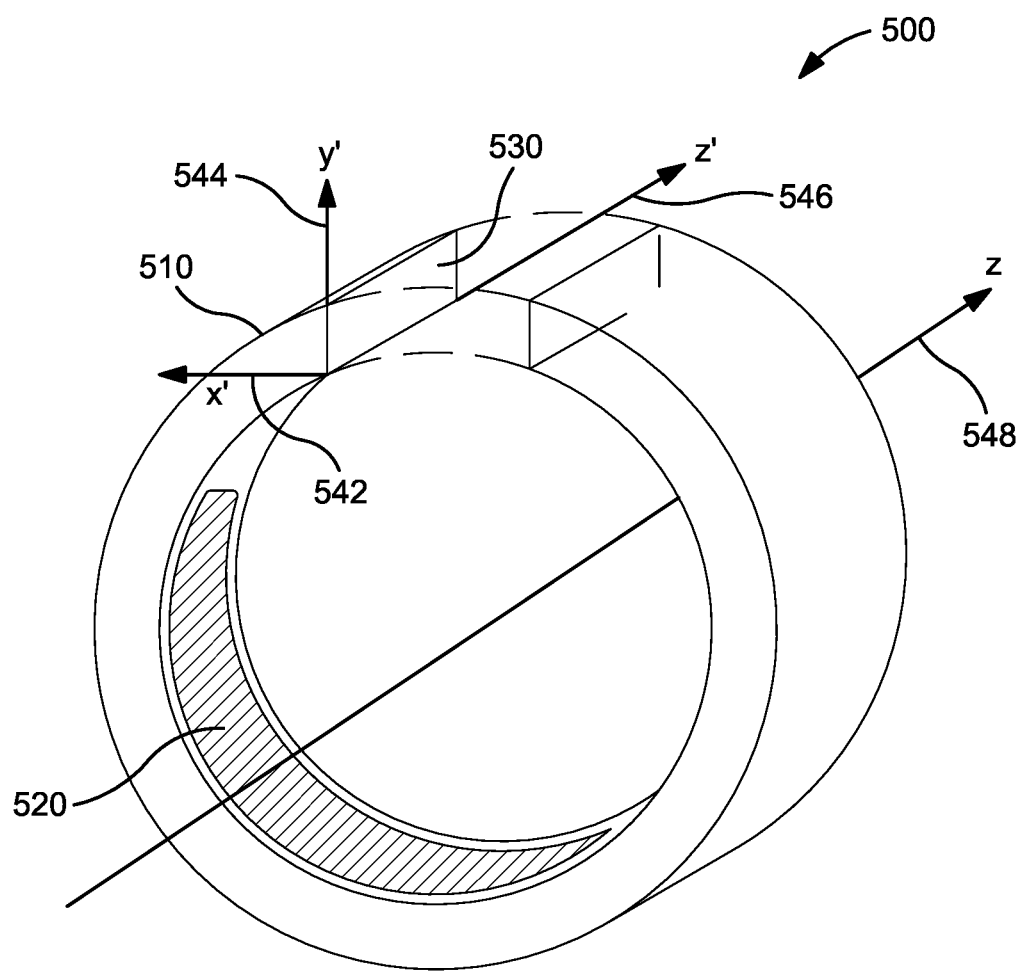
FIG. 5 presents a three-dimensional perspective rendition of a multi-source dual-rotation CT system with an X-ray generation sub-system having a dual annular ring structure in a vacuum envelope, and a rotating detector, per the present invention.

Thus we propose to decouple the emitter from the target, and to arrange a plurality of emitters on an emitter mechanical support structure rotating inside a vacuum envelope, c.f. 500, FIG. 5; in the figure, the radiation detector array 520 is mounted on separate drum and rotates (outside the vacuum envelope 510 inner volume) within the cylinder volume defined by the inner surface of the vacuum envelope and having for axis the system longitudinal axis z 548. The detector array may have a variety of shapes, number of segments, and may rotate at the same or a different angular velocity than the emitter mechanical support structure (not shown in FIG. 5) provided within the vacuum envelope.

Within the vacuum envelope, and facing the emitters, is a target ring. The target and emitter rings may be mounted on mechanical bearings; or alternatively may be magnetically levitated within the vacuum envelope. Such magnetic levitation is potentially advantageous, as it enables rotation without friction and the realization of high-speed motion. For examples, there exist in a number of countries magnetically levitated train structures, providing speeds in the range of 300 to 500 km/hour in actual, commercial service. In the novel CT X-ray sources application described herein, such high speeds will be facilitated by the design requirement for a high level of vacuum in the X-ray generation vacuum envelope.

Given magnetically levitated target and emitter rings, the above requirement of about 360 km/hr or 1680 RPMS can be attained; indeed, the requirement may be split between the two rings. For example, providing an emitter ring rotation of 200 to 400 RPMs in one direction, the target ring needs to be rotated in the opposite direction at 1280 to 1480 RPMs (or 274 km/hr to 317 km/hr). Thus if need be the relative rotation speed of the electron beam with respect to the target may be significantly increased as compared to the current state-of-the-art, leading to increased instantaneous power capability in the proposed design.

An annular target at radius 57 cm has a length of about 3.56 m, as compared to about 0.63 m for a rotating-stem-anode with a 20-cm diameter. Thus, for a comparable distance between focal exposures on the target, it is in principle possible to provide about six cathodes on the cathode ring: The length of the targets, scaling with the respective radii, allows the operation of about 6 emitters on an emitter ring while keeping the linear target distance between two electron beams to be similar to the length of a commercially available maximum-radius disk anode target track [for the illustrative medical CT system dimensions retained in this document].

Further, the geometry of the target ring allows for a larger target mass and target-backing mass compared to a system comprising one or a plurality of conventional X-ray tubes. This is because, the volume of the backing and the mass of the backing are not limited by design constraints in the same way (by rotation forces both around the tube rotation axis and the system main axis) as for the design of a conventional rotating anode disk X-ray tube. A design with a plurality of emitters, including a dozen or more emitters operating at the same power specification as today's state-of-the-art emitters, becomes possible. Such a system is schematically illustrated in FIG. 5, showing a three-dimensional perspective rendition of a toroidal vacuum envelope. A radiation detector is mounted on a rotatable gantry (not shown) that rotates the detector outside the vacuum envelope and at a slightly smaller radius. In operation, the radiation detector is rotated within the volume defined by the vacuum envelope surface at smallest radius. FIG. 5 provides a schematic three-dimensional representation of an annular ring-shaped vacuum envelope. The vacuum envelope contains a target ring and an emitter ring (not shown). A detector is provided, external to the vacuum envelope. The detector is mounted on a separate gantry (gantry not shown), and can be rotated in operation outside the vacuum envelope. On the inside surface of the vacuum envelope there is an X-ray window (not shown) that maintains the vacuum within the envelope and presents favorable X-ray attenuation property as well as thermal properties.

In a conventional rotating anode disk X-ray tube design, heat transfer away from the anode is effected via radiative cooling and via conductive cooling at the rotating anode rotor-to-stator contact area. Cooling elements such as channels and circulating fluid within are provided on the external side of the vacuum envelope to facilitate heat removal from the sub-assembly. In a typical CT X-ray tube, the vacuum envelope or "insert" is contained within an oil bath inside the tube housing; the oil circulates to a heat exchanger where heat generated within the X-ray tube is dispersed in the environment.

The relatively short life of X-ray tubes ball bearings is particularly due to the fact that a portion of the heat generated during operation of the anode is dissipated via the bearings. It is possible for the average temperature of the ball bearings to increase to approximately 300-degrees C. The ball bearings must operate in a vacuum. So ball bearings cannot be sufficiently lubricated so that the ball bearings must have a sufficiently large clearance to prevent the bearings from sizing up, and this in turn implies a relatively large amount of noise during operation. The life of the ball bearings is further reduced by the fact that the tube current is passed through the bearings. This results in spark erosion of the bearing.

Spiral/helical groove liquid metal technology is an approach designed to significantly increase the bearing surface area [compared to ball bearings], thereby allowing larger heat dissipation through the bearing while maintaining and/or enhancing bearing life. It also enables much reduced noise operation. This technology incorporates two separate developments: (1) liquid metal lubrication, which may be traced as far back as a U.S. Pat. No. 2,293,527 by Z. Atlee "X-ray generator lubricating structure" which describes metal with very low vapor pressure at high temperature an high surface tension appropriate for X-ray tube bearing liquid metal lubrication and (2) the spiral groove mechanical design, c.f. for example U.S. Pat. No. 4,375,555. Substantially the spiral groove design leverages liquid metal lubrication to increase significantly upon a bearing contact surface area [and hence safe thermal power transmission capability]. Liquid metal bearings use the aquaplaning effect of liquid metals and offer the following advantages: The bearing system is free of wear and tear; the generation of running noise is minimal; Additional anode cooling can be achieved by fast heat flux through the liquid metal in the bearing system.

The load capacity of a liquid bearing depends essentially on the diameter and length of the design, on the rotation speed, on the viscosity of the liquid and on the size of the gap filled with liquid. It is necessary to ensure that the liquid metal does not escape from the bearing under any operating conditions and that the liquid metal does not form an alloy with other bearing parts. This can be achieved by selecting appropriate materials, using a surface coating and deploying accurately machined bearing parts. The anodes in commercially available X-ray tubes equipped with liquid bearings are typically run at a rotation speed of 150 Hz.

U.S. Pat. No. 4,375,555 describes the principle of the spiral groove bearing using liquid metal lubrication. As stated above the benefits of this approach are (1) Better heat dissipation from the anode by heat transfer through the bearings; (2) Quiet operation; (3) Longer life, as the liquid-metal bearing is much more efficient and provides a reliable solution for the transfer of both insert thermal energy and tube current, as compared to ball bearings. In operation, mutually cooperating metal (e.g. Tungsten (W) or Molybdenum (Mo)) supporting faces of the sleeve bearing are separated by a liquid layer wetting the supporting faces. The liquid layer consists of a metal or metal alloy, such as Gallium (Z=31) (Ga) or a Ga-alloy, whose vapor pressure at 300-degrees C. is below $10^{-5}$ N/m$^2$, and which does not attack the supporting faces to any substantial extent. The insulator is made of densely sintered Alumina $Al_2O_3$ (Aluminum Oxide). Alumina is the most cost effective and widely used material in the family of engineering ceramics. It has (1) Excellent dielectric properties from DC to GHz frequencies; (2) Good thermal conductivity; (3) High strength and stiffness.

A conventional rotating anode X-ray tube according including magnetic bearings is characterized by the bearing system comprises an axial magnetic bearing and a radial sleeve bearing. In operation, mutually cooperating metal supporting faces of the sleeve bearing are separated by a liquid layer wetting the supporting faces. The liquid layer comprises a metal or a metal alloy whose vapor pressure at 300-degrees C. is below 10-5 N/m2, and which does not attack the supporting faces to any substantial extent. Wetting of the supporting faces by means of this liquid layer is to be understood to mean a wetting in which there is a direct interaction between the metal atoms in the supporting face and the atoms in the layer. Furthermore, due to the high surface tension of metals or alloys both in when stationary and during rotation, the liquid metal or the liquid metal alloy is not forced out of the bearings. During operation, both the tube current and the heat generated in the anode can easily pass through the bearing without causing damage because metals have relatively good electrical and thermal conduction characteristics. Both the shaft and the bushings are preferably made of one of the metals W or Mo or of an alloy of W and Mo. The shaft is separated from the bushings by a lubricating layer consisting of Ga or of a Ga alloy which melts at a temperature below 25 C. Wetting of the supporting faces by means of this liquid layer is to be understood to mean a wetting in which there is a direct interaction between the metal atoms in the supporting faces of the bearing bushes and the atoms in the layer. This means that between the layer of Ga or Ga alloy, the shaft and the bushings there is present neither an oxide layer of the metal of the shaft or of the bushing, nor an oxide layer of Ga or of one of the components of the Ga alloy. Such wetting may be obtained by, for example, heating the shaft, the bushings and the Ga or the Ga alloy in a reducing atmosphere, for example in H2 gas, for some time at 800-degrees C. Any oxides present are then reduced. The wetting produced in this manner is so good that the shaft and the bushings are completely separated from one another in the X-ray tube, both while at rest and while operating. Seizing-up of the supporting faces is thus prevented. In the region of the bushings, the shaft is provided with V-shaped pairs of helical grooves, the helices being of opposite sense, which additionally cause the Ga or alloy to be forced (and retained) into the bearing in operation. This results in bearings with high dynamic stability. Because the vapor pressure of Ga and Ga-alloys is below $10^{-5}$ N/m$^2$ at 300-degrees C., no unexpected gas discharges will occur in the X-ray tube. Since the shaft and the bushings consist of one of the metals W, Mo, or an alloy of W and Mo, they are not attacked to any substantial extent by Ga or Ga-alloy.

Per Varian U.S. Pat. No. 6,327,340, a heat removal device, consisting of a liquid metal, such as gallium, is held in contact with the rotating anode in a heat removal area within the vacuum tube. The areas of liquid metal that are used to conduct heat from a surface of the anode are substantially confined within a defined area along "external" surfaces of specific anode members, by placing a first film along each of those surfaces. The film can be composed of any material that has an affinity for the particular material used in the liquid metal, such that the liquid metal tends to stay in contact with the film. For example, molybdenum, tool steel, tungsten, or silicon dioxide could be used. In addition, the liquid metal areas are confined within the defined area by placing a second film layer on both sides of the first film layer. Preferably, the second film is comprised of a material that does not have an affinity (i.e., tends to repel) the liquid metal, further influencing the liquid metal to stay within a prescribed boundary area. The second film can be composed of graphite, molybdenum carbide, titanium dioxide, silicon nitride, silicon carbide, or aluminum oxide.

In tubes designed with magnetic bearings, it is important to note that the liquid metal contact does not have to constitute a bearing. Rather, such contact serve to provide a return path for the tube current, and crucially, a thermal path of least resistance for anode heat to be dissipated to the housing and subsequently the environment without impacting the bearings. Thus, magnetic bearings offer the potential for substantially frictionless rotating anode designs (a return path needs to be provided for the tube current). This technology is of substantial interest in the quest for higher anode rotation speeds associated with higher peak power capabilities.

As described briefly above, in recent years, approaches leveraging both magnetic bearing technology and liquid metal contacts have been proposed; designs where liquid metal contacts provide thermal path(s) of least resistance to protect the magnetic bearings. Magnetic bearings have been proposed as a means to support a rotating anode both axially (i.e., along the anode axis length) and radially (i.e. centered in a plane perpendicular to the anode axis of rotation). In principle, frictionless magnetic bearings enable very high anode rotation speed and thus peak operating power. Magnetic bearings can be realized passively by permanent magnets and/or as actively controllable electromagnets. Such technology was first proposed more than 30 years ago; however, the following design challenges limited application: (i) Permanent magnets lose all magnetization above their Curie point, at about 500° C. for most known/practical magnetic materials used to generate the suspending magnetic field. Even heat-tempered magnetic components begin to lose their functionality at temperatures above 200° C. Accordingly, the bearings must be protected from both radiated and conducted heat. (ii) Magnetic bearing preferably require a unipolar design with the anode held at ground potential, to minimize gap distances between rotor and stator and ensure sufficient magnetic bearing forces.

Varian U.S. Pat. No. 6,327,340 (December 2001) describes a rotating anode X-ray tube with magnetic bearings and liquid metal contacts on the "straddle" bearings. The liquid metal contacts convey heat from the rotating anode to the envelope and thermally shield the magnetic bearings. Such a frictionless design in principle enables high anode rotation speeds with lower/reduced rotational drive power. U.S. Pat. No. 8,102,969 to Bittl and assigned to Siemens (24 Jan. 2012), discloses a somewhat more conventional rotating anode design with magnetic bearings. Here, a large pin/shaft extension upward of the anode provides a heat conduction path of least resistance from the anode to the housing via a liquid metal contact. To further shield the magnetic bearings, various measures are taken to impede heat flow from the anode down the shaft: (i) use of a (possibly laminated) insulating ceramic layer just below the anode disk; (ii) use of a hollow shaft neck with small diameter and reduced cross-sectional area; (iii) use of a heat plate around the narrow neck to shield the magnetic bearings from the radiative heat transport from the anode. Per the patent, this tube is unipolar and designed to operate with the anode at ground potential, thus allowing smaller gaps between the motor and rotor parts of the magnetic bearings. A key object of this design is to reduce frictional forces through the liquid metal contact areas, here achieved via a larger gap (100 to 200 microns, versus 10 to 20 microns typical for a liquid metal bearing) as well as the surfaces locations near the rotation axis (reducing friction forces moments).

Varian US patent application 2010/0322383 aims at a similar goal, by providing extended surfaces near the anode axis and in the anode disk center via a cavity, for enhanced radiative cooling to a central, non-rotating cylindrical element that can be cooled by flowing oil in direct contact. This design is for a "magnetic assist" bearing with "catcher ball bearings." The mechanical load from the rotating anode is shared between the two bearing mechanisms. Siemens U.S. Pat. No. 8,102,969 (January 2012) describing a rotating anode X-ray tube magnetic bearing with liquid metal contacts on the large anode shaft extension upward of the anode plate. Since the liquid metal contact does not constitute a bearing, the liquid metal-filled gap can be of the order of 100-200 μm (as opposed to 10-20 μm for a liquid metal bearing). Per the patent, this allows reduced frictional forces to be applied to the rotating anode. Note also the various measures taken to reduce/minimize heat transfer from the anode to the magnetic bearings: (i) Ceramic insulator just below the anode disk (possibly including layers orthogonal to the rotation axis); (ii) Hollow tube neck with small cross-section, surrounded by a metal shied plate to prevent radiative heat transfer to the bearings. It is preferable that the anode is directly cooled in a liquid metal by thermal conduction as it rotates in a magnetic contactless bearing. The thermal conduction prevents the materials in the rotating anode from being heated past their Curie point and losing their magnetic properties. Various hybrid concepts have been proposed for this reason, wherein slide and magnetic bearings are combined to bear the shaft of the rotating anode unit. It will now be clear to those skilled in the art that such hybrid designs apply to the present invention as well.

Thus, both liquid bearing technology and magnetic bearing (or magnetic levitation) technology are adaptable to the approaches of the present invention and the designs of a large toroidal vacuum envelope with one or two rotating rings within.

In the present design, it is necessary to provide power to the two rings. Power to enable levitation (if electromagnetically enabled), rotation, and supply of high-voltage power on the emitter ring side as well as filament current and power. Optionally, power for electronic beam shaping elements, such as electrostatic electrodes or electromagnetic beam deflection is provided.

Power transmission may be effected via slip-ring technology (including liquid metal technology), or via AC power-over-gap transmission technology as is known in the art. This is particularly well suited to the high-power emitter ring application as it limits the needs for power conditioning aboard the rotating emitter ring (within the vacuum envelope).

Figure 6:
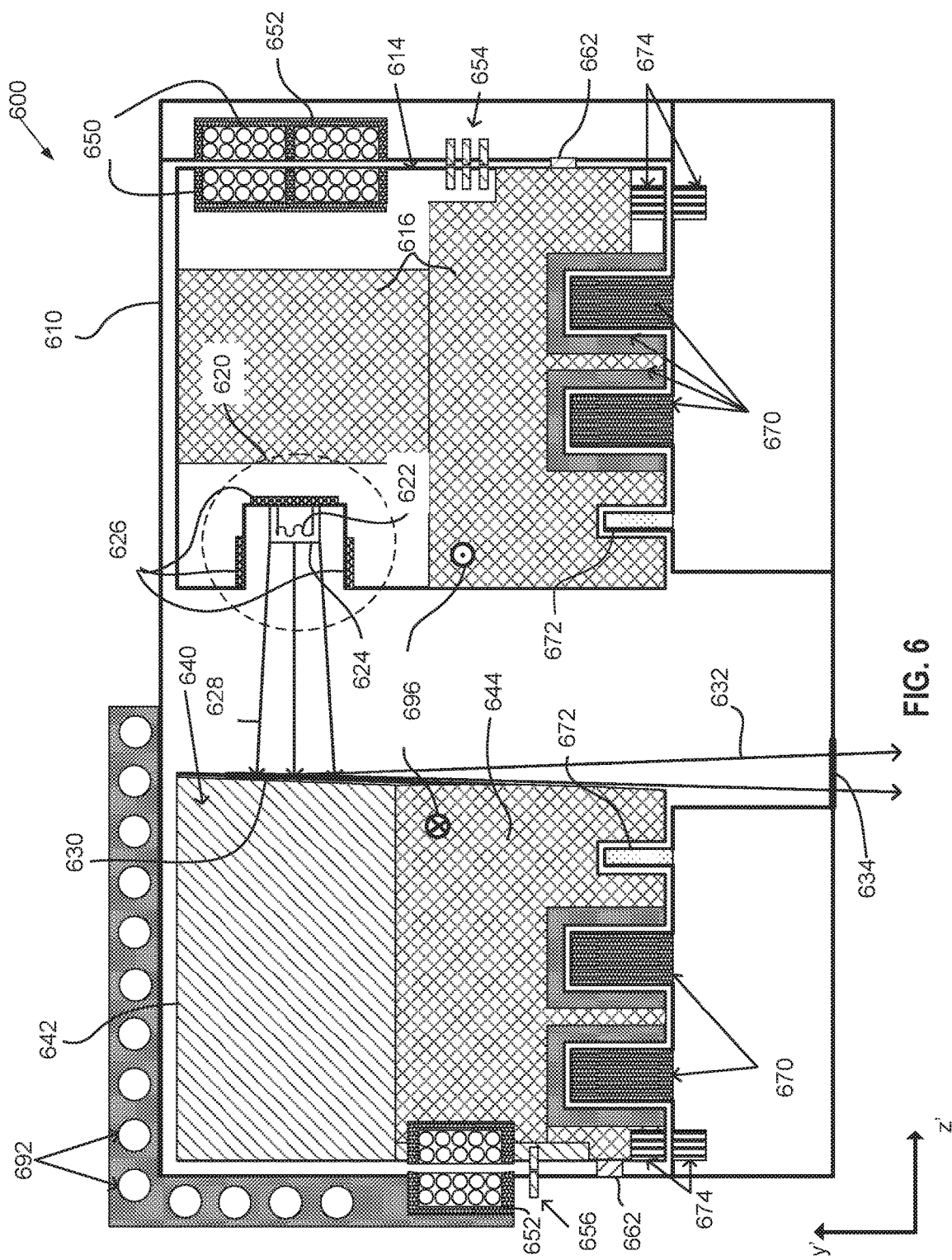
FIG. 6 schematically depicts a cut through a plane y'-z' of the X-ray generation sub-system of FIG. 5, with a magnetically levitated target ring and a magnetically levitated emitter ring, the cut y'-z' passing through the center of one of a plurality of electron-beam emitters.

FIG. 6 schematically illustrates 600 a cross-section of the vacuum envelope 510 along plane y' 544-z' 546 of FIG. 5. It shows an embodiment of the present invention, with both the target ring 640 and the emitter ring 614 being magnetically levitated within the vacuum envelope 610. The plane of the cross-section cuts through one of a discrete plurality of emitter cups 620 on the source ring, showing in cross-section a cathode element 624 with a heating filament 622 underneath it; high-voltage electrodes 626 for acceleration of electrons "boiled off" the cathode element and shaping the electron beam 628. In some embodiments, the heating filament and cathode elements are the same element. Most of the other elements shown in the figure may have substantially circular symmetry within the vacuum envelope and around the bore thereby formed. The substantially circular symmetry may be continuous or nearly continuous, as in the case of the anode target 630 and the anode heat and current conduction material 642 supporting and backing the anode; the substantial circular symmetry may present a number of discrete cycles, such as in the case of the magnetic drive motor elements 674. The circular symmetry may be broken in examples where the wiring shown in cross-section for the high-voltage power transmission over gap 650, 652 bends away from the vacuum envelope flange and into a power conditioning unit mounted on the rotating emitter ring (not shown). The X-ray target 630 is mounted and/or brazed onto a backing material 642 with high thermal conductivity. Facing this material, but mounted on the vacuum envelope, are cooling channels 692 through which a fluid may be circulated to help in removing heat from the target to the environment. These cooling channels may be connected to a heat exchanger (not shown). Generally mounted below the high thermal conductivity element is a heat shielding structural layer 644, which provides mechanical integrity to the target ring while protecting the magnetic levitation 670 and magnetic drive elements 674 from the high heat generated by the X-ray target when in operation. To close the current loop, a charge drain 656 is provided on the target ring side to establish contact with the vacuum envelop, and contacts 654 are provided on the emitter ring to enable filament current and beam current control.

A thermally conductive material for an X-ray tube insert is preferably one which has a thermal conductivity of at least 100 Watts/meter*degrees Kelvin, preferably, at least 200 W/m*K, and most preferably, at least 350 W/m*K. The thermally conductive material is preferably free or substantially free of materials that have a tendency to outgas in the high vacuum conditions of the X-ray tube. Suitable thermally conductive materials of this type include copper, copper-beryllium alloys, and other copper alloys. For example, the thermally conductive material may be formed from copper, with copper being the primary element present. The thermally conductive material preferably comprises at least 90% copper, more preferably at least 99% copper. At high purity, copper has a thermal conductivity of about 400 W/m*K. The thermal conductivity of copper-based materials tends to diminish as the proportion of alloying material or impurities increases. In contrast, stainless steels have a thermal conductivity of 10-25 W/m*K. In general, the thermal conductivity of the structural material is less than that of the thermally conductive material, generally, less than half the thermal conductivity of the thermally conductive material.

AC Power is provided to the emitter ring via power-over-gap technology, including elements 650. Thus, rectifiers and power conditioners (not shown) are mounted on the rotating emitter ring to provide the tube high-power voltages. The power conditioning electronics are shielded from the emitters and target ring heat by heat shields. Additionally, and optionally, contacts and means of controlling electron-beam focusing and deflection via either electrostatic or electromagnetic means are provided, as known in the art.

Operation of permanent magnets within the vacuum envelope may lead to considerations of out-gassing from the materials. The use of electromagnets, both on the rotating and fixed sides of the rings may alleviate this potential difficulty. It is desirable to provide levitation in the absence of power, and thus permanent magnets may be preferred or required. Out-gassing may also be controlled by the use of a vacuum pump and of ionizers and/or electrostatic catchers (not shown). For portions of the insert frame exposed to the vacuum environment, the framework material is preferably selected to minimize impurities that tend to outgas. Stainless steels, Inconel™, nickel alloys, titanium, and Kovar™ are suitable vacuum compatible materials.

The combination of copper and stainless steel is particularly suitable for forming the liner and framework of an insert. They have relatively similar thermal expansion coefficients. The coefficient for copper is about 20×10–6 cm/cm/° C., which is slightly higher (about 10% higher) than that of stainless steel.

In applications to a relatively large bearing as proposed in this disclosure, it might be preferable to locate the liquid-metal contact (if using this technology) elements 662 axially (as shown) rather than radially (on the sides of the apparatus shown in FIG. 6). This is because at high rotation speeds the annular ring target might be expected to deform by a small amount, due to residual unevenness in weight distribution, cyclical variations in rotating against versus with the local gravitation field, and thermal effects. These deformations are expected to be significantly less on the axial sides of the ring(s), when operating vertically in a typical CT application. Elements to ensure target ring guidance, such as axial bearings, including various types such as magnetic bearings, are not shown in FIG. 6 nor in the other figures of this document.

Suspending the rotating part of a machine in a magnetic field may eliminate the contact friction present in conventional mechanical bearings. Magnet bearings may be based on either attractive or repulsive force. The attraction type offers the advantage of controlling the suspensions dynamics but is inherently more complex and is used in high-performance and heavy-duty applications. [P. K. Sinha, McGrawhill encyclopedia of science and technology, 10th edition.]

Several magnetic levitation approaches are available. In an attraction-type system, a magnet-guideway geometry is used to attract a direct-current electromagnet toward the track. This system, also known as the electromagnetic suspension system, is suitable for low- and high-speed passenger-carrying vehicles and a wide range of magnetic bearings. The electromagnetic suspension system is inherently nonlinear, requiring an active feedback to maintain an upward lift force equal to the weight of the suspended magnet and its payload. The upward lift force, F(i,z,t), is given by the relationship below, where i is the current and z is the gap, where both terms depend on time t:

$$F(i, z, t) = \frac{B^2 A}{\mu_0} = \frac{\mu_0 N^2 A}{4}\left(\frac{i}{z}\right)^2,$$

where B is the gap flux density, N is the number of turns in the magnet windings, A is the pole-face area of the magnet, and $\mu_0$ is the permeability of free space. A basic form of state feedback controller which maintains a constant clearance (gap) between the guideway and the magnet is frequently implemented in such applications. The position feedback maintains a constant airgap ($z_{ref}$) and suspension stiffness, the velocity feedback introduces damping, while the acceleration feedback controls damping and ride quality. High-performance microprocessors and digital signal processors are used to implement this and other forms of advanced control laws to provide a high degree of suspension stability and ride characteristics. For vehicle suspension applications, the gap is kept in the range of 12-15 mm, with gap flux densities of the order of 1 tesla. For other applications, such as magnetic bearings, the gaps can be as small as 1 mm with considerably lower flux densities.

Due to their contactless operation, linear motors are used to propel maglev vehicles: linear induction motors for low-speed vehicles and linear synchronous motors for high-speed systems. Although their performance parameters are different, operationally they are the unrolled versions of the conventional rotary motors. For linear synchronous motors, three-phase windings are mounted on the guideway, and propulsion force is generated by the interaction between these long stator windings and vehicle-borne direct-current electromagnets (field coils). In high-speed electromagnetic attraction systems (such as the Transrapid rail vehicles), the lift magnets are constructed to provide the suspension force and act as the field coils of the linear synchronous motor.

In application to a rotating gantry, maglev technologies may be adapted to the specifics of a relatively large axial bearing presenting a closed circular configuration; for instance, it might be desirable to provide the field coils on the stationary part of the assembly. Various means of propulsion/rotation and guidance of the rings are known from the magnetic levitation art, and include linear synchronous motors and linear homopolar synchronous motors, among others.

Magnetic levitation, guidance, and induction motors are known technologies that can be adapted to the needs of the present invention for the design of magnetically levitated X-ray target rings and emitters. Magnetic levitation technologies, are known to support rail systems at speeds upward of 500 km/hr, or 139 m/s. Therefore, retaining for illustration this number for both the cathode and anode rings rotating in opposite directions, it is potentially feasible to more than double the instantaneous electron-beam velocity with respect to the target as compared to state-of-the-art X-ray tube designs, thus potentially significantly increasing maximum instantaneous beam power.

Magnetic levitation elements and magnetic induction motors need to be shielded from the heat generated in the target and cathodes, since most permanent magnetic materials (if used) tend to lose magnetization in the range 200°–400° C., and are completely de-magnetized above their Curie point (about 500° C.). Permanent magnetic materials tend to lose their magnetic properties at high temperatures, and need to be thermally shielded. The permanent magnetic material Alnico has a maximum operating temperature of 500 degrees C., which compares with a maximum operating temperature of a conventional rotating-anode tube having mechanical bearings of about 400 degrees C. Therefore, the use of thermal shielding is expected to enable the use of magnetic materials within the vacuum envelope.

Power transfer elements and power conditioning circuitry likewise need to be heat shielded. Current conduction to and from the cathode and anode rings respectively is required to close the electrical circuit normally contained within an X-ray tube envelope. Leveraging opposite ring rotation directions may make a design with mechanical ball bearings possible, thus reducing the above complexities and costs. Cathode power increases may be required.

Figure 7:
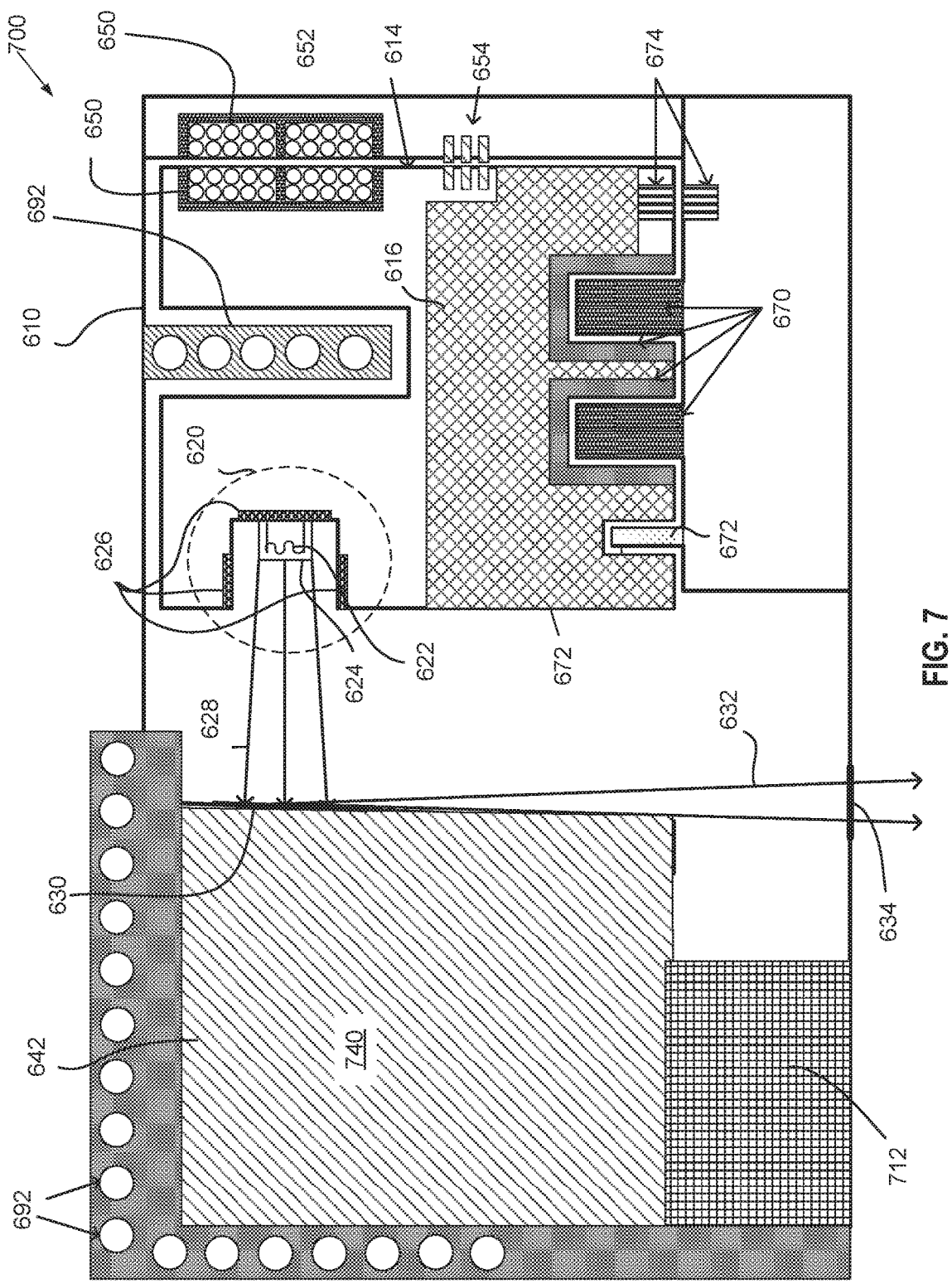
FIG. 7 schematically presents a cut through a plane y'-z' of the X-ray generation sub-system of FIG. 5, with a fixed target ring and a magnetically levitated emitter ring.

FIG. 7 schematically illustrates a dual annular ring radiation sub-system similar to that of FIG. 6, except that the target ring 740 is fixed within the vacuum envelope. This design is suitable when the emitter ring can be designed to sustain high angular rotation speed; or the required power may be distributed among a plurality of emitters to reduce the instantaneous power delivered by one individual electron beam to the target. A significant advantage of the design is that it enables fast heat power removal from the vacuum envelope to the external environment through a contact configuration between the anode and backing elements 642 and the cooling elements 692 on the external side of the vacuum envelope 610. The design also presents the advantage of a relative simplicity.

Figure 8:
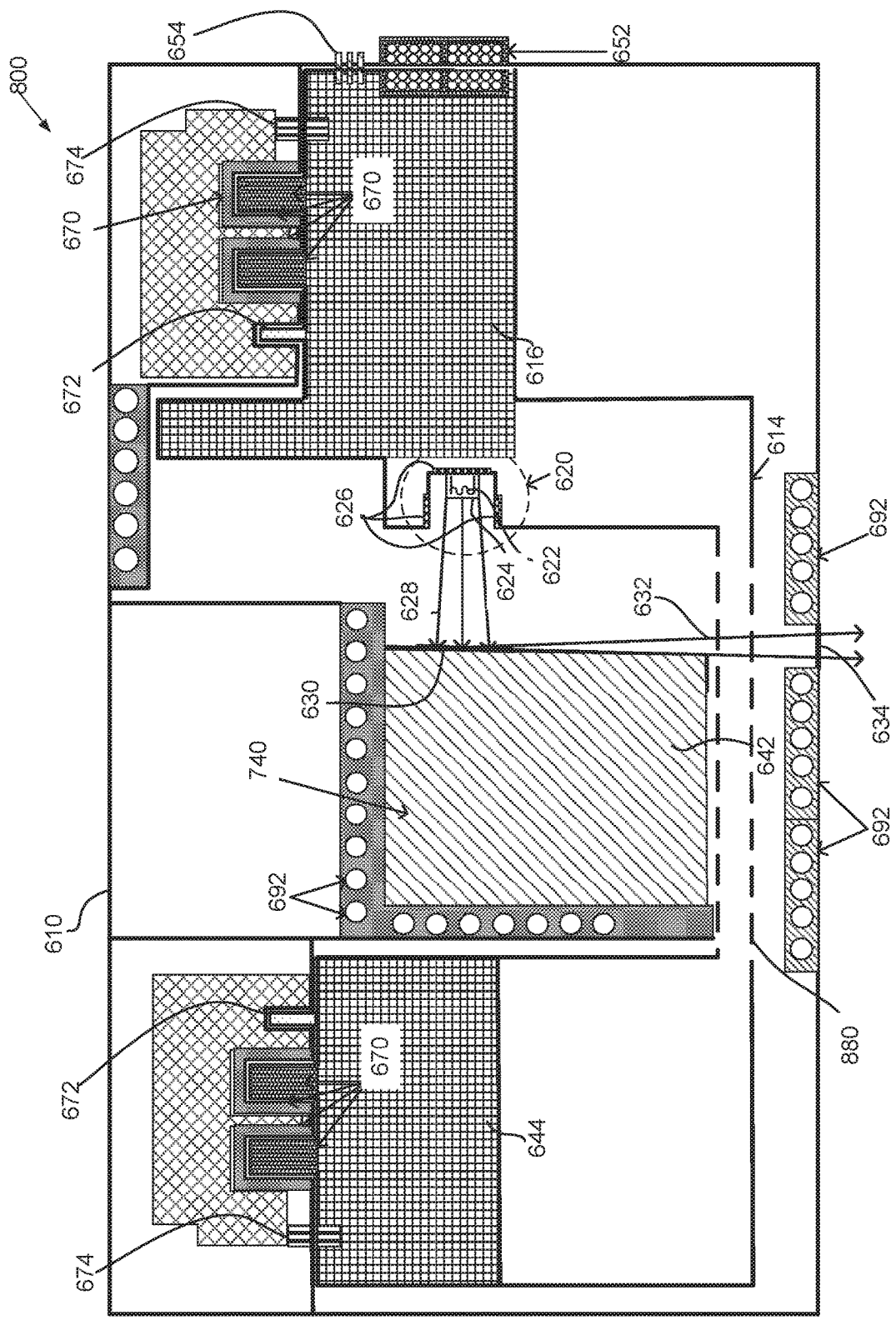
FIG. 8 schematically presents a cut through a plane y'-z' of the X-ray generation sub-system of FIG. 5, with a fixed target ring and a magnetically levitated emitter ring supported by straddle magnetic bearings.

In FIG. 8, a straddle design 800 for an embodiment otherwise similar to that of FIG. 7 is shown. That is, the emitter ring 614 is supported (via magnetic bearings in the figure) on either side of the fixed target ring. The V-shaped or U-shaped mechanical members 880 have an aperture between them to allow passage of X-ray beam 632. While not shown in the figure, it is understood that the magnetic bearings 670 could be further offset radially (that is vertically in FIG. 8) to further remove them from the target. Elements 672 serve as thermal shields to protect magnetic bearings. The straddle design approach thus enables significant shielding of the two sides of the magnetic bearing assembly from the heat generated at the emitters and target focal track(s).

Figure 9:
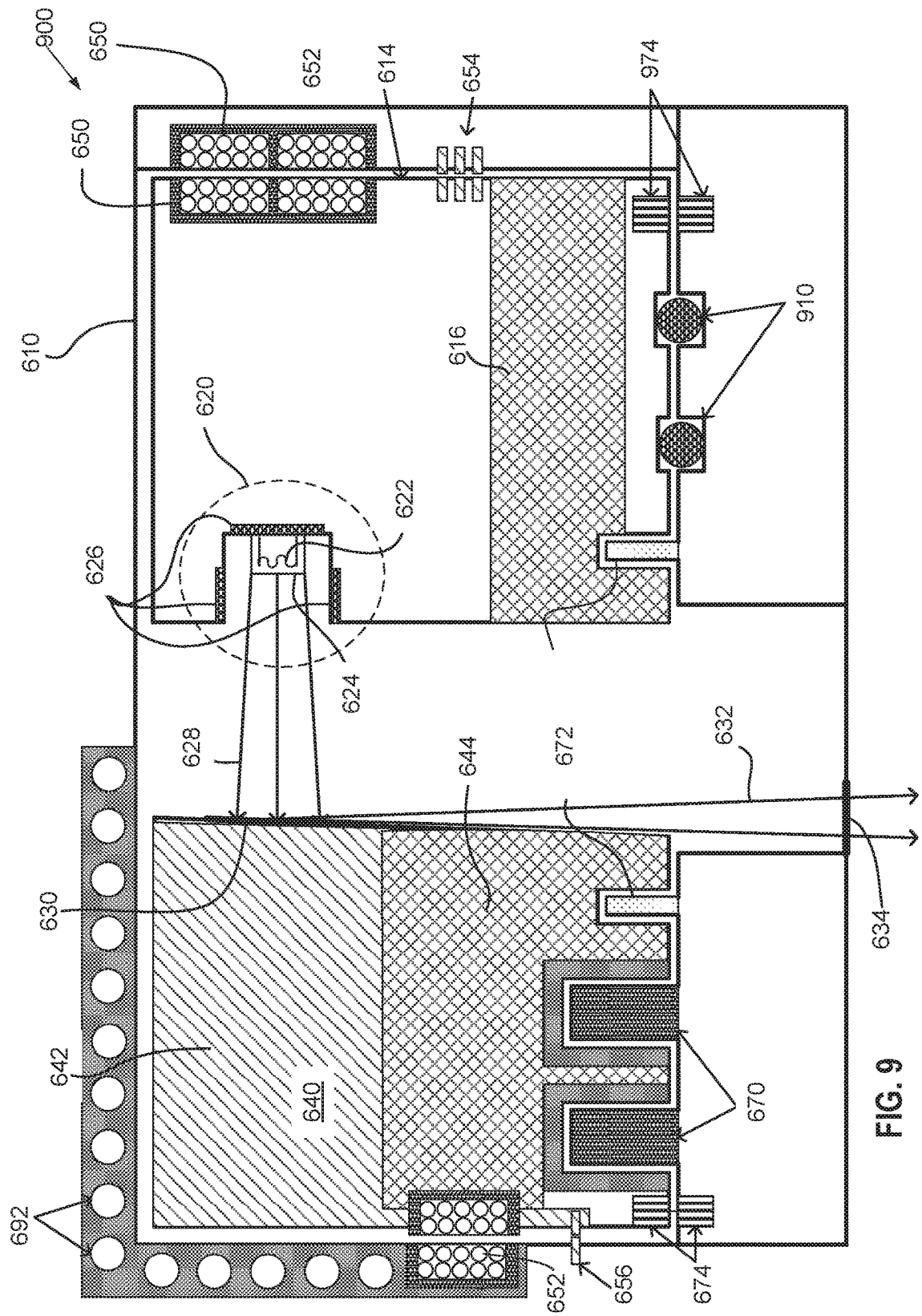
FIG. 9 schematically presents a cut through a plane y'-z' of the X-ray generation sub-system of FIG. 5, with a magnetically levitated target ring and an emitter ring supported by a mechanical bearing.

FIG. 9 schematically depicts 900 a dual annular ring radiation sub-system similar to that of FIG. 6, except that the emitter ring 614 is supported by a mechanical bearing assembly 910 (ball-bearing mechanical bearing embodiment shown). Such assemblies have been proven to work at angular rotation speeds of 400 RPMs and higher, and provide a relatively simple design solution. The mechanical bearings 910 also enable current conduction from the rotating ring to the stationary vacuum assembly and system gantry. As known in the art, it is desirable to shield the bearings from heat via heat shielding elements 672.

Figure 10:
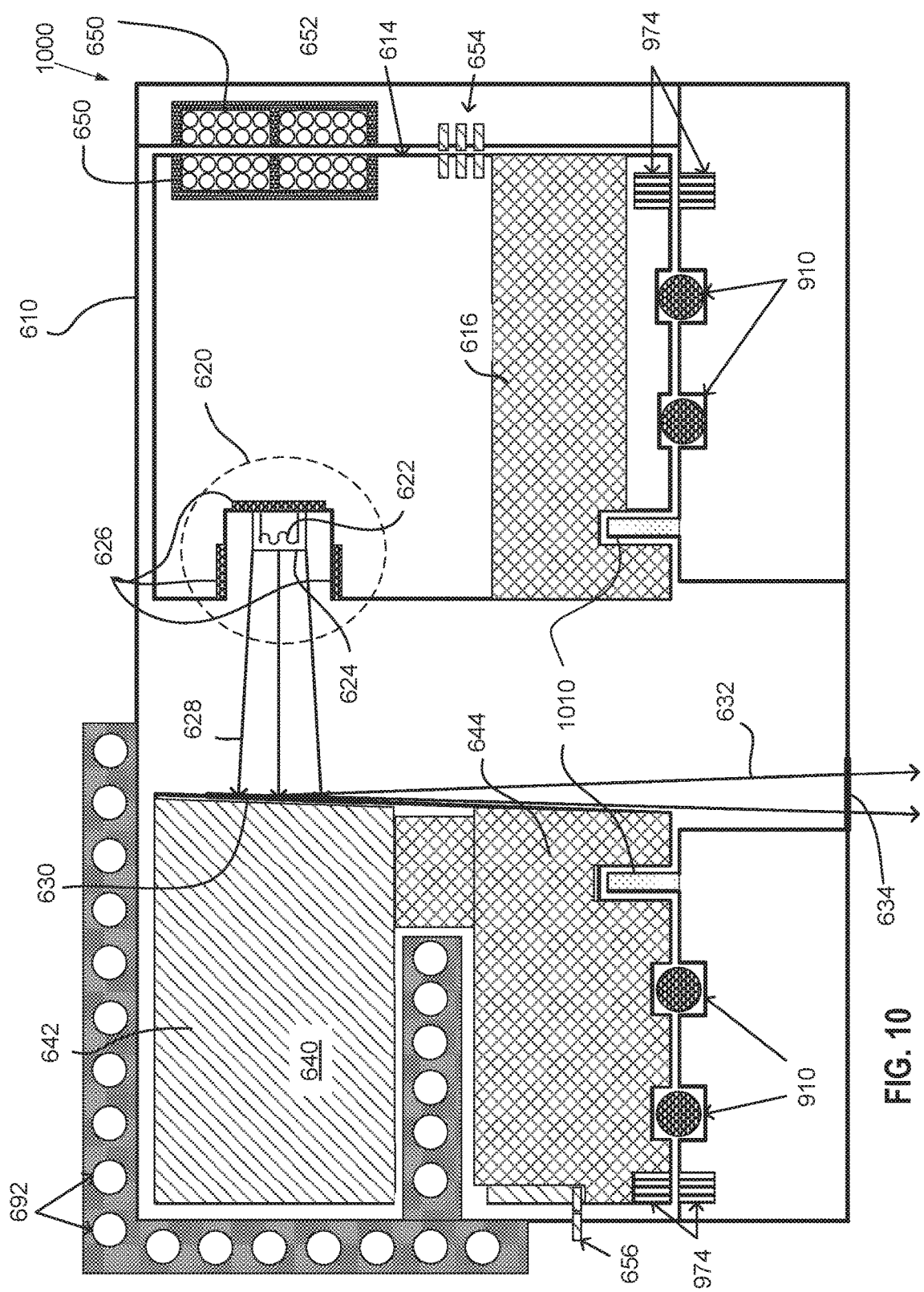
FIG. 10 schematically presents a cut through a plane y'-z' of the X-ray generation sub-system of FIG. 5, with both the target ring and the emitter ring supported by mechanical bearings.

FIG. 10 schematically depicts 1000 a dual annular ring radiation sub-system similar to that of FIG. 9, except that both the emitter ring 614 and the target ring 640 are supported by mechanical bearing assemblies 910. Such assemblies have been proven to work at angular rotation speed of 400 RPMs and higher, and provide a relatively simple design solution. For example, 400 RPMs in either direction leads to an effective 800 RPM angular velocity of the beam with respect to the target; using the ring dimension as above, this enables about 50 m/s velocity of the electron beam on the target material, similar to that currently achieved on some conventional rotating anode X-ray CT tubes. Thus, magnetic levitation is not a requirement to enable the present invention.

Figure 11:
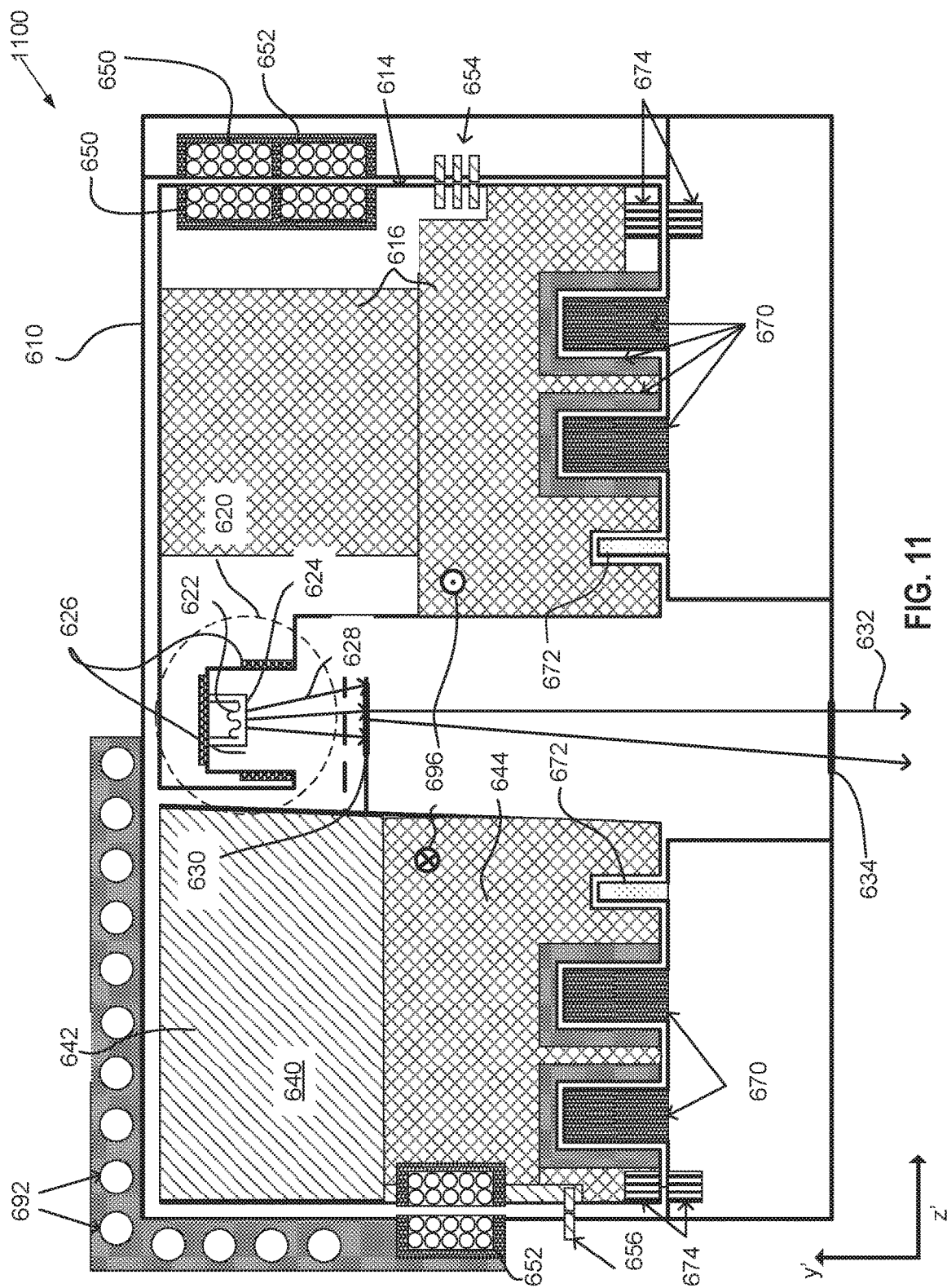
FIG. 11 schematically depicts a cut through a plane y'-z' of the X-ray generation sub-system of FIG. 5, with a magnetically levitated target ring and a magnetically levitated emitter ring, the cut y'-z' passing through the center of one of a plurality of electron-beam emitters, the electron-beam emitters and target being arranged in a "transmission" configuration wherein the emitter cup is arranged on a cantilevered extension on the emitter ring and the target is mounted on a number of segments on a structure cantilevered from the target ring.

In FIG. 11, a dual-ring radiation system similar to that of FIG. 6 is shown 1100, with the emitters 620 and target 630 configured to generate X-ray radiation in a "transmission" mode. That is, the target is illuminated on one side by electron beams 628, and a useful X-ray radiation beam 632 emerges on the other target side. The target can be mounted as shown on a rotating assembly 640, or could be provided affixed to the stationary gantry assembly in a configuration similar to that of FIG. 7, 740. In the illustrated embodiment of a transmission X-ray target, the emitter cup is arranged on a cantilevered extension on the emitter ring and the target is mounted (on of a number of segments along the ring) on a structure cantilevered from the target ring. In embodiments where the target ring is fixed, it is practical to cool the target surface by providing a cooling channel below the target (not shown). The figure also shows the preferred embodiment with the target ring and the emitter ring rotating in opposite directions 696.

Figure 12:
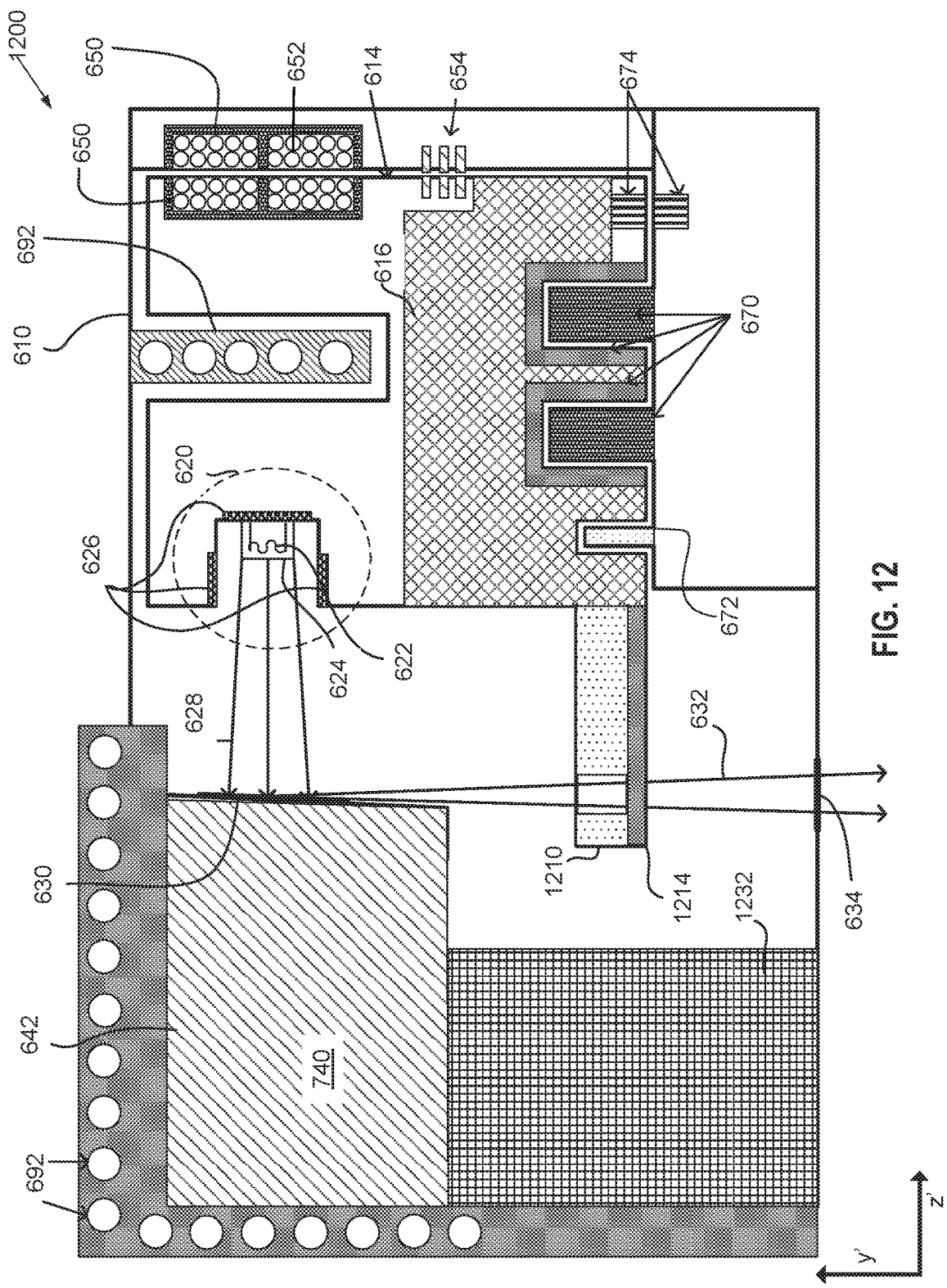
FIG. 12 schematically presents a cut through a plane y'-z' of the X-ray generation sub-system of FIG. 5, with a fixed target ring and a magnetically levitated emitter ring, the emitter ring further supporting collimator elements and optionally beam filter elements for the X-ray beam(s) generated at the target.

FIG. 12 illustrates 1200 the use of a X-ray beam collimators 1210. The emitter ring 614 in such a configuration presents a set of collimators 1210, one per emitter in one embodiment, such that the lateral and longitudinal extends of the X-ray beam (dimensions x' and z' respectively in FIG. 5) are controlled per design parameters. The collimator lateral aperture may be shaped accounting for the system geometry such that the X-ray beam projection through the system is limited to an imaging field-of-view of radius $R_M$, for example (FIG. 2). Similarly, the collimator(s) is shaped so that the primary beam is projected onto the radiation detector with respect to the longitudinal direction z, with no or tightly controlled beam projection beyond the active detector edges (substantially with respect to axis z, z'). If desirable for a specific system design, collimator(s) assembly may also comprise filter plate(s) 1214 appropriate for specific spectral beam shaping for specific applications. It is understood that the resulting beam dimensions and filtration may be different for different radiation emitters provided on the emitter ring. An opening within the element enables un-obstructed progress of the X-ray beam through the collimator aperture. Thus the lateral and z-extends of the X-ray beam can be limited within the vacuum envelope. The figure also illustrates schematically the use of an insert with cooling channels 692 affixed on the vacuum envelope to define substantially thermally separated zones within the vacuum envelope, and thus enabling the use of power-over-gap technology (elements 650) and power conditioning units (not shown) within the cooler vacuum envelope volume thus defined. It is understood that a collimator assembly could as well be provided on the V-shaped or U-shaped mechanical assemblies 880 of the straddle design shown in FIG. 8.

Figure 13:
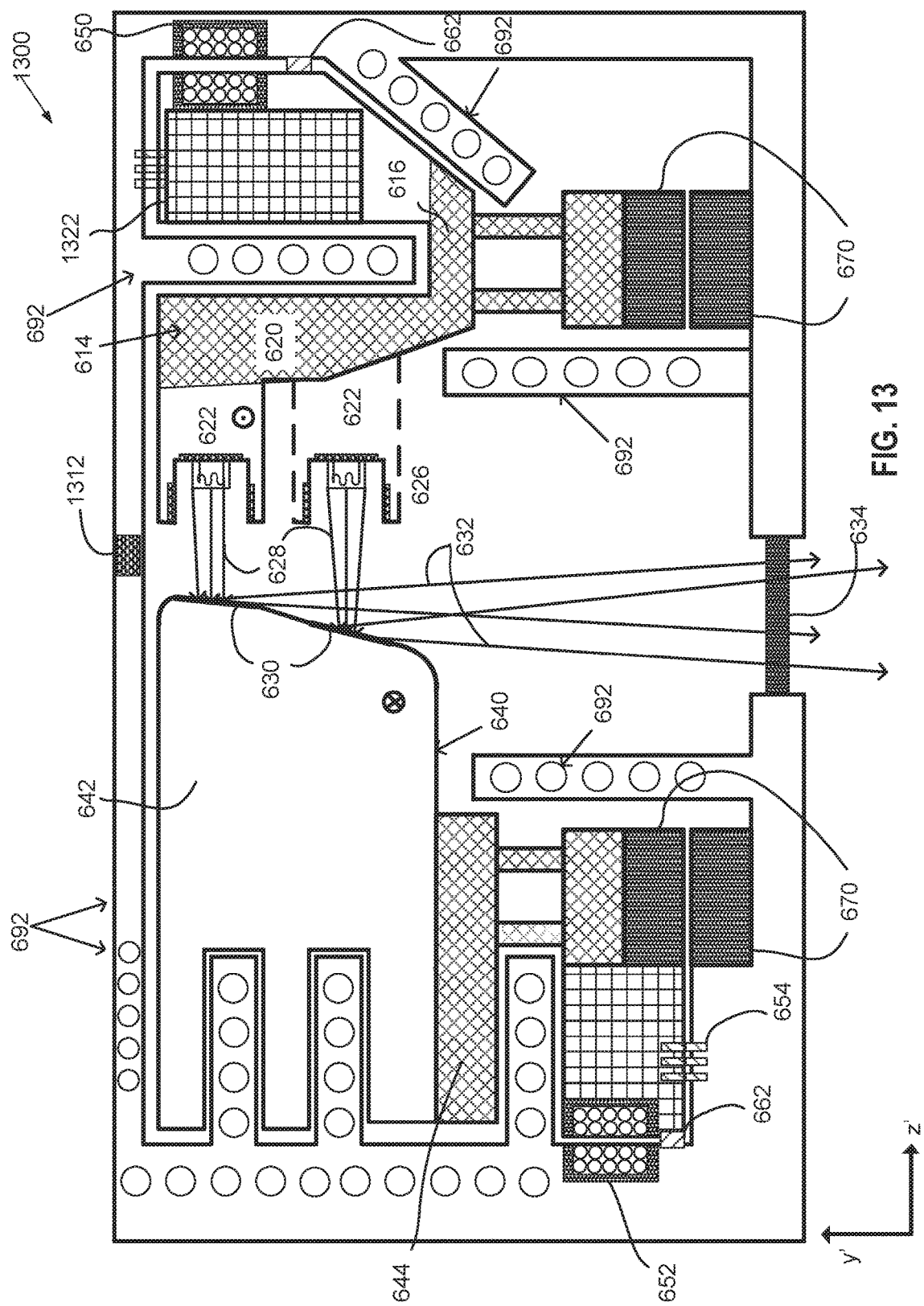
FIG. 13 schematically presents a cut through a plane y'-z' of the X-ray generation sub-system of FIG. 5, additionally showing two emitters offset with respect to their radial distances from system rotation axis z, and two associated target rings.

In FIG. 13, another embodiment of a dual-ring radiation system for multi-source CT is presented 1300, where the emitter ring 614 is provided with a multiplicity of electron beam emitters 622, a subset of the emitters being located at various radii from the system isocenter axis z (110 in FIG. 1). The target ring 640 presents an extended target generally along the y' direction (FIG. 5), or, as shown in the figure, a plurality of target annuli 630 at various radii. It is understood that the plurality of targets may be made of the same, or of different high-Z materials, as directed by the application needs. Further, it is understood that the target angle is a parameter of the design. In CT, a target angle of seven degrees is often retained, although system with a large z-extend beam illumination employ X-ray sources with larger target angles. In an embodiment using two or more target radii, the target at the various radii may be designed to present different angles to the electron beams of the various emitters. The target(s) angle (with respect to axis y') may be the varied as shown in the figure; a shallower angle with respect to the x'-y' plane leading to a higher spatial resolution with respect to the z-dimension in specific applications. The radially offset emitters may also be offset azimuthally (i.e. in central angle).

Vacuum envelope vacuum levels sufficient for the proposed design(s) were achieved by EBT over larger envelope volumes than those proposed in the present document. It may be desirable to provide a vacuum pump to maintain vacuum levels. FIG. 13 shows schematically a vacuum pump port 1312 into the vacuum chamber (the vacuum pump not shown).

Figure 14:
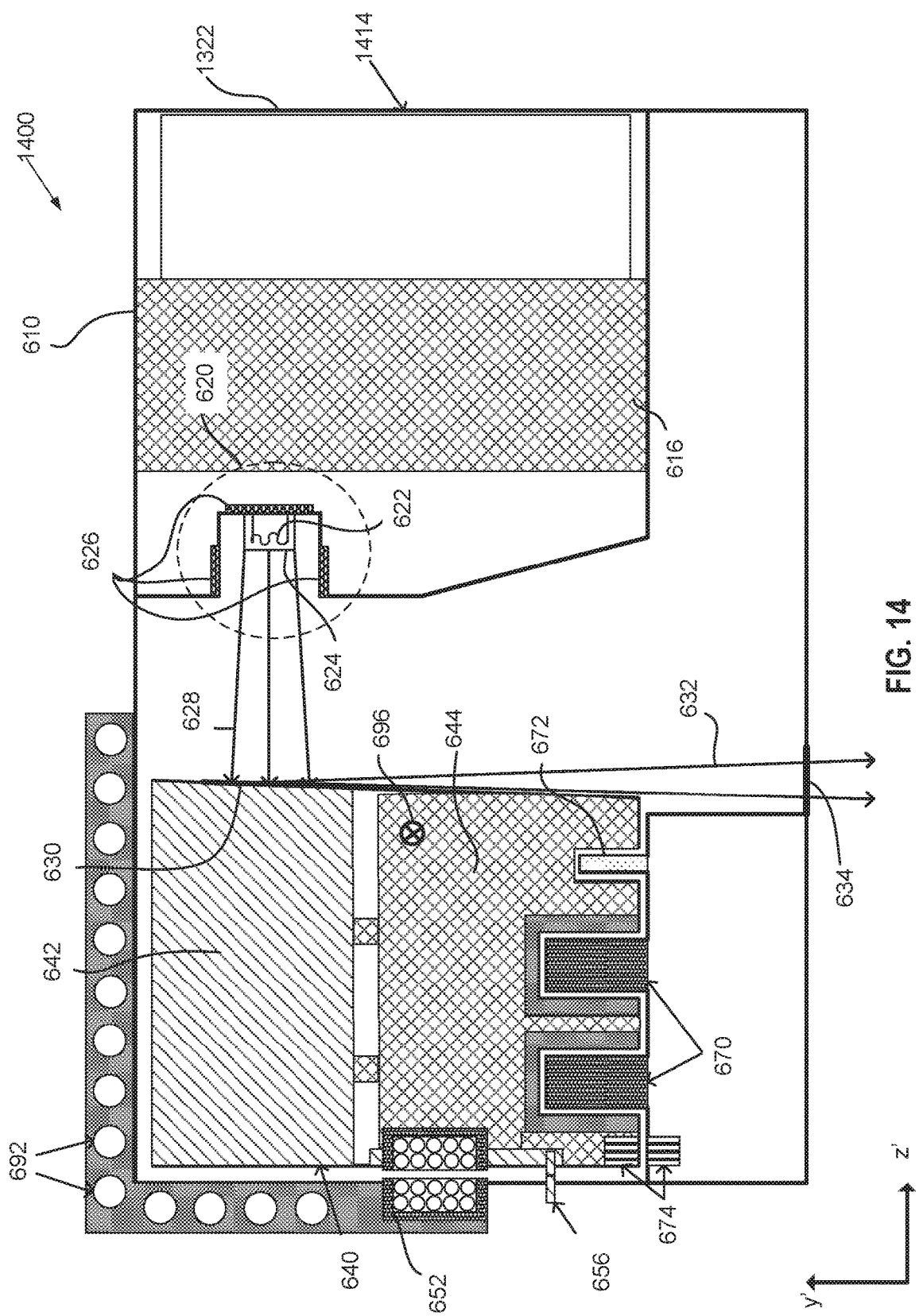
FIG. 14 shows a cut through a plane y'-z' of the X-ray generation sub-system of FIG. 5, with a fixed emitter ring and a magnetically levitated rotating target ring, in an arrangement suitable when using a high number of emitters or arrays of sources on the source/emitter support structure.

FIG. 14 presents 1400 an embodiment particularly adapted to the use of a large number of electron beam emitters, or arrays of emitters, with a high number of electron beam emitters 620 being attached to a non-rotating emitter ring/flange 1414 and facing a rotating target ring. In one such embodiment, the system presents a magnetically levitated target ring and an emitter ring fixed with respect to the vacuum envelope; in one such embodiment, the vacuum envelope is further mounted on a gantry and rotated around the patient/object to be imaged. In a limit case, the emitter structure presents as many emitters azimuthally as the number of desired CT projections around the gantry bore/central opening circumference.

Figure 15:
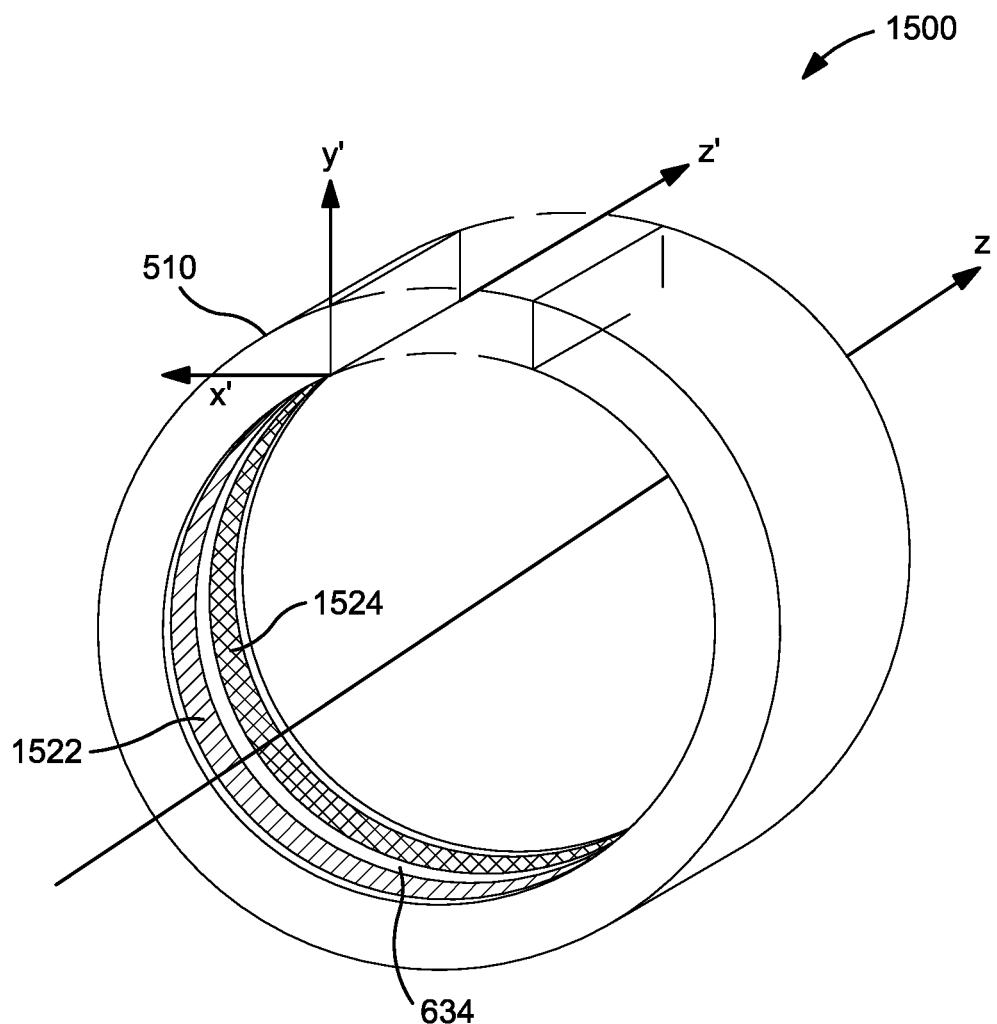
FIG. 15 presents schematically a three-dimensional perspective view of a CT system per the present invention with a dual-ring X-ray source system in a vacuum envelope and two stationary detector arrays external the vacuum envelope, the detector rings being separated by a gap along the z dimension to allow X-ray illumination therethrough.

FIG. 15 presents schematically 1500 a three-dimensional perspective of a dual-ring multi-source CT system per the present invention, wherein the detector is configured to be stationary and substantially mounted on the interior surface of the vacuum envelope tori 510. In one embodiment, the radiation detector covers an azimuthal angle substantially equal to 360 degrees. In one embodiment, the radiation detector is split into two annular surfaces 1522 and 1524 presenting an aperture between them (with respect to z) substantially coinciding with X-ray window 634 and lateral support elements. This aperture allows X-ray beams associated to the plurality of radiation sources to pass through with minimal additional filtration and to image the patient or object placed in the CT system. In another embodiment, the active detector surface is not split, but the cells that are exposed by the primary detector on the backside are designed to enable filtration and radiation passage therethrough.

Figure 16:
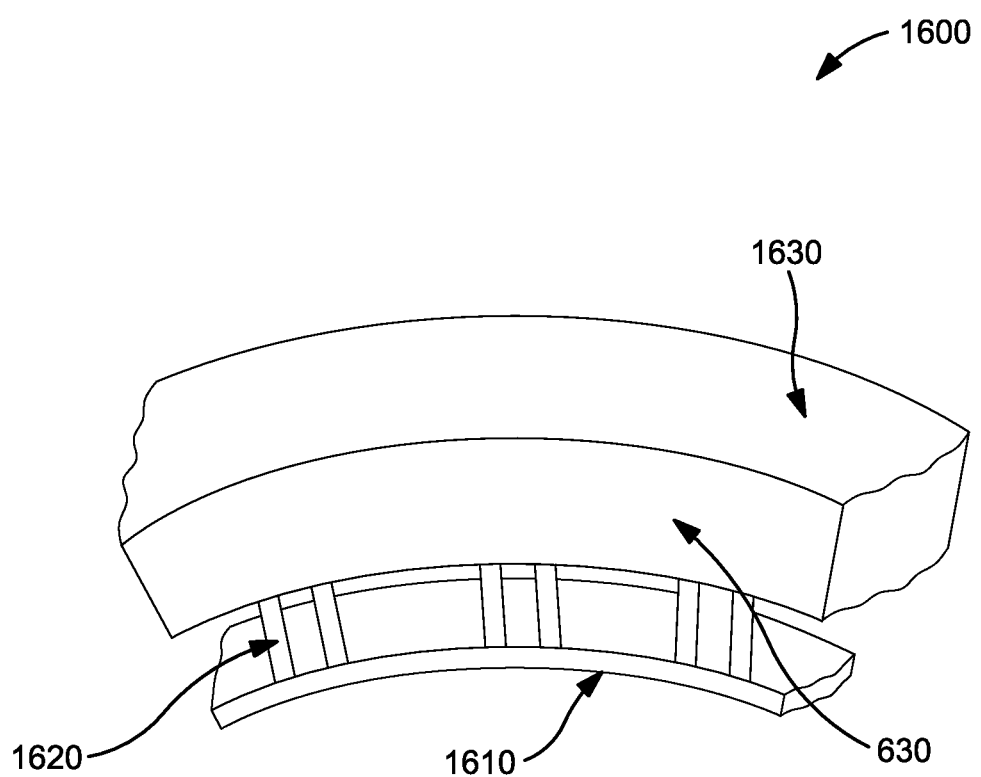
FIG. 16 presents a three-dimensional perspective view of a structural design for increased thermal shielding of the magnetic levitation and magnetic motor elements from the X-ray target and target-emitter vacuum interface.

FIG. 16 schematically presents a perspective view 1600 of a structural design for increased thermal shielding of the magnetic levitation and magnetic motor elements from the X-ray target. Here the target 630 and target backing elements 1630 are mounted on a ring/arc structure, which is attached to the support ring structure 1610 through periodically arranged structural pillars 1620, made of a material relatively refractive to heat (Molybdenum; or ceramic alloys, for example). This, in conjunction with the relative proximity of the target material to the vacuum envelope-mounted cooling elements, reduces the transfer of heat to the support ring structure.

Figure 17:
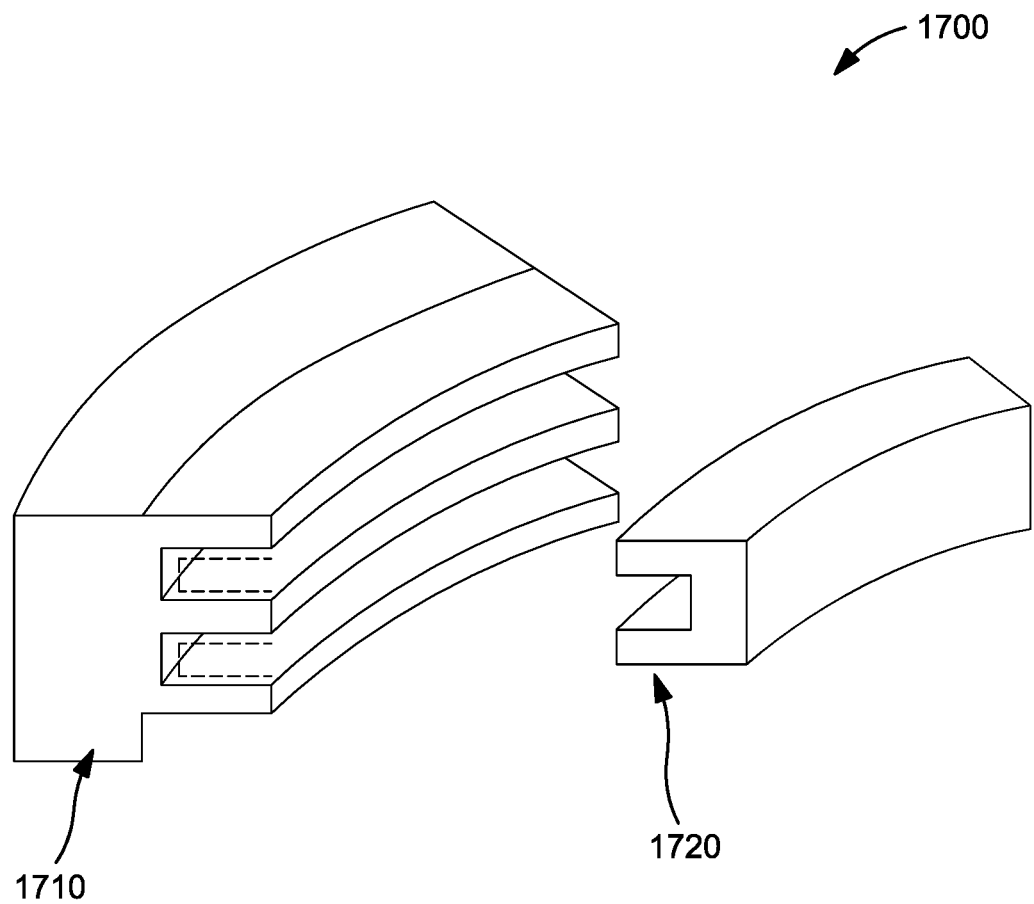
FIG. 17 shows a three-dimensional perspective schematic of heat exchange fins that can be mounted on a rotating target ring to increase radiative thermal exchange between the target ring and the fixed vacuum envelope structure, a design facilitated by the use of target ring set at ground electric potential.

FIG. 17 schematically shows 1700 a perspective schematic of heat exchange fins 1720 that can be mounted on the back side of the target ring to increase radiative thermal exchange capabilities from the target ring to the matching fixed vacuum envelope structure 1710 and the environment, as is known in the art. This design is facilitated in an approach where the target ring 1720 is maintained at ground potential, thus enabling smaller tolerances between the fixed and rotating heat exchange components.

Figure 18:
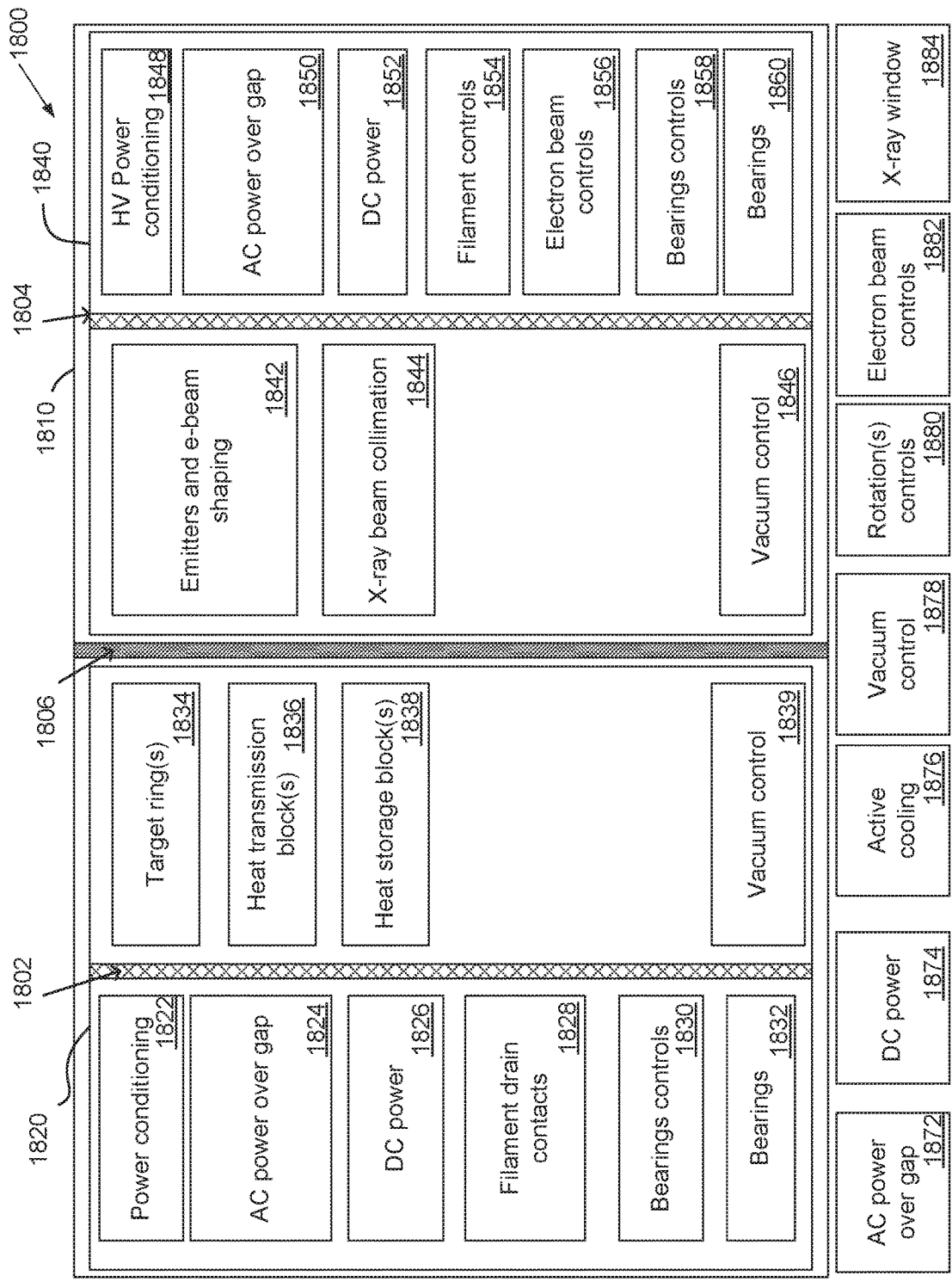
FIG. 18 presents in diagrammatic form the functions of various sub-system components, several of them optional depending on embodiments.

FIG. 18 presents in block-diagram form 1800 various components and functionalities of a multi-source CT imaging system radiation generating system according to embodiments of the present invention. It is understood that some elements are not mentioned, and some elements are optional. Two sub-systems are provided within a vacuum envelope 1810, and interface at the general area/volume 1806 within the vacuum envelope: (1) an emitter ring sub-system 1840, right, and (2) an X-ray target ring sub-system 1820, left. Each of the two subsystems presents sub-areas that are shielded from the heat generated by the electron beam generator and the electron beam impacting on the target, respectively, by heat shields 1802 and 1804. The emitter ring 1840 has an emitters and electron beam shaping elements 1842, X-ray beam collimation element 1844, and vacuum control 1846. Shielded from the heat of the emitter-target interface area are high-voltage power conditioning element 1848, AC power over gap elements 1850, DC power element 1852, filament controls 1854, electron beam controls 1856, bearing controls 1858, and bearings 1860. On the target ring side figure the target ring(s) 1834, heat transmission block(s) 1836, heat storage block(s) 1838, and vacuum control 1839; and shielded from the heat generated at the target(s) and emitter-target(s) interface zone, power conditioning elements 1822, AC power over gap 1824, DC power 1826, filament drain contacts 1828, bearing controls 1830, and bearings 1830. Additional sub-systems external to the vacuum envelope enable operation of the X-ray CT system as described in the present document, such as AC power over gap block 1872, DC power block 1874, active cooling 1876, vacuum control 1878, rotation(s) controls 1878, electron beam controls 1882, X-ray window element(s) and filter(s) 1884. In the diagram, the bearings are shown symbolically as a boxes 1832 and 1860 sub-system component; they could be one of a mechanical bearing; a magnetic levitation bearing; a liquid-metal bearing.

Figure 19:
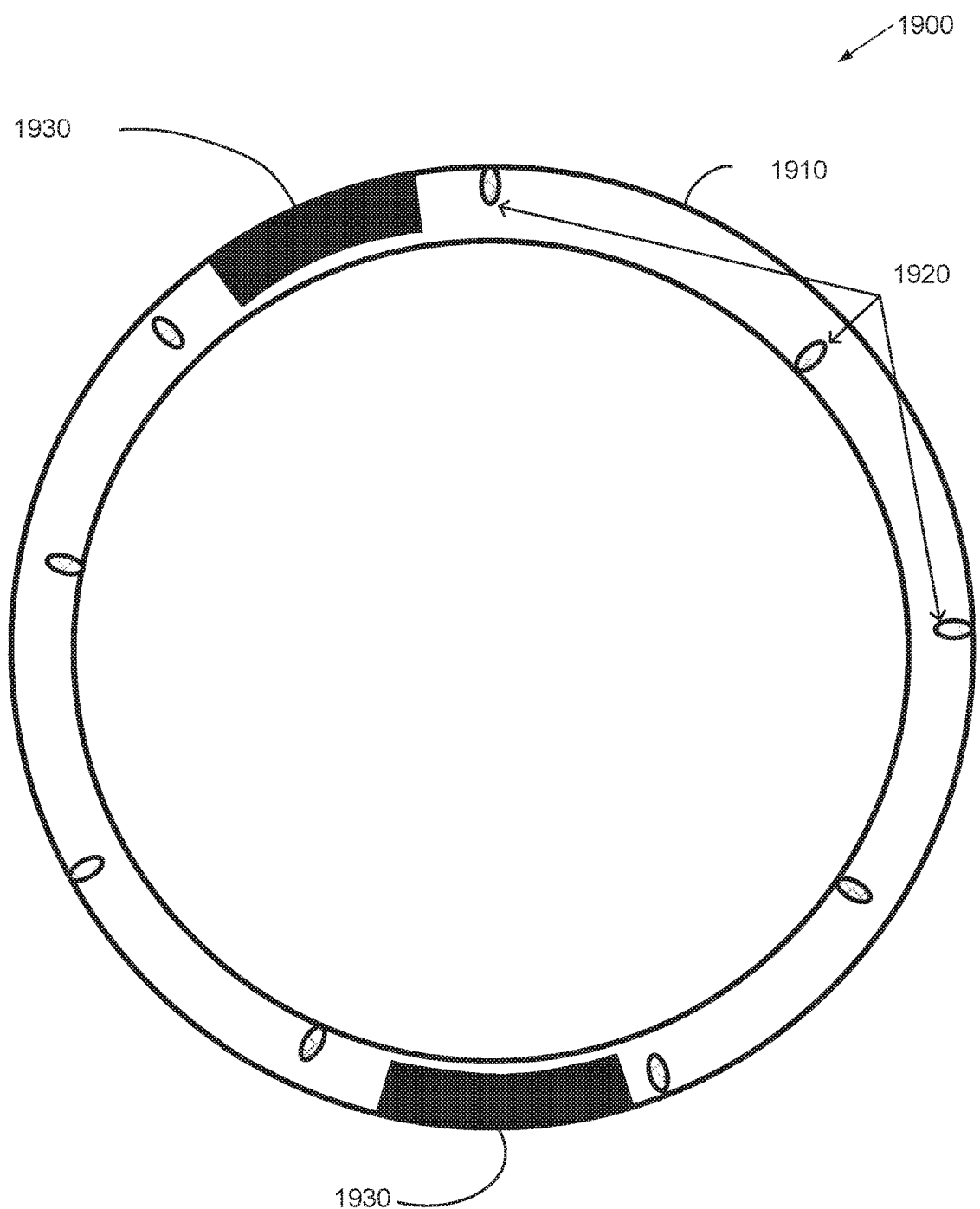
FIG. 19 is a face view of the x-y plane of an emitter ring, showing nine emitters distributed around the ring at a multiplicity of radii and schematically indicating spaces for the power conditioning components onboard the emitter ring.

FIG. 19 schematically depicts a face view 1900 of the x-y plane of an emitter ring 1910 and shows nine emitters 1920 distributed around the ring and schematically indicates spaces for the power conditioning components 1930 onboard the emitter ring. In a practical implementation, the power conditioning components lie below one or more thermal shielding layers. As shown in the figure, in an embodiment the emitters optionally are radially offset from one another and thus the associated electron beams strike the anode target(s) at a different radius from isocenter.

Figure 20:
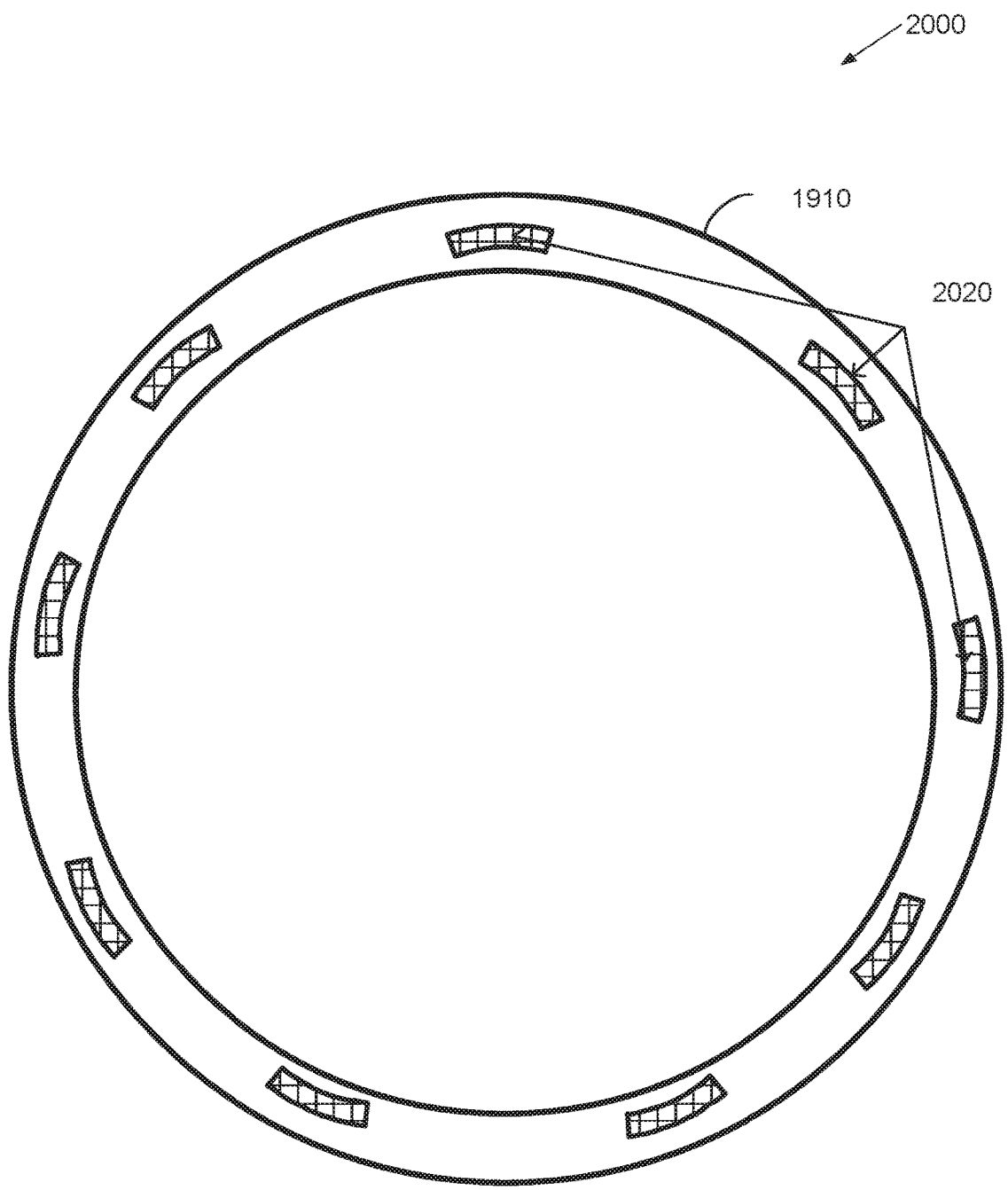
FIG. 20 depicts a face view of the x-y plane of an emitter ring similar to that of FIG. 19 except that the nine individual X-ray source emitters are replaced by nine arrays of X-ray source emitters.

FIG. 20 schematically presents 2000 an embodiment similar to that of FIG. 19, except that the individual emitters 1920 have been replaced by arrays of radiation emitters 2020. In another embodiment, not shown, emitters on the ring could be provided in the form of a mix of individual emitters and emitter arrays.

Figure 21:
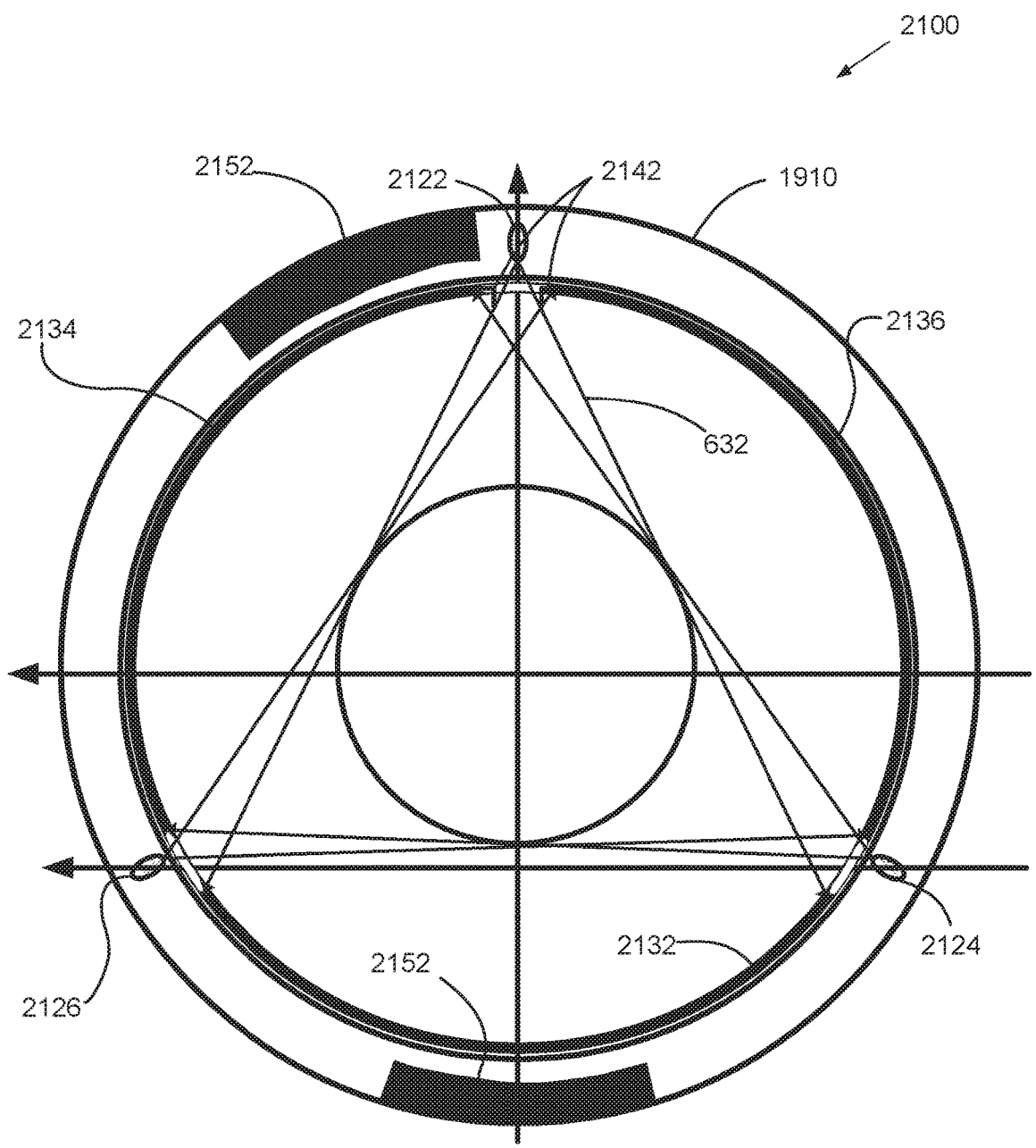
FIG. 21 depicts a face view of the x-y plane of an emitter ring, showing three emitters distributed around the ring and also describes the traces for three detector arrays, each one associated spatially with one emitter on the emitter ring, for a system operating at source ring angular velocity $\omega_s$ and detector drum angular velocity $\omega_d$ such that $\omega_s = \omega_d$.

FIG. 21 depicts 2100 a face view of the x-y plane of an emitter ring 1910 and shows three emitters 2122, 2124 and 2126 distributed around the ring and also depicts the traces for three detector arrays 2132, 2134 and 2136, each one associated spatially with one emitter on the emitter ring. In such a system embodiment, the detector arrays are mounted on a separate gantry/drum unit, and rotate within the volume defined by the vacuum envelope surface generally at smallest radius from the system main axis z. The detector drum unit rotates synchronously with the emitter ring. In a medical imaging system geometry, it is possible to have three separate imaging chains (emitter and detector), each covering laterally the entirety of the measurement field cross-section in the plane of the figure, the projections not overlapping on the detectors. The X-ray beams 632 are appropriately collimated laterally (as per FIG. 12 for example) by collimators 2142 associated with emitter 2122 and similar structures associated with emitters 2124 and 2126 (not shown) so that no beam overlap occurs on any of the detector and the radiation fields from the various emitters are limited to the imaging field-of-view of radius $R_M$. In such a configuration, the detectors (mounted on a separate gantry, not shown) rotate synchronously with the emitter ring, so that the relative position between the projected beams and the respective detector arc/arrays is maintained.

Figure 22:
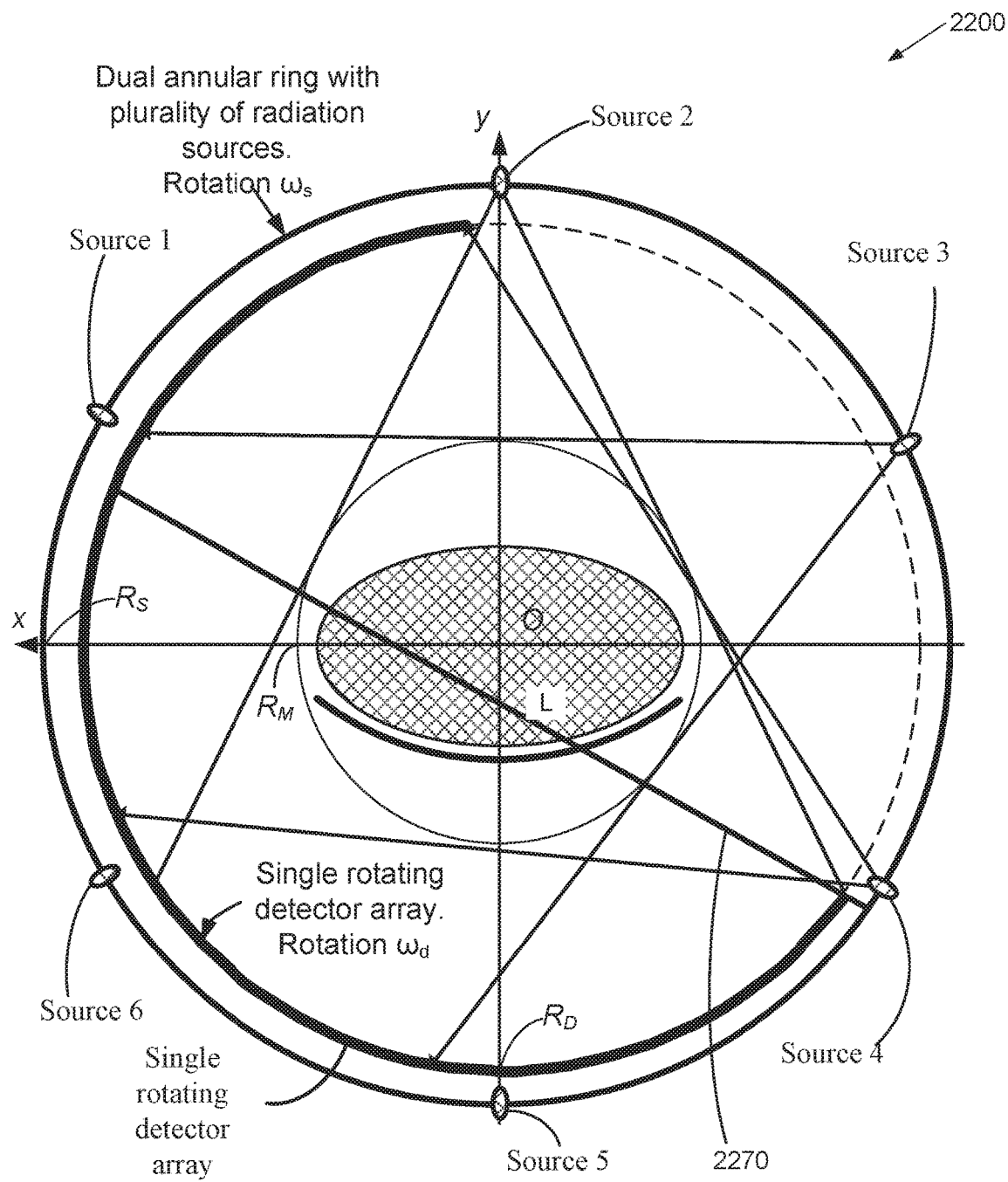
FIG. 22 schematically represents a system as in FIG. 4, wherein the drum supporting several conventional rotating anode-stem X-ray tubes (or individual fixed-anode tubes) has been replaced by a dual annular ring radiation source sub-system per the present invention.

FIG. 22 schematically represents 2200 a system as in FIG. 4, wherein the drum 402 supporting several conventional X-ray tubes has been replaced by a dual annular ring radiation source system per the present invention.

Figure 23:
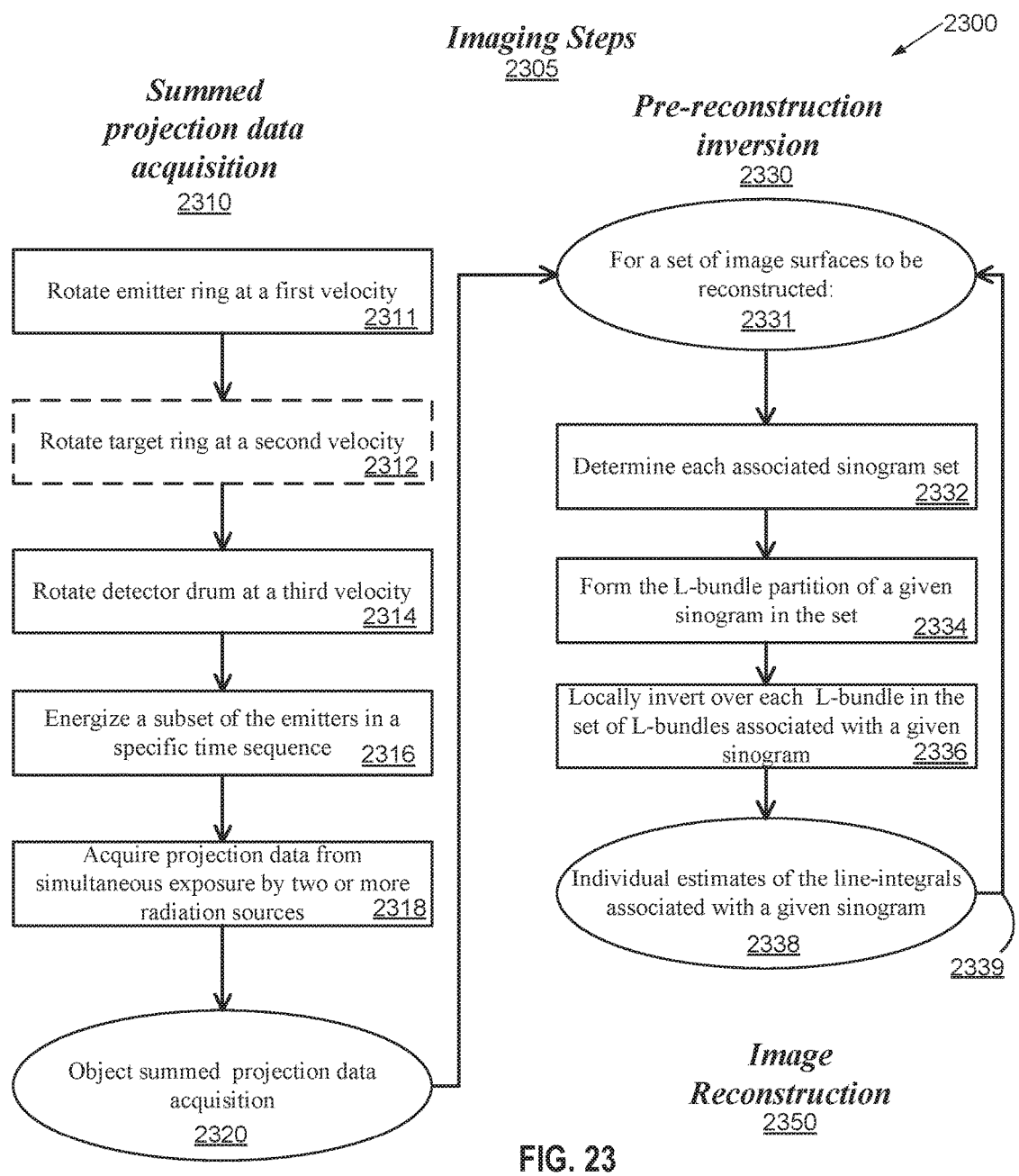
FIG. 23 presents in flow chart form imaging steps for a multi-source CT system with dual-ring source sub-system per the present invention.

In FIG. 23 major steps associated with the use of a multi-source CT system per the present invention are described in flow-chart form 2300. The three major steps are (1) (summed) projection data acquisition 2310, (2) pre-reconstruction inversion 2330, and (3) image reconstruction 2350. In summed projection data acquisition (1), an object or patient to be imaged is positioned in or nearby the imaging gantry, the steps include rotating the emitter ring at a first angular velocity $\omega_s$ 2311, optionally rotating the target ring at a second velocity 2312 when such rotation is provided for in the system embodiment, and rotating the detector drum at a third angular velocity $\omega_d$ 2314 related to the source angular velocity $\omega_s$. In a particular embodiment, the sources ring and detector drum angular velocities are related through the equation:

$$\omega_d = K \times \omega_s$$

where K is the number of sources simultaneously in view of the detector. Additional data acquisition steps include energizing a subset of the radiation emitters at a given moment in time, as a function of the relative positions of the source ring and detector drum, 2316. Thus, summed projection data 2320 for a given object or patient to be imaged are acquired, step 2318, corresponding either to one particular image surface to be reconstructed, or to a volume of tomographic slices to be reconstructed for the object/patient under interrogation. The second major step (2) is pre-reconstruction inversion, 2330. For a given image surface 2331 to be reconstructed for which sufficient data was acquired in major step (1), the set of associated geometric individual line-integrals through the object is determined, 2332; the set of associated line-integral estimates—the sinogram—constitutes the input to any existing CT image reconstruction algorithm. Thus, it is desirable to estimate the individual line-integrals projection value for the sinogram from the summed data. In principle, this estimation could be performed together with the image reconstruction step, as a novel combined inversion problem. Here, for the clarity and simplicity of description, the details of the pre-reconstruction inversion process are given separately from the image reconstruction steps. For each geometric line L associated to the output, desired sinogram, is constructed the L-bundle(L) 2334 set for L: The L-bundle of L consists of those geometric lines that may figure in a summed measurement involving line L [this concept is further described in the context of FIGS. 23 and 24]. The L-bundle comprises a limited number of geometric lines, the exact number depending on the nominal source central angle $\Delta\theta_S$ and the geometry of the system, as described below. As is discussed further below, at step 2336 it is in general possible to locally invert the set of equations associated to the L-bundles, thus obtaining estimates for the individual line integral projection values, that is, the part of the sinogram 2338 that pertains to the L-bundle of L. The pre-reconstruction inversion method then iterates over lines L in the sinogram at step 2339. From the sinogram, CT image reconstruction proceeds as is known in the art, through a filtered-backprojection method or an iterative or algebraic method. Rebinning of the fan-beam projection data into parallel beam is often performed as an initial step towards image reconstruction; additional calibration and corrections steps are typically applied, as is known in the art.

Figure 24:
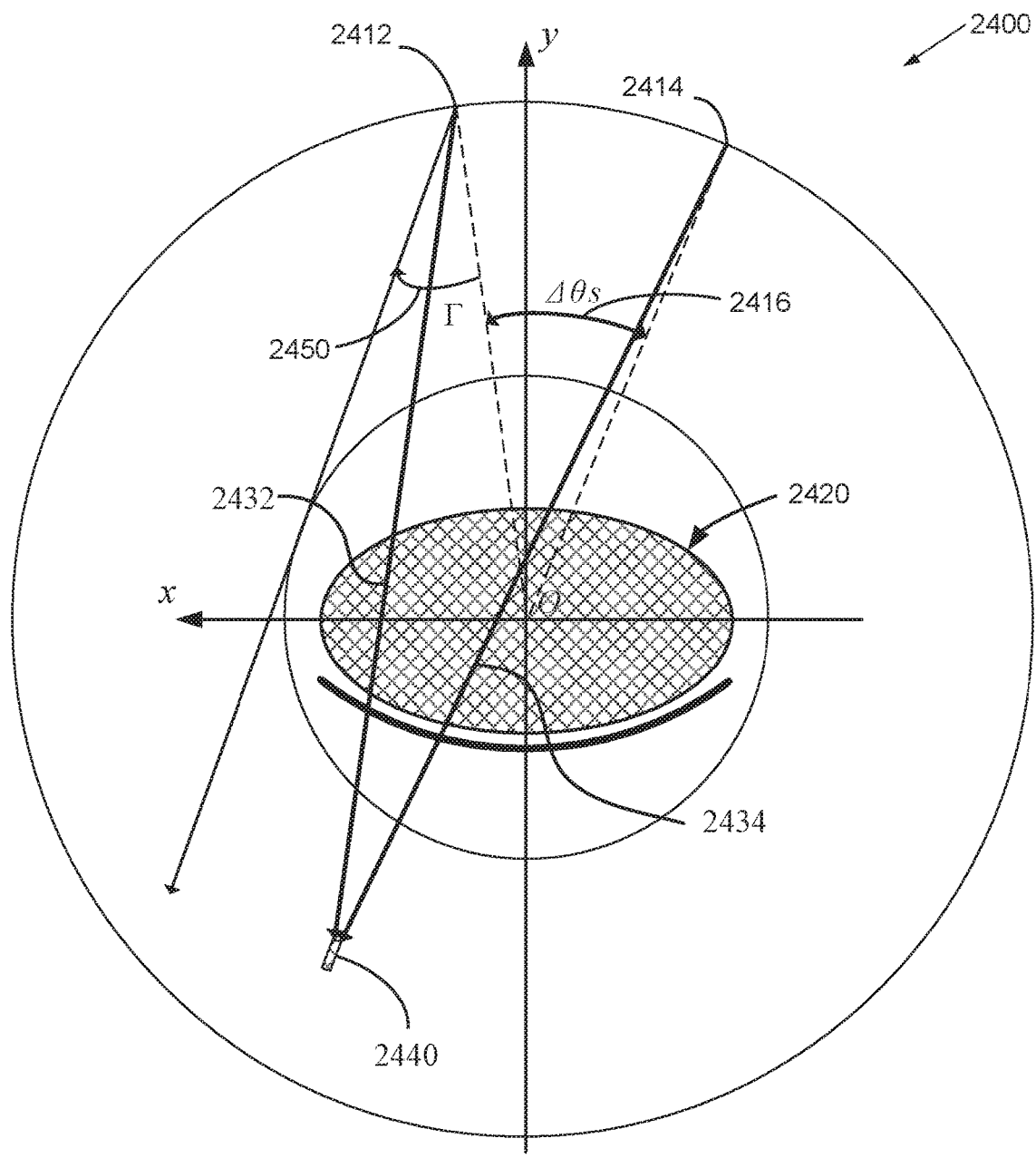
FIG. 24 describes the acquisition of summed projection data of an object in a multi-source CT system.

In FIG. 24, the acquisition of summed projection data is illustrated 2400 for a system with two sources simultaneously active at a given instant in time. The projection data corresponding to line-integral path $L_1$ 2432 and line integral path $L_2$ 2434 through the object 2420 are summed together at the detector cell 2440. The summed measurement acquired at detector cell 2440 is a function of the integrals of the linear attenuation coefficients along the two paths 2432 and 2434, as well as the characteristics of the sources (not shown) generating radiations at or near points 2412, 2414 respectively. Thus the summed measurement can generally be expressed as:

$$I = \int_{Energies\ E} \left\{ I_{0,1}(E)\exp\left(-\int_{Path\ L_1} \mu(l, E)\,dl\right) + I_{0,2}(E)\exp\left(-\int_{Path\ L_2} \mu(l, E)\,dl\right) \right\} dE, \quad 5$$

where $I_{0,1}(E)$ and $I_{0,2}(E)$ respectively describe the source spectra and thus the intensities that would be summed in the absence of any object in the paths $L_1$ and $L_2$.

Figure 25:
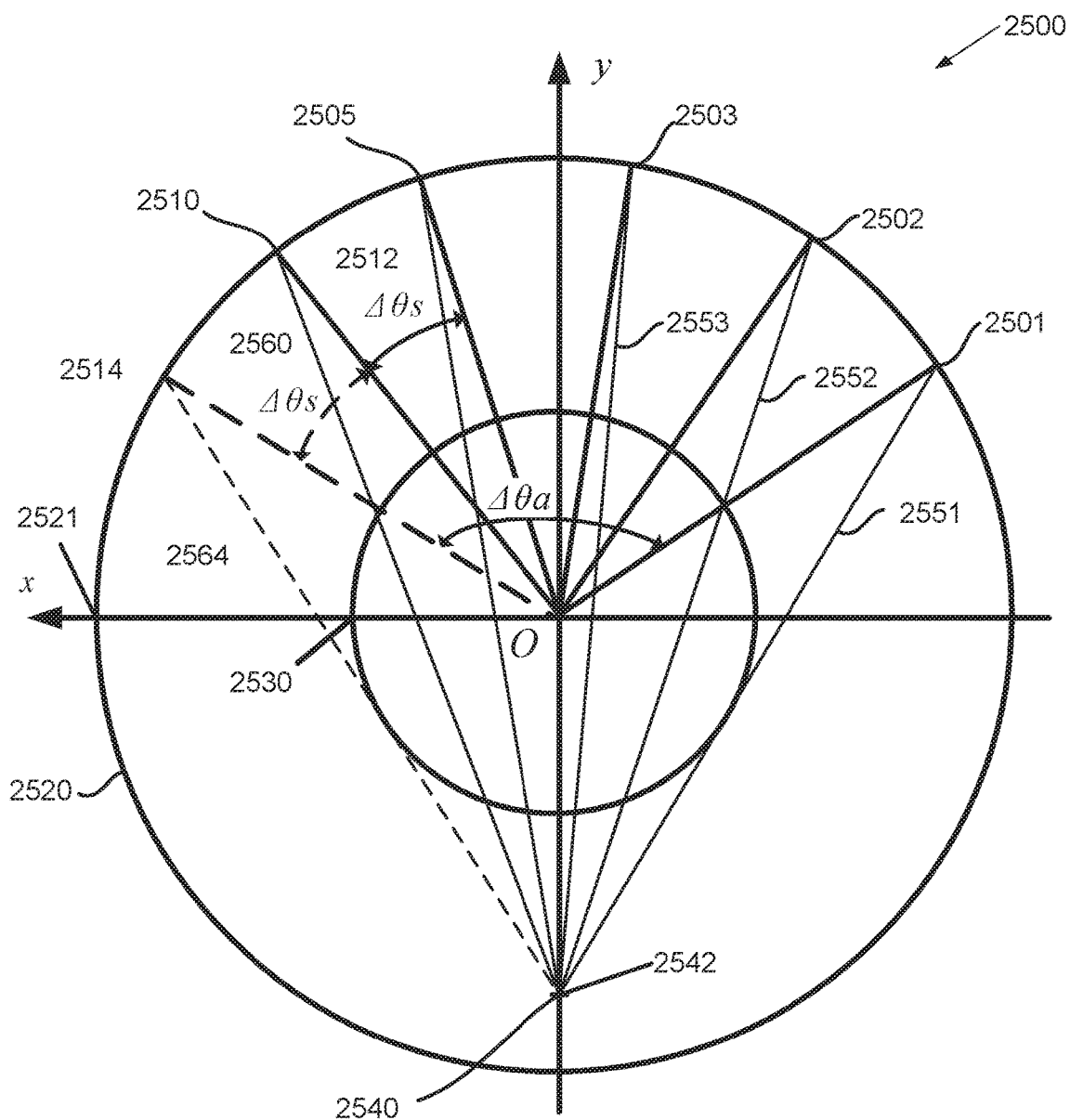
FIG. 25 presents a limit condition for the acquisition of summed projection data of an object in a multi-source CT system.

FIG. 25 describes 2500 the acquisition of summed projection data for a multi-source CT system comprising up to $N_a$ simultaneously active sources 2501, 2502, . . . , 2510. The figure describes a special case condition, where the nominal source separation central angle $\Delta\theta_S$ 2512 is such that the central angle $\Delta\theta_a$ sustained by two lines originating on a detector cell d 2540 at radius $R_d$ 2542 from isocenter O and tangent on either sides to the field-of-view of radius $R_M$ 2530 is equal to:

$$\Delta\theta_a = N_a \times \Delta\theta_S.$$

Consider an embodiment of a multi-source computed tomography system with $N_S$ equispaced sources mounted on a rotating gantry, with (minimal) central angle $\Delta\theta_s$ between two adjacent sources. At any given instant in time, a subset of at most $N_a$ sources is active and illuminating the object through the flying detector extended aperture. Thus the central angle between the two extreme sources in view of the detector is $(N_a-1)\Delta\theta_s$.

Further, consider such a system, with $\omega_d = \omega_s$. Then the subset of sources that can be activated to illuminate the object is defined by the spacing between sources and the "aperture" extent. It is understood that such a system can be also directly implemented with a total number of sources limited to those sources that are within the "aperture" and simultaneously in view of the detector. Such a system can thus be considered as having a single rotating gantry.

A condition for local inversion of the pre-reconstruction problem can be formulated as follows. As illustrated in FIG. 25, for any detector cell d 2540 at a distance $R_d$ 2542 from isocenter O, (wherein the distance d is the minimum of all the detector cell distances to isocenter), suppose the central angle $\Delta\theta_a$ between the two projection points $P_1$ 2501 and $P_2$ 2514 corresponding to the intersection of the two lines originating at detector cell d and tangent to the measurement field-of-view of radius $R_M$ is such that:

$$N_a \Delta\theta_S \geq \Delta\theta_a. \quad (*)$$

When condition (*) is satisfied, then $l=\text{Card}(L\text{-bundle}(L)) \leq N_a + 1$ where $l=\text{Card}(L\text{-bundle}(L))$ designates the cardinality of the set of lines through the field-of-view of radius $R_M$ for the L-bundle associated to geometric line L 2553. Also, at most $N_a$ line integrals contribute to a single summed projection measurement; and since each line integral L is measured $N_a$ times from one end (one intersection of L with the source trajectory circle), once per source, the L-bundle system of equations for a given line L in the L-bundle(L) consists of $N_a$ rows in at most $N_a$ unknown. Further, the total number of measurements $N_m$ involving any line in the the L-bundle(L) is $$N_m = l + (N_a - 1);$$

Accordingly, the determination of the line-integral estimates for all lines in the L-bundle of L can be accomplished by inverting a system of $N_m$ equations in $l \leq N_m$ unknown; it is thus is locally invertible. In the general geometry case, (*) can be written as:

$$N_a \Delta\theta_s \geq 2\ \text{asin}\left(\frac{R_M}{R_d R_s} \times \left[R_s \cos(\Gamma) + \sqrt{R_d^2 - R_M^2}\ \right]\right). (*')$$

This is illustrated in FIG. 25 for $N_a = 5$.
When $R_d = R_s$, then (*') becomes:

$$N_a \Delta\theta_S \geq 4\Gamma. (**)$$

The fact that then at most $N_a$ line integrals contribute to a single summed projection measurement can also be seen as follows. A given line-integral L is part of a summed measurement when and only when one of the $N_S$ sources intersect path L on the source trajectory (at one, fixed, intersection of L with the source path). The other $(N_S-1)$ sources define $(N_S-1)$ lines/paths through the object that define the L-bundle of L. Only these lines can contribute to a summed measurement involving line L (again, for one of the two intersections of line L with the circle of the sources trajectory being chosen and considered fixed).

Given that the local system of equations has as many or fewer unknowns than measurements, the system is invertible. Even if the system is singular or near singular, it can be regularized using known regularization methods such as Tikhonov's to yield a local estimate for the individual line integrals in the L-bundle. The condition of equation (*) can be expressed by stating that the L-bundle for any line L consists of at most $N_a$ paths intersecting the object within the measurement field-of-view of radius $R_M$.

The above reasoning can be extended to the case where the number of simultaneously active sources is less than $l=\text{Card}(L\text{-bundle}(L))$, with no restriction on $\Delta\theta_s$, as will be seen below.

If the multi-source CT system also has a radiation detector mounted on a flying gantry, as described in FIG. 4 and FIG. 22, also called a "flying detector," then additional configurations apply (other than $\omega_s = \omega_d$). Let the flying detector rotate at angular velocity $\omega_d$. The flying detector gantry may be mechanically supported; or magnetically levitated. In operation, the product $\omega_s \times \omega_d$ can be positive or negative. In operation, the detector and source angular velocities may satisfy any magnitude relation: $\omega_s \leq \omega_d$; or $\omega_s > \omega_d$. In particular, the case of an emitter gantry angular velocity greater than that of the flying detector angular velocity is specifically considered. These configurations are now examined in more details, keeping in mind that in this document a multi-source CT system in a typical medical imaging geometry is retained for specific illustration. The radiation source(s) are mounted at a radius $R_s$ from the system isocenter ($R_s = 570$ mm). The imaging field-of-view has a radius $R_M$ from the system isocenter ($R_M = 250$ mm). Thus, the maximum fan-angle for a corresponding 3thd-generation system is:

$$\Gamma = \text{asin}\left(\frac{R_M}{R_s}\right).$$

In the following, the specifics of preferred embodiment(s) of the new multi-source CT system of the present invention are defined through the specific conditions below.
(C.1) As in a 4th-generation CT, the detector is (preferably) mounted on an array centered on the system isocenter.

[However it is not necessarily stationary, as is the case in 4th generation systems.] The central angle sustained by the detector arc is substantially equal to ($\pi+2\Gamma$). Other detector geometries are possible.

(C.2) It is convenient for simplicity of exposition [but not necessary] that the detector radius be equal or approximately equal to the source radius: $R_d=R_s$. In a practical embodiment of a system with a flying detector, $R_d \lesssim R_s$.

(C.3) The $N_s$ X-ray sources are mounted equidistributed in central angle $\Delta\theta_s$ and the subset of $N_a$ sources in view of the detector sustains a central angle less or equal to ($\pi-2\Gamma$). This condition, together with (C.1), is practical as it implies that the sources projections can cover the entire field-of-view to be measured without truncation. In such a configuration, the sources and the detector can be essentially co-planar, a condition not satisfied by electron beam tomography (EBT).

(C.4) If is the number of projections per 360-degree gantry rotation, then the source central angle $\Delta\theta_s$ is an integer multiple of the projection separation central angle $2\pi/N_v$.

(C.5) It is convenient, but not necessary, that the source separation central angle $\Delta\theta_s$ also be an integer multiple of the detector cell central angle $\Delta\theta_d$ (central angle between two adjacent detector cells). If not, projection data interpolation may be applied in a rebinning step.

A system meeting conditions (C.1)-(C.5) is illustrated in FIG. 22. The multi-source CT system of FIG. 22 has a flying detector with an extended aperture forming a central angle substantially equal to about $\pi-2\Gamma$ radians, and thus up to three X-ray sources simultaneously active with a detector arc extending over substantially $\pi+2\Gamma$ radians. The system's six sources are equally distributed over $2\pi$ radians.

Such a multi-source CT system comprising a "flying detector," where the detector is mounted on its own gantry/drum, separate from the sources, enable substantial temporal resolution gains. Such a mechanical arrangement is shown schematically in FIG. 22. The flying detector substantially consists of two angular ranges: an extended active detector angular range covering a central angle of about $\pi+2\Gamma$ radians, and an extended aperture through the complementary central angle $\pi-2\Gamma$ radians. The extended aperture enables passage of the X-ray beams generated by the sources mounted on the source gantry (or fixed in the laboratory) to expose the patient there through.

A system with $N_s$ equidistributed sources separated on the source drum by a central angle $$\Delta\theta_s = \frac{2\pi}{N_s}$$

as been introduced and discussed previously. The basic design concept is described in FIG. 4, which presents a conceptual diagram for a CT system with two independently rotating gantries, one supporting $N_S$ X-ray sources ($N_S$=5 illustrated), the second an angularly-extended detector arc. FIG. 4 presents an exploded perspective rendition of a multi-source X-ray CT system architecture comprising an X-ray source drum (rotation at angular velocity $\omega_s$) shown there with five tubes; and an independently rotating co-axial detector drum (rotation at angular velocity $\omega_d$), with an extended detector angular range, and a drum aperture permitting X-ray illumination there-through. In operation, the detector drum is situated within, and rotates with respect to, the source drum.

As shown previously, writing $r_\omega=\omega_d/\omega_s$ the maximum temporal resolution relationship that applies for complete angular source sampling is:

$$r_\omega \leq \frac{\Delta\theta_a}{2\pi}N_s. \tag{E5}$$

The potential speed and temporal improvements derive directly from Eq. (E5). It is noted that potential gain speeds apply independently of today's tube technology RPM ratings.

The above architecture described in FIG. 4 still relies on conventional rotating CT rotating anode-stem X-ray tubes. An afferent limitation relates to the sizes of the X-ray tubes and of the power conditioning elements. Alternative CT X-ray source designs have been proposed that have the potential to be synergistic with the new dual-drum CT architecture: In 1979 Maydan, Shepp and Cho presented a concept for an X-ray emitter rotating within a vacuum envelope that also contains a stationary annular anode/target. That specific concept was further developed by Burke et al, U.S. Pat. No. 5,305,363, 1994 who investigated the feasibility of the system of FIG. 6, presenting a magnetically-levitated cathode assembly and a fixed annular anode ring; the cathode ring presenting a single emitter.

That design, which relied on a stationary detector ring, was never implemented as it was susceptible to increased scatter collection (as are all systems in 4th generation geometry), and required the source target plane and the detector plane to be offset with respect to the z-axis (as in Electron Beam Tomography (EBT)), thus introducing a cone-angle problem and limiting the approach's practicality.

However even in these more favorable geometries, using a single emitter would present a power limitation similar to that experienced by EBT: Because the instantaneous power is a function of the relative velocity of the electron beam on the anode target, it is difficult to deliver the necessary beam flux (exposure) to the patient in a single cathode rotation. The traditional 3thd generation CT system architecture presents the advantage of decoupling this electron-beam velocity from the tube rotation velocity around the patient. For illustration, consider a CT tube representative of today's capabilities, with an anode diameter of 20-cm rotating at 180 Hz, and up to 1-A beam current at 120-kVp. These specifications correspond to an electron beam velocity with respect to the target of about 111 m/s. If the tube rotates in 300-ms around the patient at a radius of 57-cm, an exposure of 300 mAs can be delivered. Assuming it possible, a matching beam velocity with respect to the target in the design of Burke et al would take about 32-ms to rotate the cathode a full 360-degrees around the patient, thus delivering about 32 mAs; a factor 10 less exposure per rotation (assuming all other parameters equal: Other operating points may provide optimal flux; however the essence of the limitation—the coupling mentioned above—remains). In the present document a novel multi-source architecture is introduced that:

(1) Provides a plurality of cathodes on a cathode ring rotating within the vacuum envelope;

(2) Optionally provide for magnetic levitation of the target ring itself; and (3) describes use of a flying detector to eliminate the EBT z-offset problem and optimally leverage the power from each emitter on the emitter ring.

It is noted that in general, the system will determine a-priori what set of lines L need to be measured as part of a sinogram associated with a given image to be reconstructed. Actual measured line-integrals can then be grouped in sets under approximation conditions commensurable with the sampling associated with the pre-determined sinogram. That is, the constraints on the projection data acquisition timing and sources arrangements are not to be interpreted exactly, but rather within errors that are acceptable in view of the final sampling as determined by the definition of the set of lines that are to be part of a sinogram; as well as other system parameters such as sampling interval, detector cell apertures, and dose/noise.

Figure 26:
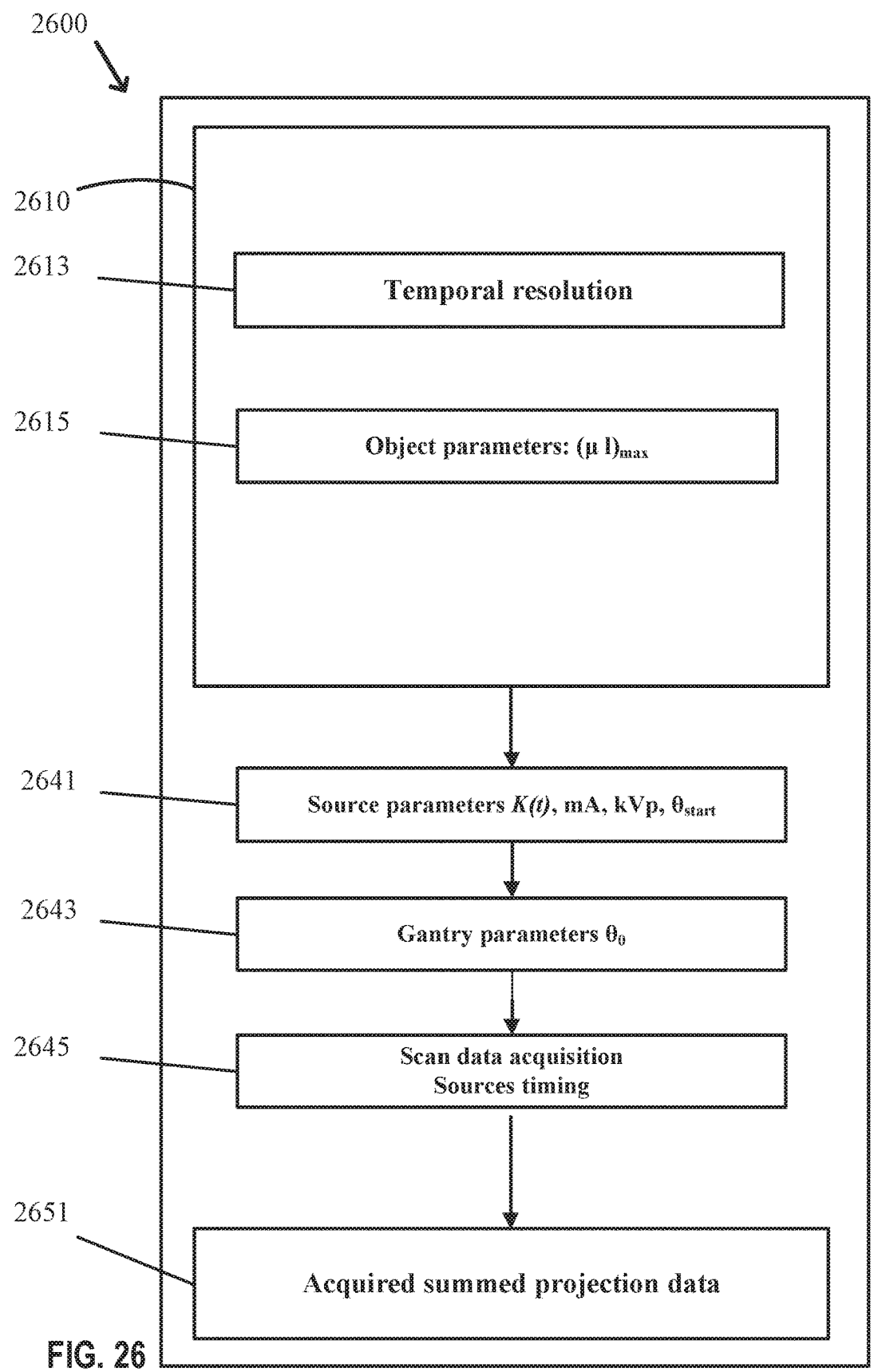
FIG. 26 presents in diagrammatic form imaging parameters selection for a dual-ring dual-rotation multi-source CT system.

In FIG. 26 several multi-source CT system parameters associated with the examination of a patient or object to be imaged are described in flow-chart form, 2600. In a dual-rotation CT system of the present document, the desired temporal resolution 2613, per tomographic slice or as per extent of the imaging area (such as a given organ to be interrogated), together with other information about the object, such as maximum line-integral attenuation 2615 (acquired for example from a "scout" scan or from a prior exam), will help determine key parameters such as detector and source rotation angular velocities, the source activation sequence as well as source parameters including electron beam current ("mA"), peak kilo-voltage, and starting angle $\theta_{Start}$, available on a multi-source CT system for imaging of a given object or patient. In particular, and as will be described further below, sources modulation sequences and/or sources timing sequences 2645 can be pre-determined as a function of the above imaging parameters.

Considering a dual-drum geometry with a flying detector, as in FIGS. 4 and 22, it has been shown (G. M. Besson, Medical Physics 42, 2668 (2015); doi: 10.1118/1.4918328) that for such a system with a total of $N_s$ sources and K sources simultaneously in view of the detector, the flying detector angular velocity ratio with respect to the source drum angular velocity can be as high a:

$$\frac{\omega_d}{\omega_s} = K. \quad (E7)$$

In other words, it has been established that for a multi-source CT system with: $\omega_s < \omega_d$ the maximum effective data acquisition speed-up as compared to a single-source CT system operating at $\omega_s$ is K, where K is the number of sources simultaneously in view of the detector. Accordingly, tomographic data acquisition can also be performed in 1/K the time required by a standard CT system with a one source conventional CT gantry rotating at $\omega_s$ radians per seconds. In a multi-source system operating at $\omega_d = K \times \omega_s$, each line integral path through the object is sampled only once (with quarter offset), respectively twice (without quarter offset). The detector acquires $N_V$ summed projection data sets per rotation, each projection data set comprising M measurements (or M active detector cells in a given detector row), each measurement corresponding to the data summed for up to K sources in view of the detector. [A single source system would acquire in one complete revolution $N_V$ projections, where each projection contains M' measurements, with M'≈M/2.] In this configuration, this corresponds to $N_V \times M$ detector-based fan-beam projections, and thus a-priori a total of $N_V \times K \times M$ line integrals. This configuration thus defines a sampling of the tomographic plane a-priori comprising K times more line-integrals; these being acquired in a summed configuration, and associated to only $N_V \times M$ measurements. Thus the associated problem appears significantly underdetermined. However, under condition (C-4) above, each geometric line integral figures K times in a measurement; thus, the number of line-integrals that are involved in the summed measurements is: $N_V \times M$. Accordingly, over a full-rotation of the multi-source CT system of the present invention, the measurement system is not under-determined, and (global) pre-reconstruction inversion is a-priori possible. Under specific conditions described below, much more is possible.

When operating at the maximum effective system speed described above, $\omega_d = K \times \omega_s$, to maintain the total number of projection acquired per effective data acquisition rotation, it is necessary to increase the detector sampling rate in proportion to K. Thus if a third-generation system rotating at $\omega = \omega_s$ samples data with each projection corresponding to a $\Delta t$ projection acquisition time, the dual-drum system operating at maximum speed (for acquisition of a full set of projections, with uniform angular view sampling) will sample the projections in a time intervals equal to $$\delta t = \frac{\Delta t}{K}.$$

Denoting by $\delta t_i$, i=1, ..., K the K consecutive equal (for simplicity of exposition) time intervals that make up a time interval $\Delta t$, we have:

$$|\delta t_i| = \left|\frac{\Delta t}{K}\right|.$$

Figure 27:
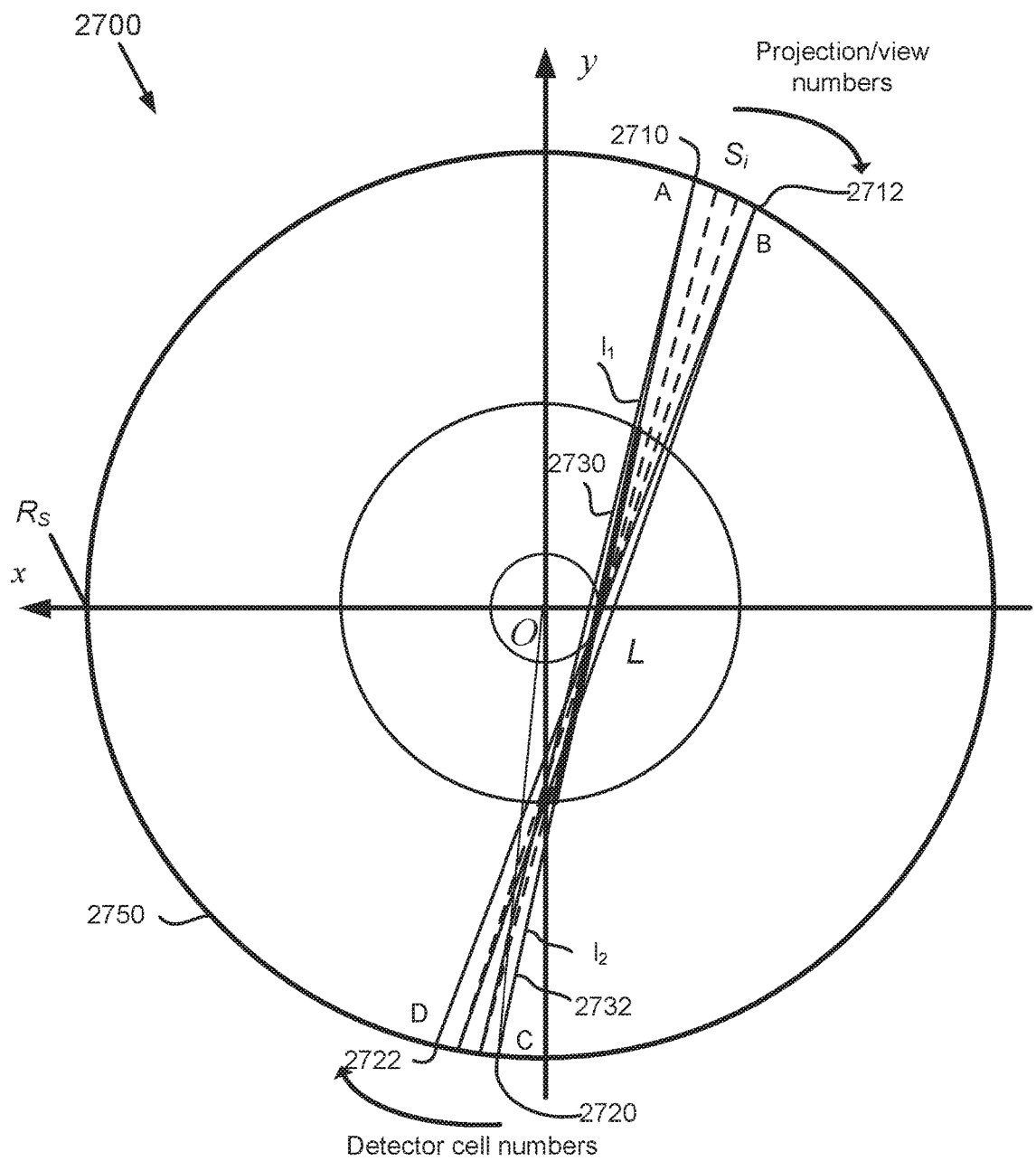
FIG. 27 illustrates the sampling that occurs during a time interval $\Delta t$ corresponding to one source projection acquisition for the source ring for a dual-ring dual-rotation multi-source CT system operating with $\omega_s < \omega_d$.

The associated image plane sampling geometry 2700 is illustrated in FIG. 27 for K=3; where the dimensions are not to scale, and the blurring effect associated with the sampling interval $\Delta t$ has been magnified for the purpose of explanation. During this sampling interval, the source in a conventional CT system, and one of the K sources in the system of the present document travels from point A 2710 to point B 2712. In conventional CT, the associated detector cell corresponding to the sampling of "one line-integral" travels from location C 2720 to location D 2722. In the dual-drum CT system of the present document, the sources can travel at the same angular velocity $\omega_s$. However, during the source travel time corresponding to the arc A to B, the flying detector, which is moving at angular speed $\omega_d = K \times \omega_s$, is sampled K times. Thus the arc CD is swept K times during the interval $\Delta t$ by K successive cells on the detector (each cell sweeping in turn from point C to point D in a time interval $$\delta t_i = \frac{\Delta t}{K}),$$

and the K samples are associated with the same total area $\Omega$ within the object of interest as that swept in a conventional system. This total object area $\Omega$ is delimited by lines $l_1$ 2730 and $l_2$ 2732 in FIG. 27. Further, the total number of photons detected (and associated with individual source in the set of K sources) and represented by the K samples, is the same as that measured in the time interval $\Delta t$ in a conventional system with one source (assuming all other factors constant).

Relabeling the line-integrals for the description, a given source $S_i$ traces during $\Delta t = K \times |\delta t_i|$ paths for K line integrals $L_i^j$; i=1, ... K; j=1, ... K. This set of K lines integral for one of the sources are all associated with, and correspond to the same object area $\Omega$, as the data acquired for one line-integral in a conventional CT system. Thus now considering the K simultaneously active sources, we are led to a system of equations with $K^2$ unknowns:

$$\begin{bmatrix} m_1 \\ \cdot \\ m_K \end{bmatrix} = \begin{bmatrix} I_{01}^1 & \cdot & I_{0K}^1 & & & & & \\ & \cdot & \cdot & \cdot & 0 & & 0 & \\ & \cdot & \cdot & \cdot & & & & \\ & & & & \cdot & \cdot & \cdot & \\ & 0 & & 0 & \cdot & \cdot & \cdot & \\ & & & & I_{01}^K & \cdot & I_{0K}^K \end{bmatrix} \begin{bmatrix} L_1^1 \\ \cdot \\ L_K^1 \\ \cdot \\ L_1^K \\ \cdot \\ L_K^K \end{bmatrix} = [I]_{K,K^2} \begin{bmatrix} L_1^1 \\ \cdot \\ L_K^1 \\ \cdot \\ L_1^K \\ \cdot \\ L_K^K \end{bmatrix} \quad (S1)$$

Figure 28:
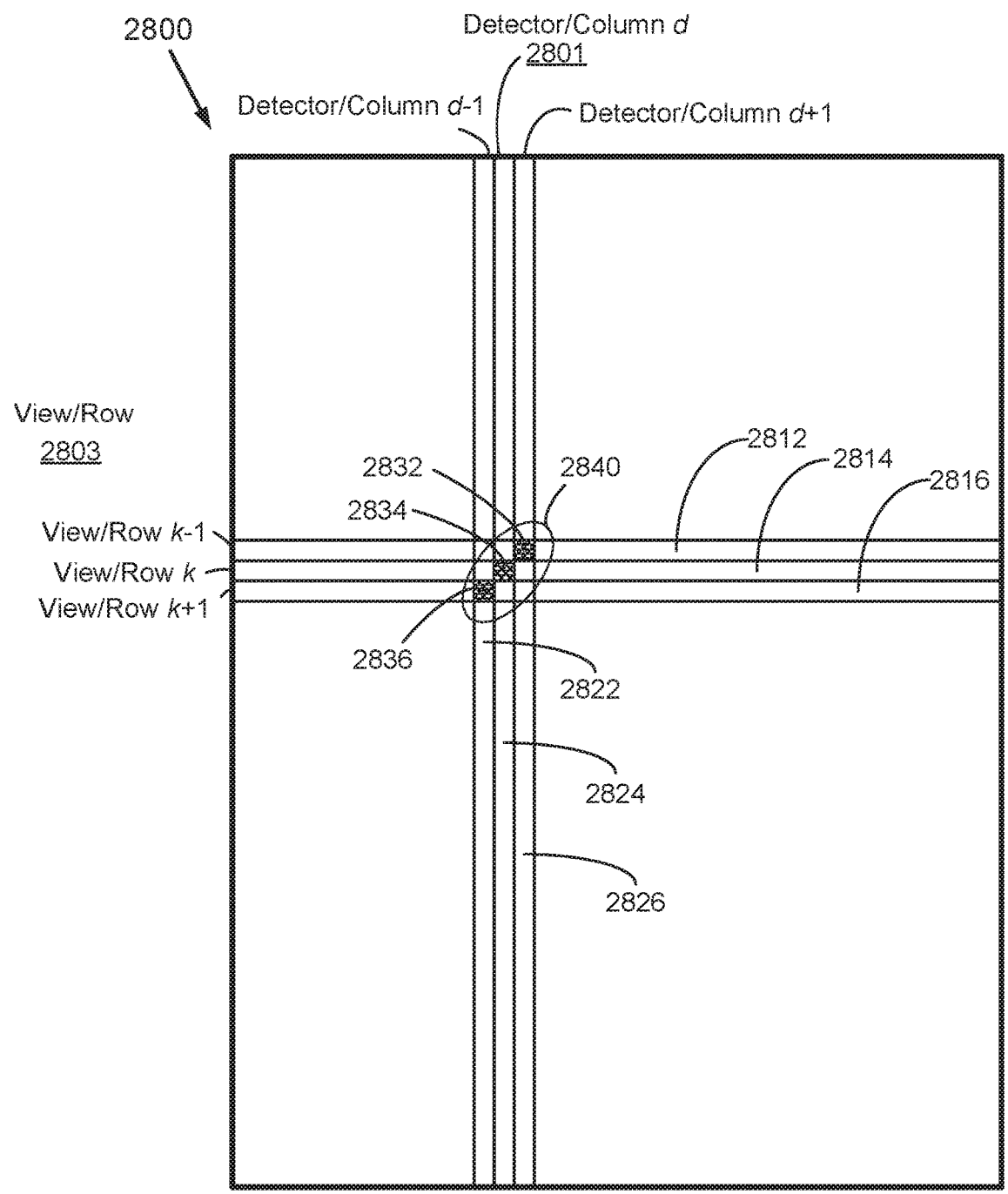
FIG. 28 illustrates an exemplary sinogram space sampling associated with the detector subsampling at time intervals $\delta t$ of the source projection interval $\Delta t$.
Figure 29:
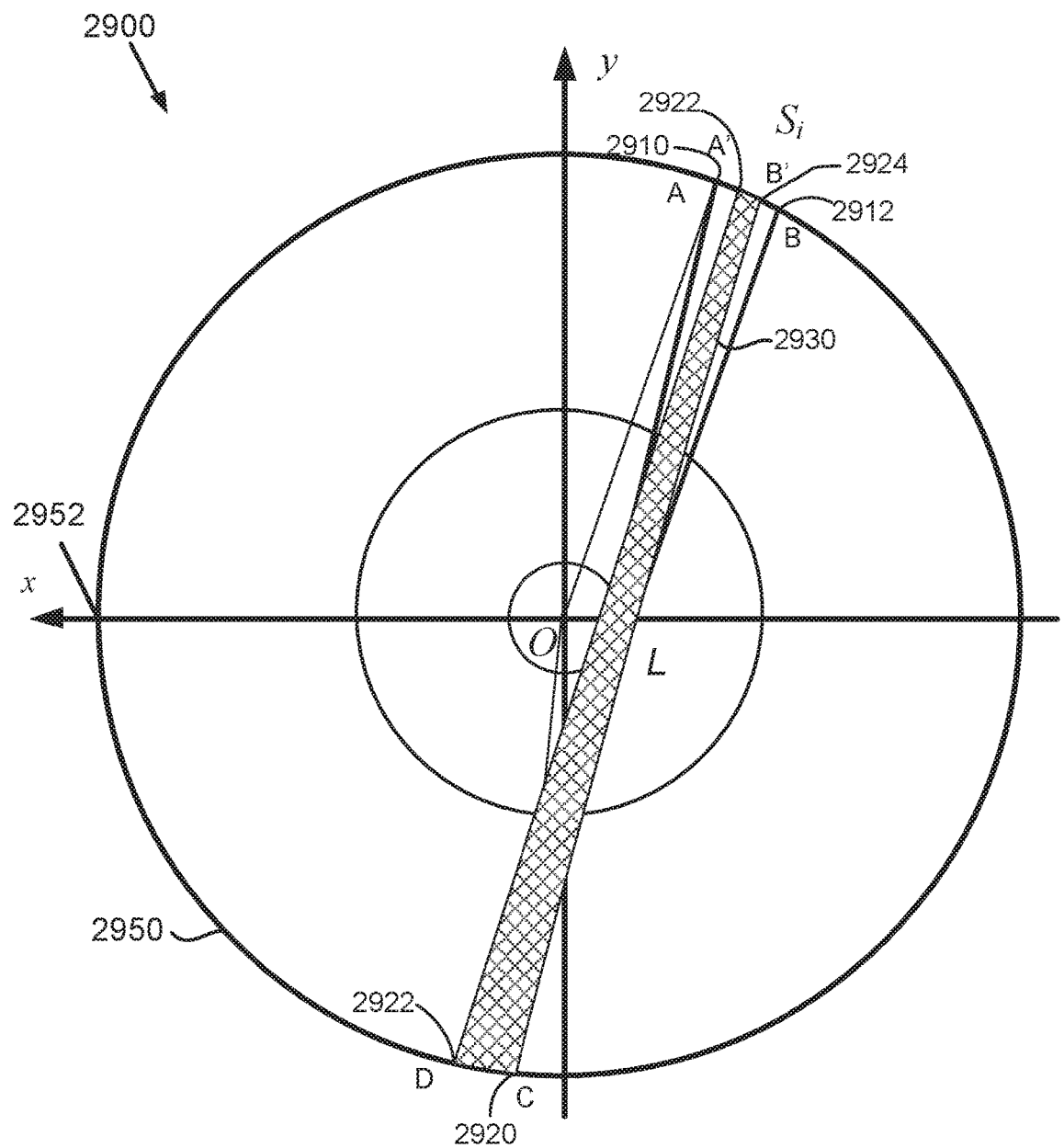
FIG. 29 shows in exemplary form the sampling obtained during a sub-interval $\delta t$ of $\Delta t$ corresponding to a sample time for the detector.

In the system (S1), each of the K measurements $m_i$, i=1, ... K is associated with one of the successive detector cell that sweeps the arc CD in the corresponding time intervals $\delta t_1$. In other words, these measurements are associated to successive rows 2812, 2814, 2816 in the summed projection sinogram and laterally offset columns 2822, 2824, 2826, as indicated schematically, 2800, in FIG. 28 for a system with K=3. Thus the K=3 samples indicated by cross-hatched marks 2832, 2834, and 2836 inside ellipse 2840 are all related to sub-areas of object area $\Omega$. This is shown 2900 in FIG. 29 for the second of the three samples acquired by the flying detector in the case of a system with K=3: the cross-hatched area 2930 corresponds to the central sub-arc A' 2922 to B' 2924 of arc 2610 to 2612 shown in FIG. 29. The corresponding detector cell however travels the full arc range C 2920 to D 2922 during the sub-sampling time interval $|\delta t_2| = \Delta t/3$.

To solve this a-priori underdetermined system of equation locally, we identify $L_i = L_i^1 \sim L_i^j$ for each source $S_i$ i=1, ... K and j=1, ... K. This is an approximation valid in the sense that all line integrals pertain to the same area $\Omega$ (for a given source i). Accordingly, under this approximation the system (S1) may be rewritten as a system of equations in K unknowns:

$$\begin{bmatrix} m_1 \\ \cdot \\ m_K \end{bmatrix} = \begin{bmatrix} I_{01}^1 & \cdot & I_{0K}^1 \\ \cdot & \cdot & \cdot \\ I_{01}^K & \cdot & I_{0K}^K \end{bmatrix} \begin{bmatrix} L_1 \\ \cdot \\ L_K \end{bmatrix} = [I]_{K,K} \begin{bmatrix} L_1 \\ \cdot \\ L_K \end{bmatrix}. \quad (S2)$$

If the sources parameters do not vary in time, then system (S2) is non-invertible or at least severely ill-conditioned, since the rows of the K-by-K $[I]_{K,K}$ matrix are proportional. To locally invert such a system, we introduce, in one embodiment, sources modulations in the following manner: During each of the time intervals $\delta t_i$ we "pinch-off" (via electron beam electrostatic control, for example as provided by control electrodes 626 of FIG. 6) the beam for one of the K sources, source $S_i$, in turn. Assuming for simplicity of description, that all the other source parameters are equal, system (S2) can be written as (with $I_0$ the sources common air output):

$$\begin{bmatrix} m_1 \\ \cdot \\ m_K \end{bmatrix} = I_0 [J_K - I_K] \begin{bmatrix} L_1 \\ \cdot \\ L_K \end{bmatrix}, \quad (S3)$$

where $J_K$ and $I_K$ represent the square matrices of size K-by-K with all entries equal to 1 and the identity matrix with ones on the main diagonal and zeroes elsewhere, respectively. Hence, the following local model matrix is obtained:

$$[J_K - I_K] = \begin{bmatrix} 0 & 1 & ... & 1 \\ \vdots & & \ddots & \vdots \\ 1 & ... & 1 & 0 \end{bmatrix}. \quad (S4)$$

Matrix $[J_K - I_K]$ is known in algebra to be invertible and diagonalizable, with:

$$\det([J_K - I_K]) = (K-1) \times (-1)^{K-1}.$$

Thus as described above X-ray tube gridding [achieved, for example, via electrostatic electron beam pinching—the emitter current remains "on"] and use of specific gridding control timing sequence enable the acquisition of projection data sets from which estimates for the individual line-integrals can be recovered locally from summed measurements, in a dual-drum CT system effectively rotating at K times the angular velocity of a conventional one-source CT system.

Figure 30:
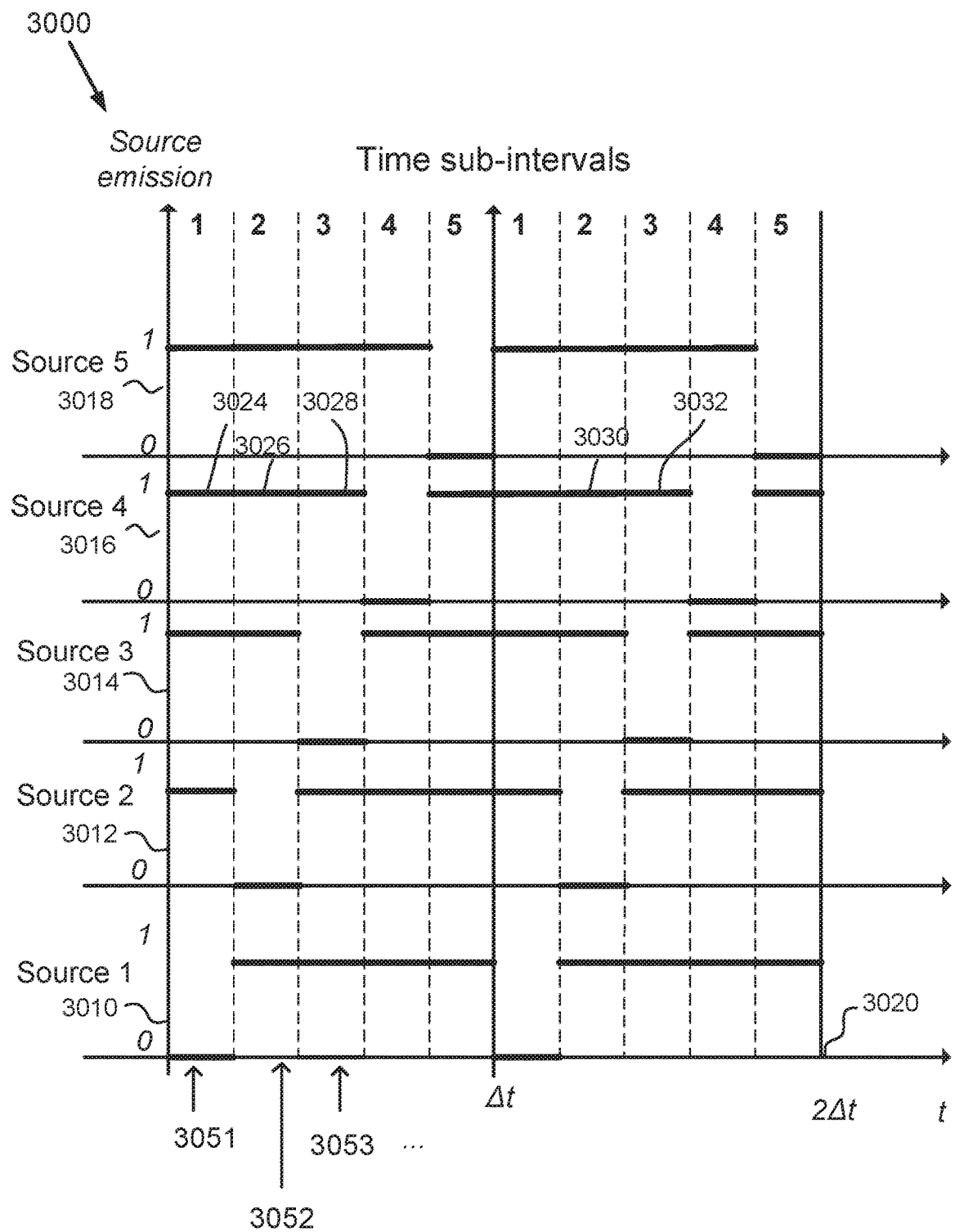
FIG. 30 presents an exemplary source switching time-sequence for the acquisition of multi-source summed data for a dual-rotation multi-source CT system operating with $\omega_s < \omega_d$.

FIG. 30 describes an exemplary embodiment of a sources pinching sequence, 3000. In the figure, a system with up to N=5 simultaneously active (in view of the detector) radiation sources is illustrated. Source time intervals of are illustrated, as well as sub-intervals.

This local recovery of the data is performed as described above in an illustrative embodiment. Many variations on the precise method described are possible, and are understood to be within the scope of the present invention. In particular, many different sources modulation sequences can lead to well behaved matrices for local inversion. Thus, using the source-modulation approach described above, it is possible to locally recover individual line-integral data for $N_i \times M$ geometric lines, which is what a third-generation CT system operating at $\omega_s$ gantry rotation and $\Delta t$ projection sampling time would acquire.

In specific embodiments, CT systems with higher spatial resolution can also be obtained. Indeed, by rotating the detector drum in a dual-drum system at an angular velocity less than the maximum enabling complete data set acquisition, Eq. (21), sub-samplings of the object area associated to sampling by a single-source CT system of the present state-of-the-art are obtained. These sub-sampling in turn provide higher object sampling, leading to higher image spatial resolution.

This sub-sampling can also be combined with distributing the required exposure power in between the sub-set of sources. Reduced tube power enables the use of smaller size tube focal spot, and thus reduce the associated blurring, further leading to higher spatial resolution.

Further increases in spatial resolution can be obtained by offsetting the sources in small increments from their nominal positions, so that shifted samples of the line-integrals are obtained by the various sources, enabling high-resolution imaging as is known in the art. This high sampling density on the source side may be combined with the use of a smaller detector cell pitch, and reduced power at any single source focal spot, thus obtaining smaller size radiation focal spot in support of high spatial resolution. In combination, these techniques enable multi-source CT systems of the present invention to reach spatial resolution un-achievable with single source CT systems.

Figure 31:
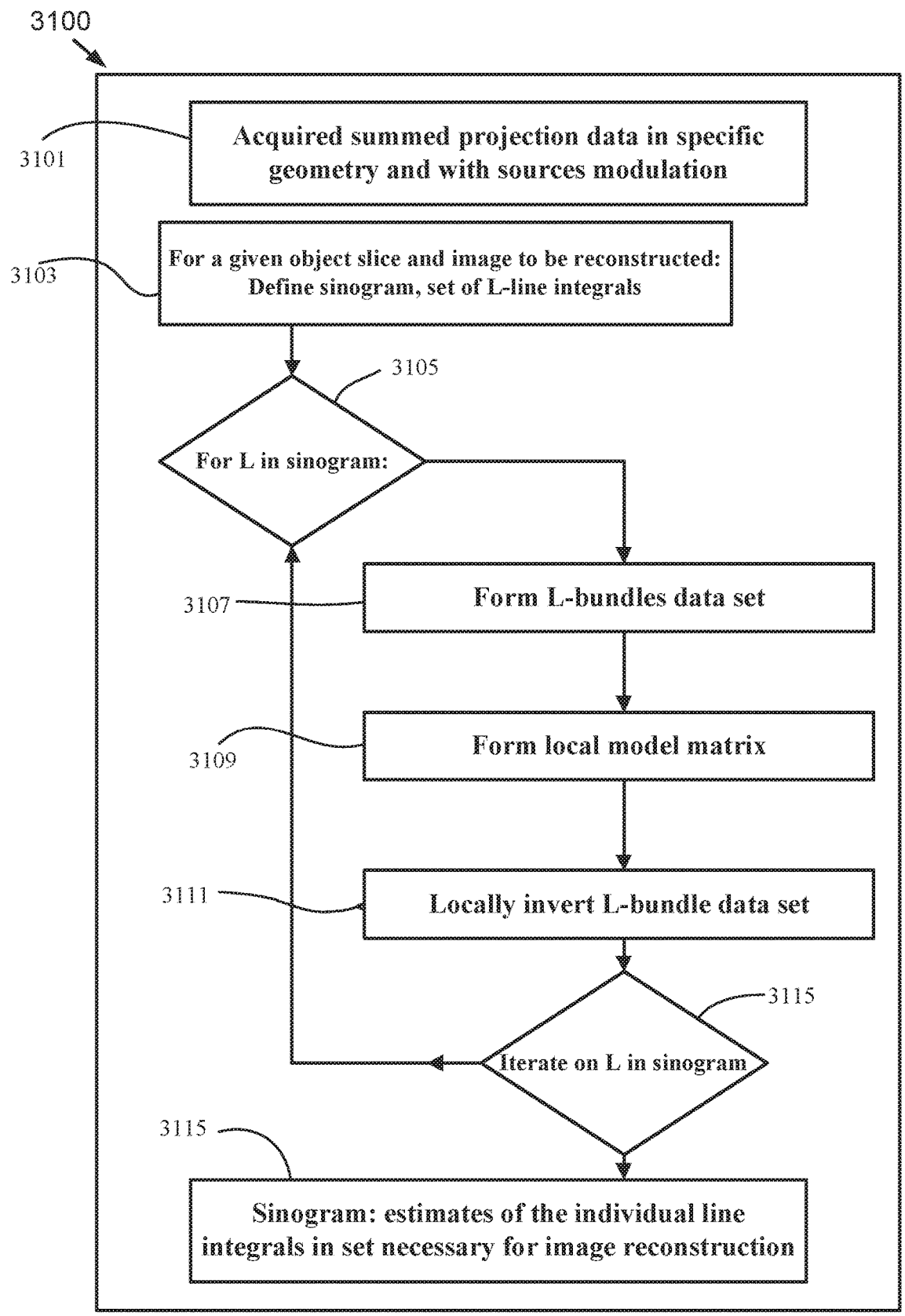
FIG. 31 shows a flow-diagram of a pre-reconstruction inversion algorithm for a multi-source dual-rotation CT system operating with $\omega_s < \omega_d$.

FIG. 31 describes an associated pre-reconstruction inversion algorithm 3100, using sources modulation and/or tube gridding sequence. Summed projection data 3101 are acquired using a specific sources modulation or timing sequence, sufficient for reconstruction of at least one image surface for the object or patient being imaged. For a given tomographic surface, at step 3103 the method defines the set of geometric lines through the object and associated individual line-integral estimates to be obtained, i.e. the sinogram for a given tomographic surface. At step 3105, the method considers a specific geometric line L associated to the sinogram, and for that line L forms the local L-bundle data set at step 3107. The L-bundle is determined from the geometry of the system, the data acquisition parameters, and relates to the object being imaged as a function of the specified object position within the CT system during data acquisition. At step 3109, the local model matrix is formed for the L-bundle of L given knowledge of the sources modulation and/or sources timing sequences. The corresponding data model is then locally inverted at step 3111 using known techniques of linear algebra, such as Gaussian elimination, conjugate gradients, and others as known in the art; regularization techniques, such as Tikhonov regularization, are applied depending on the numerical conditioning of the local model matrix. At step 3115, the method iterates on the lines L associated to the desired sinogram; it is understood that local L-bundle inversion at step 3111 may provide an estimate for the line-integral associated to L, as well as for other geometric lines in the L-bundle of L. When the set of lines L associated to the sinogram in question has been entirely processed, a sinogram 3115, or estimate of the individual line integral projection data to be used for image reconstruction is obtained.

Figure 32:
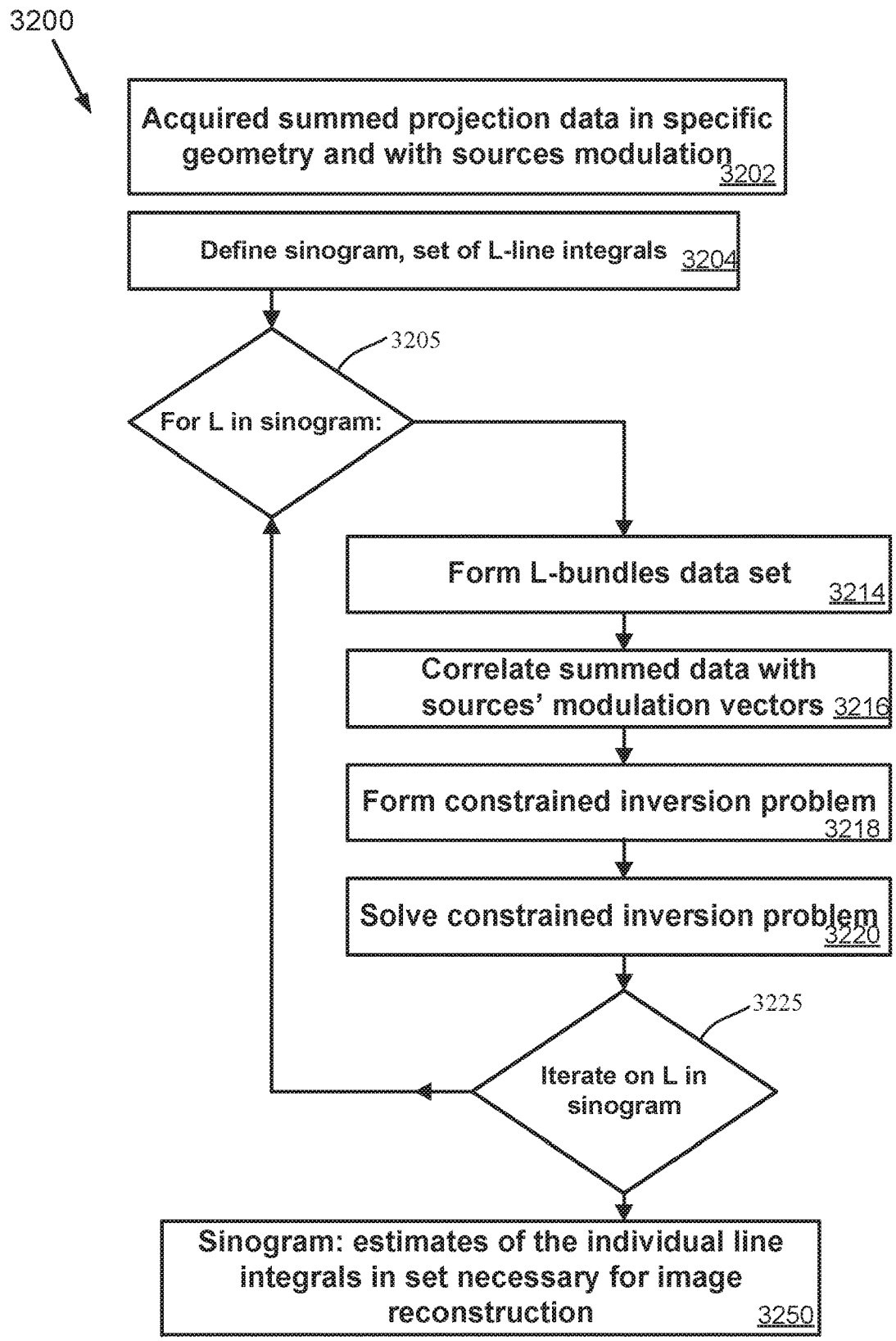
FIG. 32 illustrates a pre-reconstruction inversion algorithm for a multi-source dual-rotation CT system operating with $\omega_s < \omega_d$ formulated as a constrained inversion problem.

In FIG. 32, local pre-reconstruction inversion is assisted by correlation analysis, and otherwise proceeds as in FIG. 31. FIG. 32 describes a pre-reconstruction inversion algorithm 3200, using sources modulation and/or tube gridding sequence. Summed projection data 3202 are acquired using a specific sources modulation or timing sequence, sufficient for reconstruction of at least one image surface for the object or patient being imaged. For a given tomographic surface, at step 3204 the method defines the set of geometric lines through the object and associated individual line-integral estimates to be obtained, i.e. the sinogram for a given tomographic surface. At step 3205, the method considers a specific geometric line L associated to the sinogram, and for that line L forms the local L-bundle data set at step 3214. The L-bundle is determined from the geometry of the system, the data acquisition parameters, and relates to the object being imaged as a function of the specified object position within the CT system during data acquisition. At step 3216, local correlation analysis is performed between the source modulation vectors and the local projection data, as further described in patent application Ser. No. 15/047,412. This correlation analysis allows the formulation of a constrained inversion problem at step 3218, the inversion of which at step 3220 provides an estimate for the line-integral associated with geometric line L. The constrained inversion problem may also rely on the use of a local model matrix. The constrained inversion problem is solved using known methods such as conjugate gradients, and others as known in the art; regularization techniques, such as Tikhonov regularization, are applied depending on the numerical conditioning of the local model matrix. At step 3225, the method iterates on the lines L associated to the desired sinogram; it is understood that local L-bundle constrained inversion at step 3220 may provide an estimate for the line-integral associated to L, as well as for other geometric lines in the L-bundle of L. When the set of lines L associated to the sinogram in question has been entirely processed, a sinogram 3250, or estimate of the individual line integral projection data to be used for image reconstruction is obtained.

Figure 33:
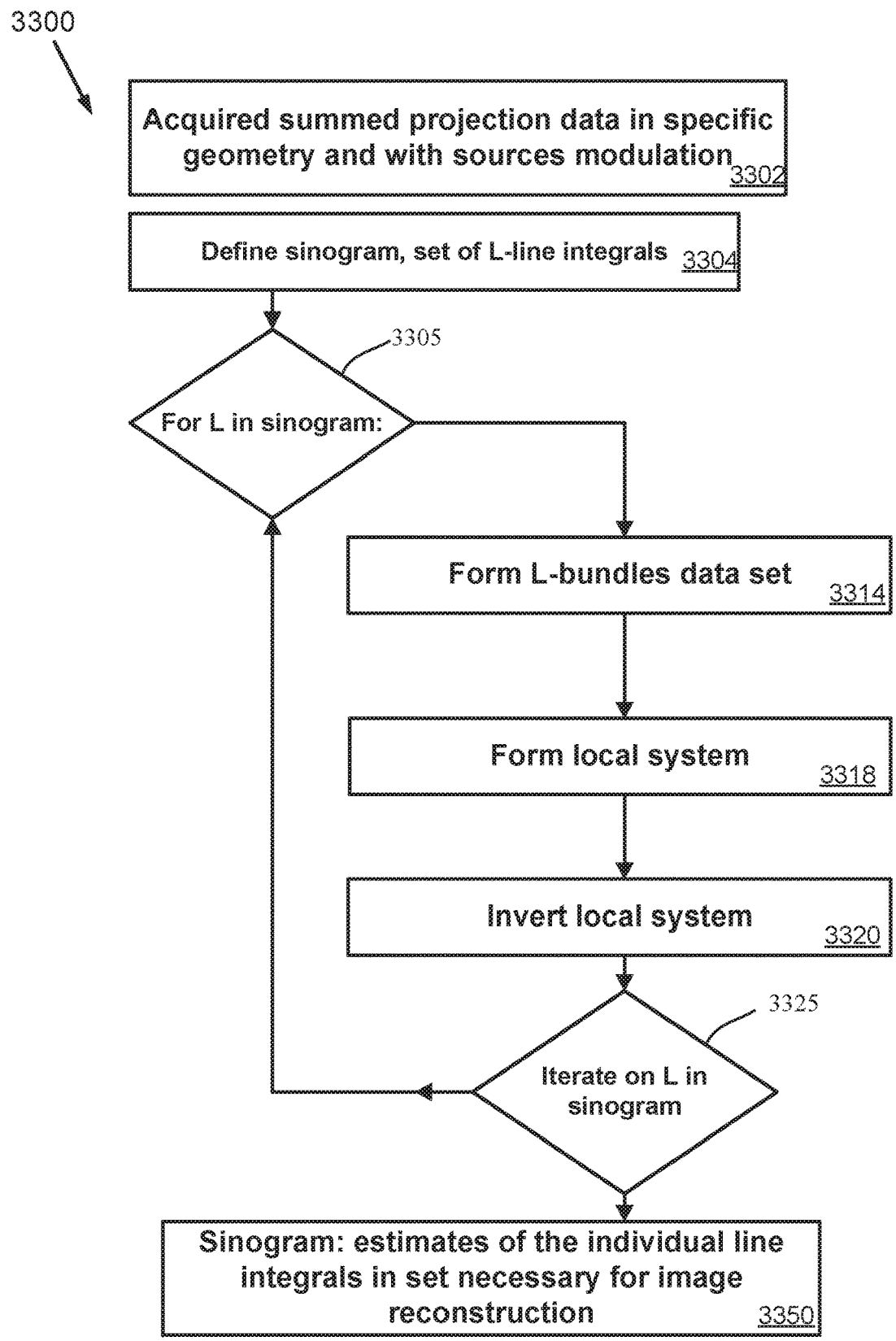
FIG. 33 presents a pre-reconstruction inversion algorithm for a multi-source CT system operating with $\omega_s = \omega_d$.

In FIG. 33, the particular embodiment with $\omega_d = \omega_s$, is considered from the point of view of the pre-reconstruction inversion algorithm. It is understood that the considerations below also apply to a more conventional multi-source CT system with a single rotating gantry, a detector arc extending substantially over a central angle $\pi + 2\Gamma$ radians and a set of $N_a \geq 2$ sources distributed over a central angle $\theta_a$, the complementary central angle $\pi - 2\Gamma$ radians being such that $\theta_a \leq \pi - 2\Gamma$, as FIG. 25 can also represent. Under the condition $\omega_d = \omega_s$, as well as under other favorable conditions, such as when the system is not made to operate at its maximum effective rotation speed, the pre-reconstruction inversion problem can be solved in a straightforward manner, as illustrated in FIG. 33. In FIG. 33, local pre-reconstruction inversion is performed without correlation analysis, and otherwise proceeds as in FIG. 31. FIG. 33 describes a pre-reconstruction inversion algorithm 3300, using sources modulation and/or tube gridding sequence or not. Summed projection data 3302 are acquired using a specific sources modulation or timing sequence, sufficient for reconstruction of at least one image surface for the object or patient being imaged. For a given tomographic surface, at step 3304 the method defines the set of geometric lines through the object and associated individual line-integral estimates to be obtained, i.e. the sinogram for a given tomographic surface. At step 3305, the method considers a specific geometric line L associated to the sinogram, and for that line L forms the local L-bundle data set at step 3314. The L-bundle is determined from the geometry of the system, the data acquisition parameters, and relates to the object being imaged as a function of the specified object position within the CT system during data acquisition. The data relating line L and the other lines in the L-bundle figuring in a given measurement associated with the bundle are expressed as a set of equations; and the local system of equation is inverted at step 3320 provides an estimate for the line-integral associated with geometric line L. The constrained inversion problem may also rely on the use of a local model matrix. The constrained inversion problem is solved using known methods such as conjugate gradients, and others as known in the art; regularization techniques, such as Tikhonov regularization, are applied depending on the numerical conditioning of the local model matrix. At step 3325, the method iterates on the lines L associated to the desired sinogram; it is understood that local L-bundle constrained inversion at step 3320 may provide an estimate for the line-integral associated to L, as well as for other geometric lines in the L-bundle of L. When the set of lines L associated to the sinogram in question has been entirely processed, a sinogram 3350, or estimate of the individual line integral projection data to be used for image reconstruction is obtained.

The formulation 3318 of the local problem to be inverted at step 3320 is now discussed in some more details. Now with reference to FIG. 24 and FIG. 25, consider a system with $N_S \geq 2$ equidistributed sources over an angle $\theta_a$ (for example, $\theta_a \leq \pi - 2\Gamma$), forming a (minimum) angle $\Delta\theta_s$ between any two adjacent sources, with, for illustration:

$$\Delta\theta_s = \frac{\theta_a}{N_s - 1}.$$

For a given line-integral L through the measurement field-of-view (MFOV) of radius $R_M$, the L-bundle is defined as follows. The L-bundle associated to line L 2553 is the set of geometric lines with vertex at a fixed point d at a distance $R_d$ from isocenter (nominally on the surface of the detector array at a given instant in time; thus the vertex may be on different points on the detector surface as a function of time) and originating at a set of source positions $S_i$, 2501, 2502, 2503, . . . 2514. Since we are only interested in lines that intersect the MFOV, the central angle sustained by the arc such that any point $S_i$ is within the arc is thus:

$$\Delta\theta_a = 2 \ asin\left(\frac{R_M}{R_d R_s} \times \left[R_s \cos(\Gamma) + \sqrt{R_d^2 - R_M^2}\right]\right),$$

or within $\min\{\Delta\theta_a, \theta_a\}$.

Thus the set of lines in the L-bundle is obtained by starting from point 2503, obtained as the intersection of line L 2553 with the source trajectory 2520 (thus at the opposite end of the MFOV 2530 with respect to d 2540), and offsetting by multiples of the central angle $\Delta\theta_s$ between two sources; the offsetting being performed on both sides (that is, clockwise and counterclockwise). Each point that is offset from 2553 by a central angle $\Delta\theta_s$ and within the arc $\Delta\theta_a$ as seen from d is a valid point, leading to a geometric line in the L-bundle from the corresponding offset point on the source trajectory to point d. Denoting by l the cardinal of the L-bundle set of geometric lines:

$$l = \text{card}(L\text{-bundle}),$$

it is apparent that:

$$l \leq 1 + \frac{\Delta\theta_a}{\Delta\theta_s}.$$

The number of measurements $N_m(L)$ involving at least one of the lines in the L-bundle is then given as a function of l and the number of sources $N_s$:

$$N_m(L) = l + N_s - 1 > l.$$

Further, any summed measurement involving one of the lines in the L-bundle, involves only other lines in the L-bundle (and possible paths in air outside the MFOV). Accordingly, the system acquires $N_m(L)$ measurements in $l \leq N_m(L)$ unknowns, and is locally solvable (in the least-squares sense if not directly invertible). Thus, for such a system the pre-reconstruction inverse problem is locally solvable, for any $N_s \geq 2$ equidistributed sources. It is noted that if additional paths in air are acquired due to the sources not being collimated, or not being collimated to specifically restrict illumination from each source to the measurement FOV of radius $R_M$, then these additional paths can be accounted for through a calibration process. As they do not contain object information, the local problem formulation applies as above, albeit with the possibility of a larger L-bundle set for each geometric line L. Thus, local inversion at step 3320 of FIG. 33 can proceed by solving a system of equations in l unknowns and $N_m(L)$ measurements.

Now the case $\omega_s > \omega_d$ is considered in more details. Since more instantaneous power can be extracted from a target of a specific material by increasing the sweep velocity of an electron beam with respect to the target, it may be desirable to use a large emitter ring velocity $\omega_s$. Considering a dual-drum CT system with $\omega_s > \omega_d$, as enabled for example by a system with a magnetic bearing for a ring of source emitters facing a common target (whether the target is fixed or not). Under these conditions, and with reference to FIG. 34, the question is no longer one of sampling for a given line integral L 2270 (since any such line L is sampled at least once as soon as $\omega_s = \omega_d$), but rather one of flux and thus signal-to-noise ratio in the measured data. Thus, we consider a reference system, a third generation single-source system rotating at an angular velocity $$\omega_0 = \frac{2\pi}{T_0}$$

where $T_0$ is the reference system rotation time/period. The dual-ring multi-source CT system of the present invention acquires projection data at an effective rotation speed equal to $$\omega_d = \frac{2\pi}{T_d},$$

where $T_d$ is the detector drum [flying detector] rotation time/period. The dual-drum system has an extended aperture with a central angle of $\theta_a$ radians. Therefore, the intersection of an arbitrary line L with the source trajectory is swept by the extended aperture during a period $$T_d^a = T_d \frac{\theta_a}{2\pi} = \frac{\theta_a}{\omega_d}.$$

The system architecture of the present document enables an increase in effective data acquisition with respect to the reference system by a factor p, while maintaining the flux/dose per individual projection, as is now discussed. To simplify the analysis below, it is assumed that the source output for the dual-ring system, per source, is equal to that of the source output of the reference system. Under other conditions, the relationships below can be scaled by an appropriate factor.

Accordingly, with $\omega_d = p\omega_p$, this implies:

$$T_d = \frac{T_0}{p}.$$

To keep source blurring equal to that of the reference system, the relationship between the sample times must be:

$$\delta t_d = \delta t = \frac{\Delta t}{p} \times \frac{\omega_d}{\omega_s},$$

or a fraction:

$$\frac{\delta t}{\Delta t} = \frac{\omega_0}{\omega_d} \times \frac{\omega_d}{\omega_s} = \frac{\omega_0}{\omega_s} = \frac{1}{p} \times \frac{\omega_d}{\omega_s}. \quad (S21)$$

of the reference sample time.

To retain the signal-to-noise ratio at the level of the reference system, it is thus required to sample a given line several times, to make up for the loss in integration time expressed by (S21). The number of sources that sweep by the end of a given line L in time interval $T_d^a$ is $K_s$, given as a function of K the number of sources simultaneously in view of the detector by:

$$K_S = N_S \frac{\theta_a}{2\pi} \frac{\omega_s}{\omega_d} = K \frac{\omega_s}{\omega_d}.$$

Thus to keep the projection signal-to-noise ratio constant with respect to the reference system, it is required that:

$$K_S \frac{\delta t}{\Delta t} \geq 1.$$

This in turn requires:

$$N_S \frac{\theta_a}{2\pi} \frac{\omega_s}{\omega_d} \frac{1}{p} \times \frac{\omega_d}{\omega_s} \geq 1, \text{ or } K \frac{1}{p} \geq 1;$$

Or:

$$N_S \frac{\theta_a}{2\pi} \frac{1}{p} \geq 1,$$

independent of $\omega_s$.

If each source on the dual-drum system has an output scaled by a fraction f versus the reference single-source system, the equation above becomes:

$$K \frac{f}{p} \geq 1$$

Thus in general a higher rotation speed for the source gantry does not lead to a new constraint, but rather expresses (as was already found for the case $\omega_s < \omega_d$) that the speed increases (p) are directly related to the number of sources K in view of the detector through the extended aperture of central angle equal to $\theta_a$ radians. This is because the shorter detector integration time associated by the higher source drum rotation velocity is compensated by the larger number of sources that pass through the end of a line through the object.

Figure 34:
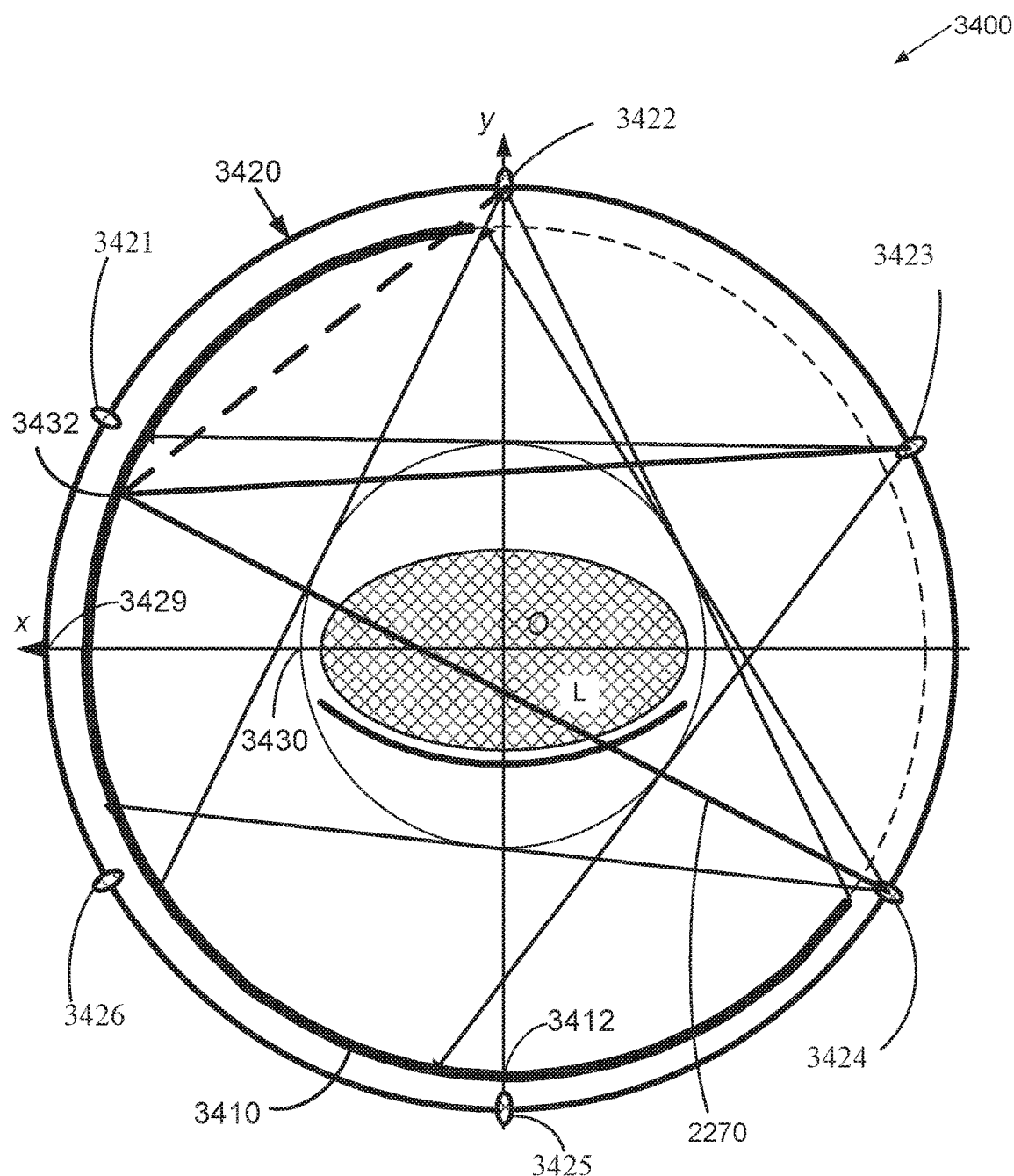
FIG. 34 illustrates the sampling that occurs in a multi-source dual-rotation CT system of the present invention operating with $\omega_s > \omega_d$.
Figure 35:
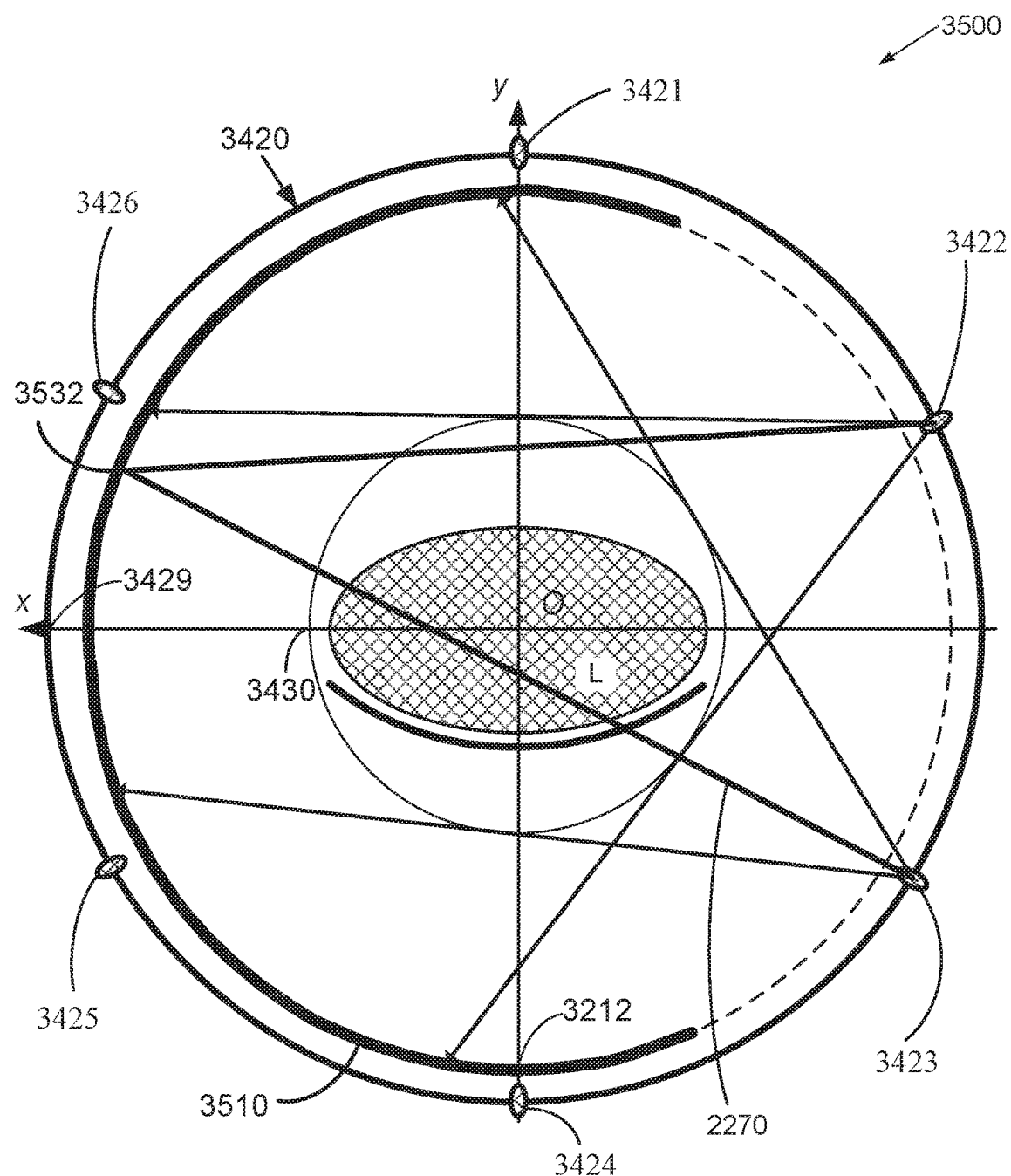
FIG. 35 further illustrates the sampling that occurs in a multi-source dual-rotation CT system of the present invention operating with $\omega_s > \omega_d$.

The associated sampling condition for the case $\omega_s > \omega_d$ is illustrated in FIG. 34 and FIG. 35. FIG. 34 describes a multi-source CT system of the present invention with six sources 3421, . . . 3426. At the instant depicted in the figure, sources 3424, 3423 and 3422 are active. Since $\omega_s > \omega_d$, 3422 has just been turned on active or pinched mode, while source 3424 is about to be turned off from active or pinched mode. In general, for the system of the figure, at least two sources are simultaneously in view of the detector. Source 3424 is sampling line 2270 with a summed measurement acquired at detector cell 3432.

A few instants later, the system gantries/drums have rotated such that it is now source 3423 that is sampling line 2270, with a summed measurement acquired at cell 3532 (different from cell 3432). Under the angular velocities condition $\omega_s > \omega_d$, a number of sources larger than $$N_S \frac{\theta_a}{2\pi}$$

will sample line 2270 and give rise to summed measurements at a plurality of detector cells on radiation detector 3510.

Figure 36:
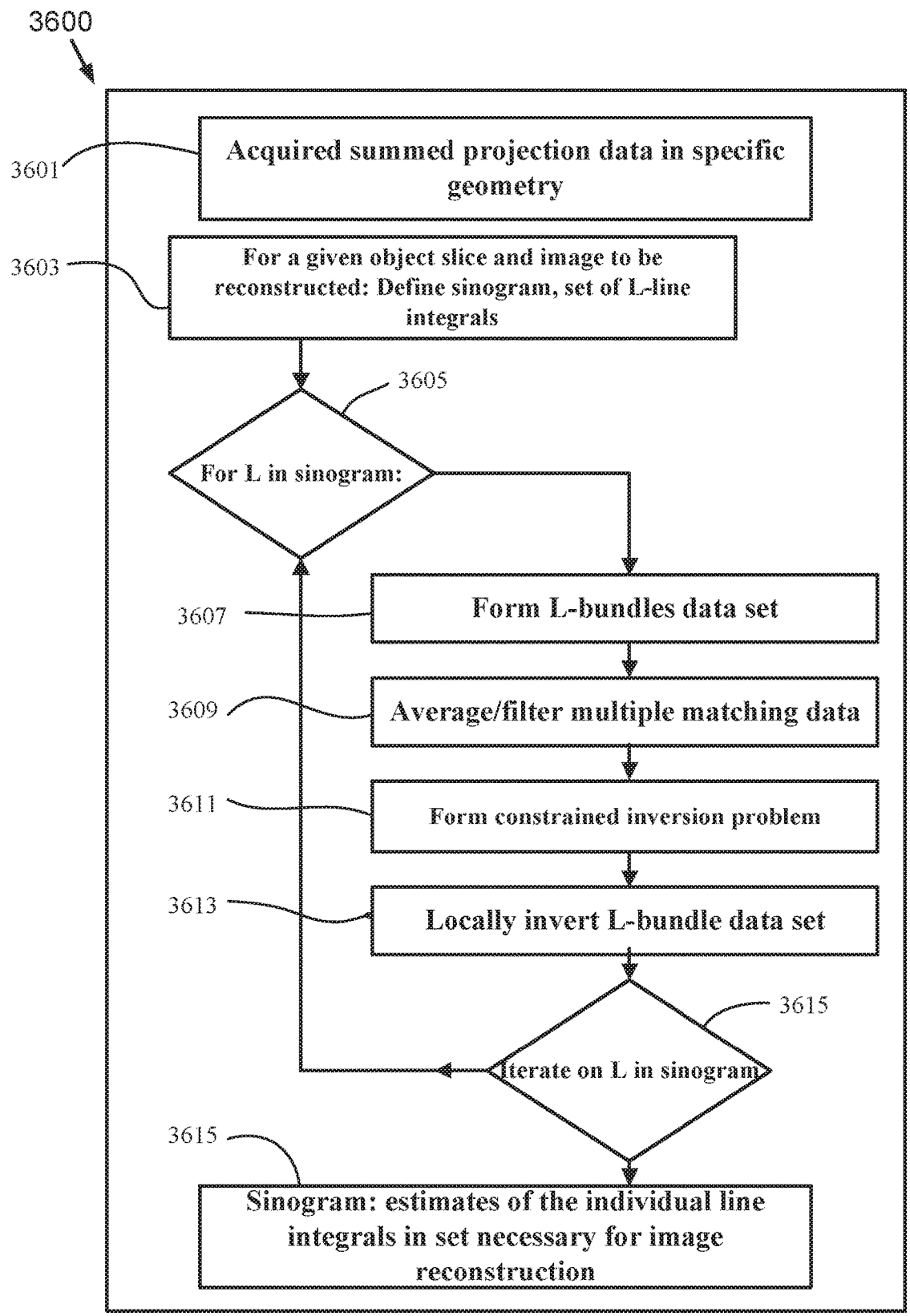
FIG. 36 presents the flow-chart for a pre-inversion algorithm for a multi-source dual-rotation CT system of the present invention operating with $\omega_s > \omega_d$.

In FIG. 36, the particular embodiment with $\omega_s > \omega_d$, is considered from the point of view of the pre-reconstruction inversion algorithm. In FIG. 36, local pre-reconstruction inversion is performed with or without correlation analysis, and otherwise proceeds as in FIG. 31. FIG. 36 describes a pre-reconstruction inversion algorithm 3600, optionally using sources modulation and/or tube gridding sequence. Summed projection data 3601 are acquired using a specific sources modulation or timing sequence, sufficient for reconstruction of at least one image surface for the object or patient being imaged. For a given tomographic surface, at step 3603 the method defines the set of geometric lines through the object and associated individual line-integral estimates to be obtained, i.e. the sinogram for a given tomographic surface. At step 3605, the method considers a specific geometric line L associated to the sinogram, and for that line L forms the local L-bundle data set at step 3607. The L-bundle is determined from the geometry of the system, the data acquisition parameters, and relates to the object being imaged as a function of the specified object position within the CT system during data acquisition. The data relating line L and the other lines in the L-bundle figuring in a given measurement associated with the bundle are expressed as a set of equations; the set of equations accounts for the multiple additional samplings of line L over the L-bundle available as a result of $\omega_s > \omega_d$, at step 3609: straight data averaging, or in specific implementation data filtering, leads to the expression of a local system with a reduced number of rows (as compared to the number of available relevant measurements, as a result of averaging/processing). Additionally, and optionally, the problem may be formulated as a constrained inversion problem at step 3611. The local system of equation is inverted at step 3613 provides an estimate for the line-integral associated with geometric line L. The constrained inversion problem may also rely on the use of a local model matrix. The constrained inversion problem is solved using known methods such as conjugate gradients, and others as known in the art; regularization techniques, such as Tikhonov regularization, are applied depending on the numerical conditioning of the local model matrix. At step 3615, the method iterates on the lines L associated to the desired sinogram; it is understood that local L-bundle constrained inversion at step 3320 may provide an estimate for the individual projection estimate for line L as well as other lines in the L-bundle of L. When all geometric lines associated with the desired output sinogram have been processed, the estimation process for the sinogram 3615 that forms the input to tomographic image reconstruction is complete.

Figure 37:
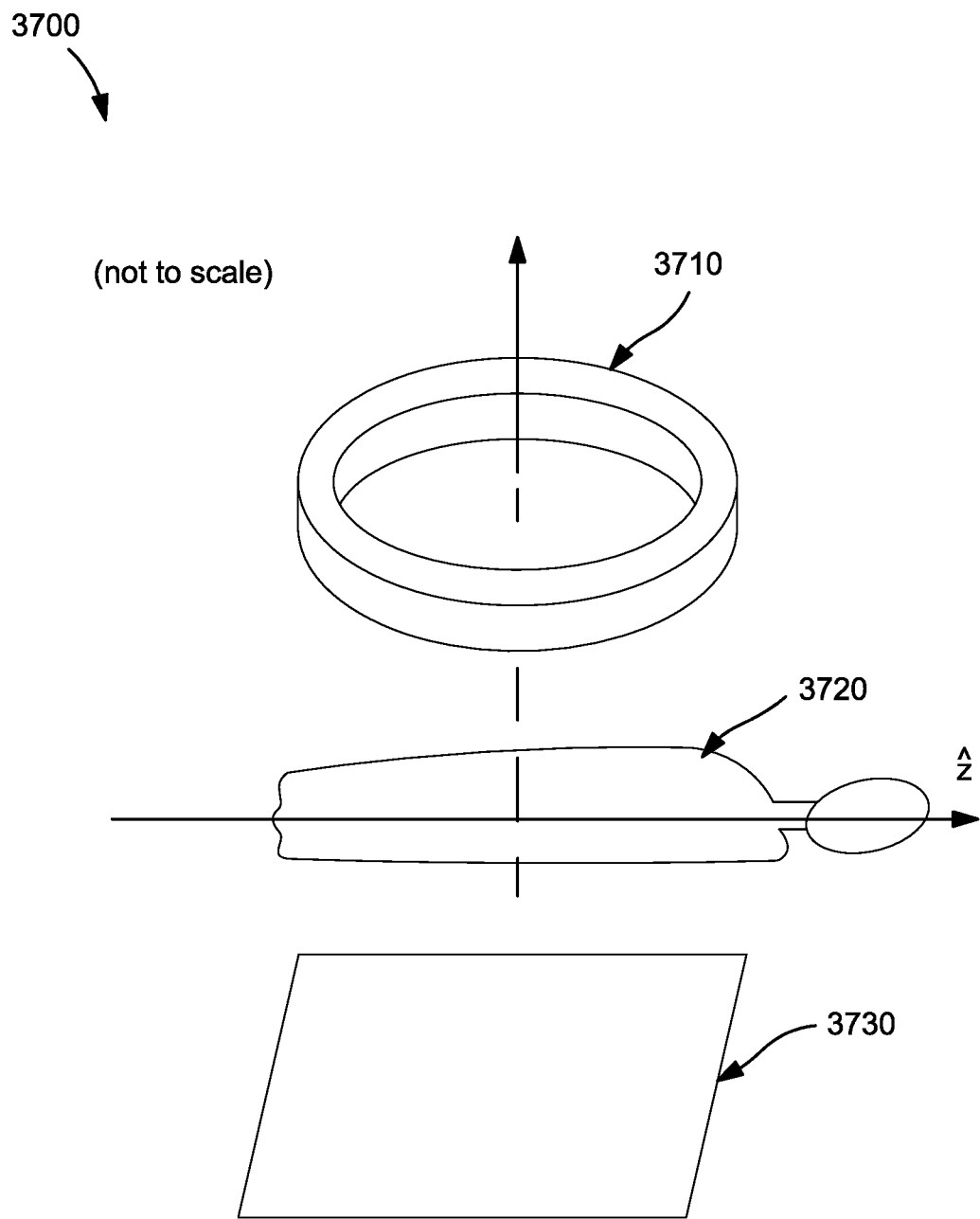
FIG. 37 shows the design of a tomosynthesis X-ray system per the present invention, with the dual-ring X-ray source system located on a side of the body or object to be imaged.

FIG. 37 shows the design of a tomosynthesis X-ray system per the present invention, with the dual-ring X-ray source system located on a side of the body or object to be imaged, as appropriate for tomosynthesis imaging or limited-angle CT imaging. In such an embodiment, the vacuum envelope ring can be made smaller, since the bore does not need to be large enough to accommodate the body/object being imaged. The emitters and target are arranged differently for this application, with the emitters' electron beam traveling radially toward the target, and the anode target forming an angle of about 7-20 degrees with respect to a plane containing the z-axis and orthogonal the direction of electron beam travel (for any given emitter) (not shown). Alternatively, for such an application, a bore in the vacuum envelope is not needed. In such an embodiment, a heat and current conducting disk can be provided within the vacuum envelope, thus facilitating exchanges to the environment; for example, with the provision of disk contact areas at or near the system isocenter.

It is noted that the results obtained in this document do not depend specifically on having the $N_S$ sources equidistributed in central angle. Indeed, embodiments where the sources are distributed in angle and populate a subset of a grid of points with central angle $\Delta\theta_s$ are explicitly contemplated. Central angle $\Delta\theta_s$ is then understood to constitute a "minimum central angle." Thus the sources may also be distributed in groups, with sources in the group separated by $\Delta\theta_s$ or a multiple thereof, and the source groups or arrays separated by a multiple of $\Delta\theta_s$. Further, sources may be distributed in groups with various minimal angles $\Delta\theta_{s_i}$ for i varying over an index set. The corresponding plane sampling will then contain an increased number of geometric lines, and the local bundles can then be distributed in groups of bundles.

The advantages of the above described apparatus embodiments, improvements, and methods should be readily apparent to one skilled in the art, as to enabling the design of computed tomography systems acquiring full sets of projection data and optimized for speed of data acquisition. Additional design considerations may be incorporated without departing from the spirit and scope of the invention. It should thus be noted that the matter contained in the above description and/or shown in the accompanying drawings should be interpreted as illustrative and not in a limiting sense. Accordingly, the following claims are intended to cover all generic and specific features described herein, as well as all statements of the scope of the present methods, and systems which, as a matter of language, might be said to fall therebetween.

What is claimed is:

1. A multiple-source computed tomography system comprising:
    an annular vacuum chamber disposed around a passage;
    a supporting system configured to support within the passage an item selected from the group consisting of an object and a living organism to be imaged;
    a target ring disposed within the chamber, the passage passing through an axial opening of the target ring;
    a plurality of electron beam emitters mounted to a mechanically rotatable emitter gantry within the vacuum chamber, each electron beam emitter configured to emit an electron beam towards the target ring and to cause emissions of x-rays at an impact location of the electron beam on the target ring;
    an x-ray radiation detector array disposed within the passage and mounted upon a rotatable detector gantry, the rotatable detector gantry configured to rotate during imaging at a different angular velocity than rotation of the rotatable emitter gantry;
    an image processing system configured to receive projection data from the radiation detector array, and to generate tomographic images from the projection data received from the radiation detector array.

2. The multiple-source computed tomography system of claim 1, wherein the target ring is configured to be rotatable separately from the emitter gantry about the passage.

3. The multiple-source computed tomography system of claim 1, wherein the emitter gantry is supported by a magnetic bearing.

4. The multiple-source computed tomography system of claim 1, wherein:
    the projection data received by the image processing system comprises total received radiation at a plurality of radiation detector elements, wherein a plurality of the plurality of radiation detector elements each receives radiation from a plurality of the impact locations of electron beams on the target ring emitted by a plurality of simultaneously active electron emitters of the plurality of electron emitters;
    the image processing system is configured to process the projection data to form a sinogram; and
    the image processing system is configured to process the sinogram to produce a tomographic image of radiation attenuation within the item.

5. The multiple-source computed tomography system of claim 4, wherein the image processing system is configured to process the projection data from the radiation detector to form a sinogram by executing inversion firmware that: forms equations for L-bundles for each geometric line in the sinogram; and solves the equations to determine individual line projection values.

6. The multiple-source computed tomography system of claim 1, wherein the system is configured to rotate the emitter gantry ring while keeping the target stationary while the image processing system receives projection data.

7. The multiple-source computed tomography system of claim 6, wherein the emitter gantry is supported by a magnetic bearing.

8. The multiple-source computed tomography system of claim 6, wherein:
    the projection data received by the image processing system comprises total received radiation at a plurality of radiation detector elements, wherein a plurality of the plurality of radiation detector elements each receives radiation from a plurality of the impact locations of electron beams on the target ring emitted by a plurality of the plurality of activated electron emitters;
    the image processing system is configured to process the projection data to form a sinogram; and
    the image processing system is configured to process the sinogram to produce a tomographic image of radiation attenuation within the item.

9. The multiple-source computed tomography system of claim 8, wherein the image processing system is configured to process the projection data from the radiation detector to form a sinogram by executing inversion firmware that: forms equations for L-bundles for each geometric line in the sinogram; and solves the equations to determine individual line projection values.

10. The multiple-source computed tomography system of claim 1, wherein the detector has at least one aperture, the aperture configured to permit transmission of x-ray radiation through the passages.

11. The multiple-source computed tomography system of claim 1 wherein the rotatable detector gantry is configured to rotate at an angular velocity K times an angular velocity of rotation of the emitter gantry, where K is an integer greater than one and K is a number of emitters on the emitter gantry in view of the radiation detector array at any one time during rotation of the gantries.

12. A multiple-source computed tomography system comprising:

an annular vacuum chamber disposed around a passage;
a supporting system configured to support within the passage an item selected from the group consisting of an object and a living organism;
an annular rotatable emitter structure disposed within the chamber, the passage passing through an opening in the emitter structure;
a plurality of electron beam emitters attached to the emitter structure, each electron beam emitter configured to emit an electron beam towards at least one target and to cause emissions of x-rays from a point of impact of the electron beam on the at least one target;
an x-ray radiation detector array disposed within the passage and mounted upon a rotatable detector gantry, the annular rotatable emitter structure configured to rotate at a faster angular velocity than the rotatable detector gantry;
an image processing system configured to receive data from the radiation detector array, and to generate tomographic images of the item from the data from the radiation detector array.

13. The multiple-source computed tomography system of claim 12, wherein the system is configured with the at least one target on a rotatable target ring, the passage passing through an opening of the target ring, and to rotate the target ring while the image processing system receives the data from the radiation detector array.

14. The multiple-source computed tomography system of claim 12, wherein the system is configured with the at least one target on a fixed target ring, the passage passing through an opening of the target ring, the rotatable emitter structure configured to rotate while the image processing system receives the data from the radiation detector array.

15. The multiple-source computed tomography system of claim 14, wherein the rotatable emitter structure is supported by a magnetic bearing.

16. The multiple-source computed tomography system of claim 14, wherein the emitter gantry is supported by a magnetic bearing.

17. The multiple-source computed tomography system of claim 12, wherein the system is configured with the at least one target mounted to a rotatable target ring, and wherein the emitter structure and the target ring are configured to rotate in opposite directions while the image processing system receives the data from the radiation detector array.

18. A method of imaging comprising:
rotating an electron-beam emitter ring bearing a plurality of electron beam emitters about a passage at a first angular velocity, the emitter ring rotating with respect to a target ring, the electron-beam emitter ring comprising a plurality of electron emitters, the electron-beam emitter ring disposed within a stationary annular vacuum chamber having a passage and the electron-beam emitter ring rotates about the passage;
wherein the target ring is positioned to receive electron beams from active electron emitters of the electron-beam emitter ring and adapted to emit x-ray radiation where struck by the electron beams;
rotating a radiation detector array at a second angular velocity about the passage, the detector array having an aperture for passing x-ray radiation;
activating a plurality of the plurality of electron-beam emitters;
acquiring projection data from the radiation detector, projection image data comprising total received radiation at a plurality of radiation detector elements of the radiation detector array, wherein a plurality of the plurality of radiation detector elements receive x-ray radiation emitted at intersections with the target ring of the electron beams from a plurality of the plurality of activated electron-beam emitters;
processing the acquired image data from the radiation detector to form a sinogram; and
processing the sinogram to produce a tomographic image of radiation attenuation within an object, the object being located within the passage;
where the first and second angular velocity differ.

19. The method of claim 18 further comprising rotating the target ring.

20. The method of claim 18, wherein the target ring is configured to remain stationary.

21. The method of claim 18, wherein the step of processing the acquired image data from the radiation detector to form a sinogram is performed by steps comprising:
forming L-bundles for each geometric line; and
solving equations related to the L-bundles to determine individual line projection values.

22. The method of claim 21, wherein the step of solving equations related to the L-bundles further comprises:
performing a local correlation analysis between source modulation vectors and the local projection data to form a constrained inversion problem;
solving the constrained inversion problem using a method selected from the group consisting of conjugate gradients, regularization techniques, and Tikhonov regularization to obtain a sinogram comprising individual line integral projection data.

23. A multiple-source computed tomography system comprising:
an annular vacuum chamber disposed around a passage;
a supporting system configured to support within the passage an item selected from the group consisting of an object and a living organism to be imaged;
a first and a second target ring disposed within the chamber, the passage passing through an opening of the first and the second target ring;
a plurality of electron beam emitters mounted to a mechanically rotatable emitter gantry within the vacuum chamber, each electron beam emitter configured to emit an electron beam towards the first target ring or the second target ring and to cause emissions of x-rays at an impact location of the electron beam on the first or second target ring;
a first and a second x-ray radiation detector array disposed on a mechanically rotatable detector gantry with an aperture between the first and second X-ray radiation detector array within the passage, the mechanically rotatable detector gantry being configured to rotate at a different rate than the rotatable emitter gantry;
an image processing system configured to receive projection data from the first and second radiation detector array, and to generate tomographic images from the projection data received from the radiation detector array.

24. A multiple-source computed tomography system comprising:
an annular vacuum chamber disposed around a passage;
a supporting system configured to support within the passage an item selected from the group consisting of an object and a living organism to be imaged;
a first and a second target ring disposed within the chamber, the passage passing through an opening of the first and the second target ring;

a plurality of electron beam emitters mounted to a mechanically rotatable emitter gantry within the vacuum chamber, each electron beam emitter configured to emit an electron beam towards the first target ring or the second target ring and to cause emissions of x-rays at an impact location of the electron beam on the first or second target ring;

a radiation detector array disposed on a mechanically rotatable detector gantry within the passage the radiation detector array having an aperture for passage of X-ray radiation, the mechanically rotatable detector gantry being configured to rotate at a different rate than the rotatable emitter gantry;

an image processing system configured to receive projection data from the first and second radiation detector array, and to generate tomographic images from the projection data received from the radiation detector array.

* * * * *